(12) United States Patent
Öberg

(10) Patent No.: US 10,738,283 B2
(45) Date of Patent: *Aug. 11, 2020

(54) ONCOLYTIC ADENOVIRUSES WITH INCREASED PROPORTION OF THE 156R SPLICING ISOFORM OF THE E1B PROTEIN

(71) Applicant: Ixogen Ltd., London (GB)

(72) Inventor: Hans Daniel Öberg, Uppsala (SE)

(73) Assignee: Ixogen Ltd., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/030,204

(22) Filed: Jul. 9, 2018

(65) Prior Publication Data
US 2018/0371425 A1 Dec. 27, 2018

Related U.S. Application Data

(63) Continuation of application No. 14/648,661, filed as application No. PCT/GB2013/053177 on Nov. 29, 2013, now Pat. No. 10,047,347.

(30) Foreign Application Priority Data

Nov. 30, 2012 (GB) .................................. 1221590.1

(51) Int. Cl.
*A61K 39/275* (2006.01)
*C12N 7/00* (2006.01)
*A61K 35/761* (2015.01)

(52) U.S. Cl.
CPC .............. *C12N 7/00* (2013.01); *A61K 35/761* (2013.01); *C12N 2710/10321* (2013.01); *C12N 2710/10322* (2013.01); *C12N 2710/10332* (2013.01)

(58) Field of Classification Search
None
See application file for complete search history.

(56) References Cited

U.S. PATENT DOCUMENTS

| 6,764,674 B1 | 7/2004 | Hermiston et al. |
| 10,047,347 B2 | 8/2018 | Öberg |

(Continued)

FOREIGN PATENT DOCUMENTS

| WO | 9835028 | 8/1998 |
| WO | 2012132369 | 10/2012 |

OTHER PUBLICATIONS

Wold et al., "Chapter three—Syrian hamster as an animal model to study oncolytic adenoviruses and to evaluate the efficacy of antiviral compounds," Adv Cancer Res 115: 69-92 (Year: 2012).*

(Continued)

*Primary Examiner* — M Franco G Salvoza
(74) *Attorney, Agent, or Firm* — Kilpatrick Townsend & Stockton LLP

(57) ABSTRACT

The invention relates to a recombinant adenovirus that has an oncolytic effect in a cancer cell. By modulating the level and type of splice isoforms of the E1B gene product, expressed from the E1B gene, the oncolytic activity of such viruses can be enhanced. The invention provides a recombinant adenovirus in which the proportion of the E1B-156R isoform is increased relative to wild-type levels. Such a recombinant adenovirus may selectivity replicate in cancer cells, thereby killing cancer cells whilst sparing normal cells.

10 Claims, 16 Drawing Sheets

Specification includes a Sequence Listing.

(56) References Cited

U.S. PATENT DOCUMENTS

2005/0186178 A1     8/2005    Ennist et al.
2015/0315547 A1    11/2015    Öberg

OTHER PUBLICATIONS

U.S. Appl. No. 14/648,661, "Non Final Office Action", dated Apr. 20, 2017, 13 pages.
U.S. Appl. No. 14/648,661, "Non-Final Office Action", dated Sep. 7, 2017, 9 pages.
U.S. Appl. No. 14/648,661, "Notice of Allowance", dated Apr. 11, 2018, 8 pages.
U.S. Appl. No. 14/648,661, "Restriction Requirement", dated Nov. 3, 2016, 7 pages.
Ching et al., "The human adenovirus type 5 E1B 55-kilodalton protein is phosphorylated by protein kinase CK2", Journal of Virology, vol. 86(5), available online at http://jvi.asm.org/content/85/5/2400.full.pdf+html, Mar. 2012, pp. 2400-2415.
Choi et al., "Evolution of oncolytic adenovirus for cancer treatment", Advanced Drug Delivery Reviews, vol. 64, Issue 8, Jun. 1, 2012, pp. 720-729.
GB1221590.1, "Search Report", dated Apr. 10, 2013, 4 pages.
Kaliberova et al., "CRAdRGDflt-IL24 virotherapy in combination with chemotherapy of experimental glioma", Cancer Gene Ther. vol. 16, Issue 10, Oct. 2009, pp. 794-805.
Kim et al., "Evaluation of E1 B gene-attenuated replicating adenoviruses for cancer gene therapy", Cancer Gene Ther. vol. 9, issue (9), Apr. 20, 2017, pp. 725-736.
Kindsmuller et al., "A 49-Kilodalton Isoform of the Adenovirus Type 5 Early Region 1B 55-Kilodalton Protein Is Sufficient To Support Virus Replication", Journal of Virology, 83(18), available online at http://europepmc.org/articles/PMC2738261/, Sep. 2009, pp. 9045-9056.
PCT/GB2013/053177, "International Search Report and Written Opinion", dated Mar. 6, 2014, 4 pages.
Sharma et al., "Adenoviral vector-based strategies for cancer therapy", Curr Drug ther. vol. 4 Issue 2, May 1, 2009, pp. 117-138.
Sieber, "Untersuchung des funktionellen Potenzials der Adenovirus Typ 5 E1BN-Proteine", Naturwissenschaftliche Fakultat III, Universitat Regensburg, retrieved from the Internet: http://epub.uni-regensburg.de/12134/1/Diss.T.Sieber2.1_interaktiv.pdf, May 2008, pp. 1-158.

* cited by examiner

FIG. 2
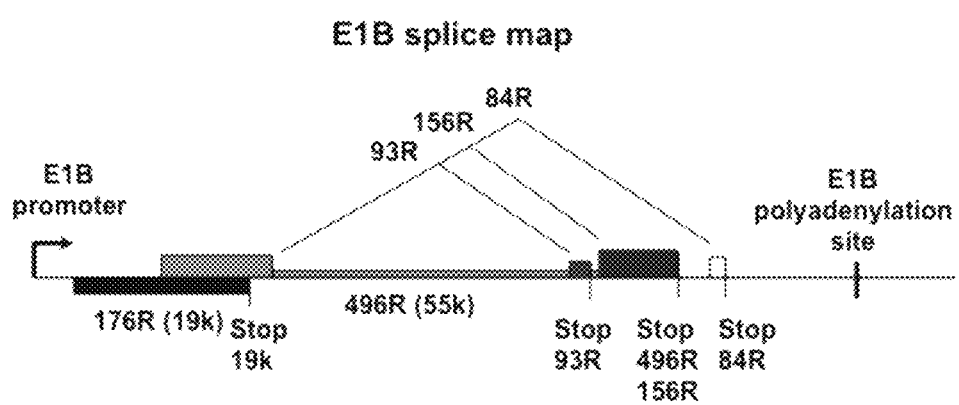
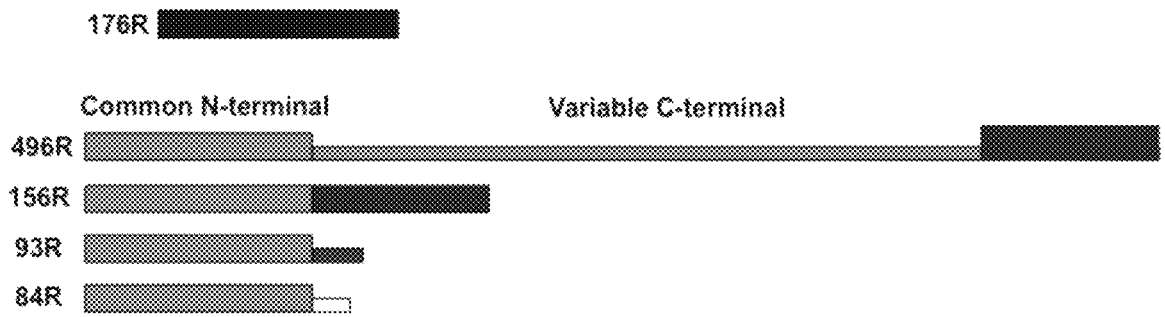

FIG. 9

| NHBE cells | Ad5wt | Onyx-015 | Ixo-ctrl | Ixovex |
|---|---|---|---|---|
| EC50 (pfu/cell) | 0,042 | 0,63 | 0,031 | 23 |
| Relative EC50 | 535 | 36 | 735 | 1,0 |

FIG. 12

| Experiment<br>virus / AdX-156R / cancer cell used /<br>normal cell used | Replication capacity / pfu/cell | | | | OI |
|---|---|---|---|---|---|
| | a | b | c | d | (a/b)/(c/d) |
| Ad5 / Ad5-156R / Hela / NHBE | 3710 | 5.13 | 5989 | 31.0 | 3.7 |
| Ad5 / Ad5-156R / H460 / NHBE | 32662 | 5.13 | 4447 | 31.0 | 44 |
| Ad5 / Ad2-156R / Hela / NHBE | 3366 | 6.26 | 5989 | 31.0 | 2.8 |
| ONYX015 / Ad5-156R / Hela / NHBE | 805 | 242 | 1715 | 2835 | 5.5 |
| Ad2 / Ad5-156R / Hela / NHBE | 39037 | 3731 | 50945 | 73170 | 15 | where:

a = cancer cells (Hela or H460) + AdX-156R b = normal cells (NHBE) + AdX-156R c = cancer cells (Hela or H460) AdX-156R d = normal cells − AdX-156R and oncolytic index (OI) = (OV$_{cancer\ cell}$(a) /OV$_{normal\ cell}$ (b) )/(WT OV$_{cancer\ cell}$ (c) /WT$_{normal\ cell}$ (d)) where OV is oncolytic virus replication capacity and WT is wild type virus replication capacity.

FIG. 13

Adenovirus 156R protein alignment

| Subfamily | Serotype | | |
|---|---|---|---|
| C | Ad1 | SEQ ID NO: 42 | MERRNPSERGVPAGFSGHAFVSSGCETQESPTTVVFRPPGNNTGGAAAATAAAGGSQAA |
| | Ad2 | SEQ ID NO: 43 | MERRNPSERGVPAGFSGHASVESGCETQESPATVVFRPPGNNTDGG-----ATAGGSQAA |
| | Ad6 | SEQ ID NO: 44 | MERRNPSERGVPAGFSGHASVESSGCETQESPATVVFRPPGNNTDGG-----ATAGGSQAA |
| | Ad5 | SEQ ID NO: 3 | MERRNPSERGVPAGFSGHASVESSCETQESPATVVFRPPGNTDGGAA----AAAGGSQ_A |
| E | Ad4 | SEQ ID NO: 45 | MESRNFFQQGLPACFLSSSFVENKEVPAPECNLRLLACTAARHGEDPE-------S |
| B | Ad11 | SEQ ID NO: 46 | MDPADSFQQGIRPGFSGHSIVENMSGSQDEDNLRLLASAAFGCSGNPE---ASTGRAG-G |

The aligning continues on this row from the one above:

| | | |
|---|---|---|
| Ad1 | | AAAGAEPMEPESRPGPSGSNVVQPESMSKVNLNGVFDMTMKIRKVLRYDETRTRCRPCEC |
| Ad2 | | AAAGAEPMEPESRPGPSGSNVVQPESMSKVNLNGVFDMTMKIRKVLRYDETRTRCRPCEC |
| Ad6 | | AAAGAEPMEPESRPGPSGSNVVQPESMSKVNLNGVFDMTMKIRKVLRYDETRTRCRPCEC |
| Ad5 | | AAAGAEPMEPESRPGPSGSNVVQPESMSKVNLNGVFDMTMKIRKVLRYDETRTRCRPCEC |
| Ad4 | | PAAGGSRAEGESRPGPSG----------------GGVADLFPSLR-------RTRCRACEC |
| Ad11 | | GCGGIARQGPESRPGPSSGG------------GGVADLSPELQRILRYDDTRSRVRACEC |

| | | |
|---|---|---|
| Ad1 | | GGKHIRKQPVMLDVTEELRPDHLVLACTRAEFGSSDEDTD |
| Ad2 | | GGKHIRKQPVMLDVTEELRPDHLVLACTRAEFGSSDEDTD |
| Ad6 | | GGKHIRKQPVMLDVTEELRPDHLVLACTRAEFGSSDEDTD |
| Ad5 | | GGKHIRKQPVMLDVTEELRPDHLVLACTRAEFGSSDEDTD |
| Ad4 | | GGKHARFQPVCVDVTEDLRPDHLVLSCTGTEFGSSGEESD |
| Ad11 | | GGKHARFQPVCVDVTEDLRPDHLVIARTCAEFGSSGEETD |

Shaded field. The similarities within group C. Gaps indicates where they differ.
Underlined on Ad5: The amino acids that would single out Ad5-156R from the other 156R in subfamily C.

SEQUENCE LISTING

```
<160> NUMBER OF SEQ ID NOS: 46

<210> SEQ ID NO 1
<211> LENGTH: 2330
<212> TYPE: DNA
<213> ORGANISM: Adenovirus

<400> SEQUENCE: 1
atggaggctt gggagtgttt ggaagatttt tctgctgtgc gtaacttgct ggaacagagc      60
tctaacagta cctcttggtt ttggaggttt ctgtggggct catcccaggc aaagttagtc     120
tgcagaatta aggaggatta caagtgggaa tttgaagagc ttttgaaatc ctgtggtgag     180
ctgtttgatt ctttgaatct gggtcaccag gcgcttttcc aagagaaggt catcaagact     240
ttggattttt ccacaccggg gcgcgctgcg gctgctgttg cttttttgag ttttataaag     300
gataaatgga gcgaagaaac ccatctgagc ggggggtacc tgctggattt tctggccatg     360
catctgtgga gagcggttgt gagacacaag aatcgcctgc tactgttgtc ttccgtccgc     420
ccggcgataa taccgacgga ggagcagcag cagcagcagg aggaagccag gcggcggcgg     480
caggagcaga gcccatggaa cccgagagcc ggcctggacc ctcgggaatg aatgttgtac     540
aggtggctga actgtatcca gaactgagac gcattttgac aattacagag gatgggcagg     600
ggctaaaggg ggtaaagagg gagcggggggg cttgtgaggc tacagaggag gctaggaatc     660
tagcttttag cttaatgacc agacaccgtc ctgagtgtat tacttttcaa cagatcaagg     720
ataattgcgc taatgagctt gatctgctgg cgcagaagta ttccatagag cagctgacca     780
cttactggct gcagccaggg gatgattttg aggaggctat tagggtatat gcaaaggtgg     840
cacttaggcc agattgcaag tacaagatca gcaaacttgt aaatatcagg aattgttgct     900
acatttctgg gaacggggcc gaggtggaga tagatacgga ggatagggtg gcctttagat     960
gtagcatgat aaatatgtgg ccgggggtgc ttggcatgga cggggtggtt attatgaatg    1020
taaggtttac tggccccaat tttagcggta cggttttcct ggccaatacc aaccttatcc    1080
tacacggtgt aagcttctat gggtttaaca atacctgtgt ggaagcctgg accgatgtaa    1140
gggttcgggg ctgtgccttt tactgctgct ggaagggggt ggtgtgtcgc cccaaaagca    1200
gggcttcaat taagaaatgc ctctttgaaa ggtgtacctt gggtatcctg tctgagggta    1260
actccagggt gcgccacaat gtggcctccg actgtggttg cttcatgcta gtgaaaagcg    1320
tggctgtgat taagcataac atggtatgtg gcaactgcga ggacagggcc tctcagatgc    1380
tgacctgctc ggacggcaac tgtcacctgc tgaagaccat tcacgtagcc agccactctc    1440
gcaaggcctg gccagtgttt gagcataaca tactgacccg ctgttccttg catttgggta    1500
acaggagggg ggtgttccta ccttaccaat gcaatttgag tcacactaag atattgcttg    1560
agcccgagag catgtccaag gtgaacctga acggggtgtt tgacatgacc atgaagatct    1620
ggaaggtgct gaggtacgat gagacccgca ccaggtgcag accctgcgag tgtggcggta    1680
```

```
aacatattag gaaccagcct gtgatgctgg atgtgaccga ggagctgagg cccgatcact    1740
tggtgctggc ctgcacccgc gctgagtttg gctctagcga tgaagataca gattgaggta    1800
ctgaaatgtg tgggcgtggc ttaagggtgg gaaagaatat ataaggtggg ggtcttatgt    1860
agttttgtat ctgttttgca gcagccgccg ccgccatgag caccaactcg tttgatggaa    1920
gcattgtgag ctcatatttg acaacgcgca tgccccatg ggccggggtg cgtcagaatg     1980
tgatgggctc cagcattgat ggtcgccccg tcctgcccgc aaactctact accttgacct    2040
acgagaccgt gtctggaacg ccgttggaga ctgcagcctc cgccgccgct tcagccgctg    2100
cagccaccgc ccgcgggatt gtgactgact ttgctttcct gagcccgctt gcaagcagtg    2160
cagcttcccg ttcatccgcc cgcgatgaca agttgacggc tcttttggca caattggatt    2220
ctttgacccg ggaacttaat gtcgtttctc agcagctgtt ggatctgcgc cagcaggttt    2280
ctgccctgaa ggcttcctcc cctcccaatg cggtttaaaa cataaataaa                2330
```

<210> SEQ ID NO 2
<211> LENGTH: 471
<212> TYPE: DNA
<213> ORGANISM: Adenovirus

<400> SEQUENCE: 2

```
atggagcgaa gaaacccatc tgagcggggg gtacctgctg gattttctgg ccatgcatct      60
gtggagagcg gttgtgagac acaagaatcg cctgctactg ttgtcttccg tccgcccggc    120
gataataccg acggaggagc agcagcagca gcaggaggaa gccaggcggc ggcggcagga    180
gcagagccca tggaacccga gccggcct ggaccctcgg gaatgaatgt tgtacagccc      240
gagagcatgt ccaaggtgaa cctgaacggg gtgtttgaca tgaccatgaa gatctggaag    300
gtgctgaggt acgatgagac ccgcaccagg tgcagaccct gcgagtgtgg cggtaaacat    360
attaggaacc agcctgtgat gctggatgtg accgaggagc tgaggcccga tcacttggtg    420
ctggcctgca cccgcgctga gtttggctct agcgatgaag atacagattg a             471
```

<210> SEQ ID NO 3
<211> LENGTH: 156
<212> TYPE: PRT
<213> ORGANISM: Adenovirus

<400> SEQUENCE: 3

```
Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
        35                  40                  45

Ala Ala Ala Gly Gly Ser Gln Ala Ala Ala Gly Ala Glu Pro Met
    50                  55                  60

Glu Pro Glu Ser Arg Pro Gly Pro Ser Gly Met Asn Val Val Gln Pro
65                  70                  75                  80

Glu Ser Met Ser Lys Val Asn Leu Asn Gly Val Phe Asp Met Thr Met
                85                  90                  95

Lys Ile Trp Lys Val Leu Arg Tyr Asp Glu Thr Arg Thr Arg Cys Arg
            100                 105                 110

Pro Cys Glu Cys Gly Gly Lys His Ile Arg Asn Gln Pro Val Met Leu
        115                 120                 125

Asp Val Thr Glu Glu Leu Arg Pro Asp His Leu Val Leu Ala Cys Thr
```

130                 135                 140
Arg Ala Glu Phe Gly Ser Ser Asp Glu Asp Thr Asp
145                 150                 155

<210> SEQ ID NO 4
<211> LENGTH: 1491
<212> TYPE: DNA
<213> ORGANISM: Adenovirus

<400> SEQUENCE: 4

| | | | | | |
|---|---|---|---|---|---|
| atggagcgaa | gaaacccatc | tgagcggggg | gtacctgctg | gattttctgg | ccatgcatct | 60 |
| gtggagagcg | gttgtgagac | acaagaatcg | cctgctactg | ttgtcttccg | tccgcccggc | 120 |
| gataataccg | acggaggagc | agcagcagca | gcaggaggaa | gccaggcggc | ggcggcagga | 180 |
| gcagagccca | tggaacccga | gagccggcct | ggaccctcgg | gaatgaatgt | tgtacaggtg | 240 |
| gctgaactgt | atccagaact | gagacgcatt | ttgacaatta | cagaggatgg | gcaggggcta | 300 |
| aaggggtaa | agaggagcg | gggggcttgt | gaggctacag | aggaggctag | gaatctagct | 360 |
| tttagcttaa | tgaccagaca | ccgtcctgag | tgtattactt | tcaacagat | caaggataat | 420 |
| tgcgctaatg | agcttgatct | gctggcgcag | aagtattcca | tagagcagct | gaccacttac | 480 |
| tggctgcagc | caggggatga | ttttgaggag | gctattaggg | tatatgcaaa | ggtggcactt | 540 |
| aggccagatt | gcaagtacaa | gatcagcaaa | cttgtaaata | tcaggaattg | ttgctacatt | 600 |
| tctgggaacg | gggccgaggt | ggagatagat | acggaggata | gggtggcctt | tagatgtagc | 660 |
| atgataaata | tgtggccggg | ggtgcttggc | atggacgggg | tggttattat | gaatgtaagg | 720 |
| tttactggcc | ccaattttag | cggtacggtt | ttcctggcca | ataccaacct | tatcctacac | 780 |
| ggtgtaagct | tctatgggtt | taacaatacc | tgtgtggaag | cctggaccga | tgtaagggtt | 840 |
| cggggctgtg | ccttttactg | ctgctggaag | ggggtggtgt | gtcgcccaa | aagcagggct | 900 |
| tcaattaaga | aatgcctctt | tgaaaggtgt | accttgggta | tcctgtctga | gggtaactcc | 960 |
| agggtgcgcc | acaatgtggc | ctccgactgt | ggttgcttca | tgctagtgaa | aagcgtggct | 1020 |
| gtgattaagc | ataacatggt | atgtggcaac | tgcgaggaca | gggcctctca | gatgctgacc | 1080 |
| tgctcggacg | gcaactgtca | cctgctgaag | accattcacg | tagccagcca | ctctcgcaag | 1140 |
| gcctggccag | tgtttgagca | taacatactg | acccgctgtt | ccttgcattt | gggtaacagg | 1200 |
| aggggggtgt | tcctacccta | ccaatgcaat | ttgagtcaca | ctaagatatt | gcttgagccc | 1260 |
| gagagcatgt | ccaaggtgaa | cctgaacggg | gtgtttgaca | tgaccatgaa | gatctggaag | 1320 |
| gtgctgaggt | acgatgagac | ccgcaccagg | tgcagaccct | gcgagtgtgg | cggtaaacat | 1380 |
| attaggaacc | agcctgtgat | gctggatgtg | accgaggagc | tgaggcccga | tcacttggtg | 1440 |
| ctggcctgca | cccgcgctga | gtttggctct | agcgatgaag | atacagattg | a | 1491 |

<210> SEQ ID NO 5
<211> LENGTH: 496
<212> TYPE: PRT
<213> ORGANISM: Adenovirus

<400> SEQUENCE: 5

Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
                20                  25                  30

Thr Val Val Phe Arg Pro Pro Gly Asp Asn Thr Asp Gly Gly Ala Ala
            35                  40                  45

-continued

```
Ala Ala Ala Gly Gly Ser Gln Ala Ala Ala Gly Ala Glu Pro Met
 50              55                  60
Glu Pro Glu Ser Arg Pro Gly Pro Ser Gly Met Asn Val Val Gln Val
 65                  70                  75                  80
Ala Glu Leu Tyr Pro Glu Leu Arg Arg Ile Leu Thr Ile Thr Glu Asp
                 85                  90                  95
Gly Gln Gly Leu Lys Gly Val Lys Arg Glu Arg Gly Ala Cys Glu Ala
            100                 105                 110
Thr Glu Glu Ala Arg Asn Leu Ala Phe Ser Leu Met Thr Arg His Arg
            115                 120                 125
Pro Glu Cys Ile Thr Phe Gln Gln Ile Lys Asp Asn Cys Ala Asn Glu
            130                 135                 140
Leu Asp Leu Leu Ala Gln Lys Tyr Ser Ile Glu Gln Leu Thr Thr Tyr
145                 150                 155                 160
Trp Leu Gln Pro Gly Asp Asp Phe Glu Glu Ala Ile Arg Val Tyr Ala
                165                 170                 175
Lys Val Ala Leu Arg Pro Asp Cys Lys Tyr Lys Ile Ser Lys Leu Val
            180                 185                 190
Asn Ile Arg Asn Cys Cys Tyr Ile Ser Gly Asn Gly Ala Glu Val Glu
            195                 200                 205
Ile Asp Thr Glu Asp Arg Val Ala Phe Arg Cys Ser Met Ile Asn Met
210                 215                 220
Trp Pro Gly Val Leu Gly Met Asp Gly Val Val Ile Met Asn Val Arg
225                 230                 235                 240
Phe Thr Gly Pro Asn Phe Ser Gly Thr Val Phe Leu Ala Asn Thr Asn
                245                 250                 255
Leu Ile Leu His Gly Val Ser Phe Tyr Gly Phe Asn Asn Thr Cys Val
            260                 265                 270
Glu Ala Trp Thr Asp Val Arg Val Arg Gly Cys Ala Phe Tyr Cys Cys
            275                 280                 285
Trp Lys Gly Val Val Cys Arg Pro Lys Ser Arg Ala Ser Ile Lys Lys
            290                 295                 300
Cys Leu Phe Glu Arg Cys Thr Leu Gly Ile Leu Ser Glu Gly Asn Ser
305                 310                 315                 320
Arg Val Arg His Asn Val Ala Ser Asp Cys Gly Cys Phe Met Leu Val
                325                 330                 335
Lys Ser Val Ala Val Ile Lys His Asn Met Val Cys Gly Asn Cys Glu
            340                 345                 350
Asp Arg Ala Ser Gln Met Leu Thr Cys Ser Asp Gly Asn Cys His Leu
            355                 360                 365
Leu Lys Thr Ile His Val Ala Ser His Ser Arg Lys Ala Trp Pro Val
            370                 375                 380
Phe Glu His Asn Ile Leu Thr Arg Cys Ser Leu His Leu Gly Asn Arg
385                 390                 395                 400
Arg Gly Val Phe Leu Pro Tyr Gln Cys Asn Leu Ser His Thr Lys Ile
                405                 410                 415
Leu Leu Glu Pro Glu Ser Met Ser Lys Val Asn Leu Asn Gly Val Phe
            420                 425                 430
Asp Met Thr Met Lys Ile Trp Lys Val Leu Arg Tyr Asp Glu Thr Arg
            435                 440                 445
Thr Arg Cys Arg Pro Cys Glu Cys Gly Gly Lys His Ile Arg Asn Gln
            450                 455                 460
```

Pro Val Met Leu Asp Val Thr Glu Glu Leu Arg Pro Asp His Leu Val
465                 470                 475                 480

Leu Ala Cys Thr Arg Ala Glu Phe Gly Ser Ser Asp Glu Asp Thr Asp
                485                 490                 495

<210> SEQ ID NO 6
<211> LENGTH: 282
<212> TYPE: DNA
<213> ORGANISM: Adenovirus

<400> SEQUENCE: 6
atggagcgaa gaaacccatc tgagcggggg gtacctgctg gattttctgg ccatgcatct      60
gtggagagcg gttgtgagac acaagaatcg cctgctactg ttgtcttccg tccgcccggc     120
gataataccg acggaggagc agcagcagca gcaggaggaa gccaggcggc ggcggcagga     180
gcagagccca tggaacccga gagccggcct ggaccctcgg gaatgaatgt tgtacaggag     240
gggggtgttc ctaccttacc aatgcaattt gagtcacact aa                        282

<210> SEQ ID NO 7
<211> LENGTH: 93
<212> TYPE: PRT
<213> ORGANISM: Adenovirus

<400> SEQUENCE: 7

Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
        35                  40                  45

Ala Ala Ala Gly Gly Ser Gln Ala Ala Ala Gly Ala Glu Pro Met
    50                  55                  60

Glu Pro Glu Ser Arg Pro Gly Pro Ser Gly Met Asn Val Val Gln Glu
65                  70                  75                  80

Gly Gly Val Pro Thr Leu Pro Met Gln Phe Glu Ser His
                85                  90

<210> SEQ ID NO 8
<211> LENGTH: 255
<212> TYPE: DNA
<213> ORGANISM: Adenovirus

<400> SEQUENCE: 8
atggagcgaa gaaacccatc tgagcggggg gtacctgctg gattttctgg ccatgcatct      60
gtggagagcg gttgtgagac acaagaatcg cctgctactg ttgtcttccg tccgcccggc     120
gataataccg acggaggagc agcagcagca gcaggaggaa gccaggcggc ggcggcagga     180
gcagagccca tggaacccga gagccggcct ggaccctcgg gaatgaatgt tgtacagcag     240
ccgccgccgc catga                                                      255

<210> SEQ ID NO 9
<211> LENGTH: 84
<212> TYPE: PRT
<213> ORGANISM: Adenovirus

<400> SEQUENCE: 9

Met Glu Arg Arg Asn Pro Ser Glu Arg Gly Val Pro Ala Gly Phe Ser
1               5                   10                  15

```
Gly His Ala Ser Val Glu Ser Gly Cys Glu Thr Gln Glu Ser Pro Ala
             20                  25                  30

Thr Val Val Phe Arg Pro Pro Gly Asp Asn Thr Asp Gly Gly Ala Ala
         35                  40                  45

Ala Ala Ala Gly Gly Ser Gln Ala Ala Ala Ala Gly Ala Glu Pro Met
     50                  55                  60

Glu Pro Glu Ser Arg Pro Gly Pro Ser Gly Met Asn Val Val Gln Gln
 65                  70                  75                  80

Pro Pro Pro Pro

<210> SEQ ID NO 10
<211> LENGTH: 13
<212> TYPE: DNA
<213> ORGANISM: Adenovirus

<400> SEQUENCE: 10
caggtggctg aac                                                         13

<210> SEQ ID NO 11
<211> LENGTH: 23
<212> TYPE: DNA
<213> ORGANISM: Adenovirus

<400> SEQUENCE: 11
tccttgcatt tgggtaacag gag                                              23

<210> SEQ ID NO 12
<211> LENGTH: 23
<212> TYPE: DNA
<213> ORGANISM: Adenovirus

<400> SEQUENCE: 12
acactaagat attgcttgag ccc                                              23

<210> SEQ ID NO 13
<211> LENGTH: 33
<212> TYPE: DNA
<213> ORGANISM: Adenovirus

<400> SEQUENCE: 13
gtcttatgta gttttgtatc tgttttgcag cag                                   33

<210> SEQ ID NO 14
<211> LENGTH: 13
<212> TYPE: DNA
<213> ORGANISM: Adenovirus

<400> SEQUENCE: 14
gaggtactga aat                                                         13

<210> SEQ ID NO 15
<211> LENGTH: 44
<212> TYPE: DNA
<213> ORGANISM: Artificial Sequence
<220> FEATURE:
<223> OTHER INFORMATION: Primer

<400> SEQUENCE: 15
ccacctcgag ttaattaaca tcatcaataa tataccttat tttg                       44

<210> SEQ ID NO 16
<211> LENGTH: 34
```

```
<212> TYPE: DNA
<213> ORGANISM: Artificial Sequence
<220> FEATURE:
<223> OTHER INFORMATION: Primer

<400> SEQUENCE: 16
gtgggtttaa acggatttgg tcagggaaaa catg                                  34

<210> SEQ ID NO 17
<211> LENGTH: 46
<212> TYPE: DNA
<213> ORGANISM: Artificial Sequence
<220> FEATURE:
<223> OTHER INFORMATION: Primer

<400> SEQUENCE: 17
ccttgcattt gggtaataga agaggagtgt tcctacctta ccaatg                     46

<210> SEQ ID NO 18
<211> LENGTH: 46
<212> TYPE: DNA
<213> ORGANISM: Artificial Sequence
<220> FEATURE:
<223> OTHER INFORMATION: Primer

<400> SEQUENCE: 18
cattggtaag gtaggaacac tcctcttcta ttacccaaat gcaagg                     46

<210> SEQ ID NO 19
<211> LENGTH: 36
<212> TYPE: DNA
<213> ORGANISM: Artificial Sequence
<220> FEATURE:
<223> OTHER INFORMATION: Primer

<400> SEQUENCE: 19
cttgcatttg ggtaacagga gggggtgtt cctacc                                 36

<210> SEQ ID NO 20
<211> LENGTH: 36
<212> TYPE: DNA
<213> ORGANISM: Artificial Sequence
<220> FEATURE:
<223> OTHER INFORMATION: Primer

<400> SEQUENCE: 20
ggtaggaaca ccccctcct gttacccaaa tgcaag                                 36

<210> SEQ ID NO 21
<211> LENGTH: 32
<212> TYPE: DNA
<213> ORGANISM: Artificial Sequence
<220> FEATURE:
<223> OTHER INFORMATION: Primer

<400> SEQUENCE: 21
ctaagatatt gctggaaccc gagagcatgt cc                                    32

<210> SEQ ID NO 22
<211> LENGTH: 32
<212> TYPE: DNA
<213> ORGANISM: Artificial Sequence
<220> FEATURE:
<223> OTHER INFORMATION: Primer

<400> SEQUENCE: 22
```

```
ggacatgctc tcgggttcca gcaatatctt ag                                    32
```

<210> SEQ ID NO 23
<211> LENGTH: 28
<212> TYPE: DNA
<213> ORGANISM: Artificial Sequence
<220> FEATURE:
<223> OTHER INFORMATION: Primer

<400> SEQUENCE: 23

```
catttgggta acagaagagg ggtgttcc                                         28
```

<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24

```
ggaacacccc tcttctgtta cccaaatg                                         28
```

<210> SEQ ID NO 25
<211> LENGTH: 33
<212> TYPE: DNA
<213> ORGANISM: Artificial Sequence
<220> FEATURE:
<223> OTHER INFORMATION: Primer

<400> SEQUENCE: 25

```
gaatgaatgt tgtacaagtc gctgaactgt atc                                   33
```

<210> SEQ ID NO 26
<211> LENGTH: 33
<212> TYPE: DNA
<213> ORGANISM: Artificial Sequence
<220> FEATURE:
<223> OTHER INFORMATION: Primer

<400> SEQUENCE: 26

```
gatacagttc agcgacttgt acaacattca ttc                                   33
```

<210> SEQ ID NO 27
<211> LENGTH: 36
<212> TYPE: DNA
<213> ORGANISM: Artificial Sequence
<220> FEATURE:
<223> OTHER INFORMATION: Primer

<400> SEQUENCE: 27

```
gtggctgaac tgtatccata actgagacgc attttg                                36
```

<210> SEQ ID NO 28
<211> LENGTH: 36
<212> TYPE: DNA
<213> ORGANISM: Artificial Sequence
<220> FEATURE:
<223> OTHER INFORMATION: Primer

<400> SEQUENCE: 28

```
caaaatgcgt ctcagttatg gatacagttc agccac                                36
```

<210> SEQ ID NO 29
<211> LENGTH: 21
<212> TYPE: DNA
<213> ORGANISM: Artificial Sequence -continued

```
<220> FEATURE:
<223> OTHER INFORMATION: Primer

<400> SEQUENCE: 29
gcctgctact gttgtcttcc g                                                  21

<210> SEQ ID NO 30
<211> LENGTH: 19
<212> TYPE: DNA
<213> ORGANISM: Artificial Sequence
<220> FEATURE:
<223> OTHER INFORMATION: Primer

<400> SEQUENCE: 30 caccccctc ctgtacaac                                                      19

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
gacatgctct cgggctgtac aac                                                23

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
caaacgagtt ggtgctcatg                                                    20

<210> SEQ ID NO 33
<211> LENGTH: 38
<212> TYPE: DNA
<213> ORGANISM: Artificial Sequence
<220> FEATURE:
<223> OTHER INFORMATION: Primer

<400> SEQUENCE: 33
ctcgaggaat tcgccaccat ggagcgaaga aacccatc                                38

<210> SEQ ID NO 34
<211> LENGTH: 33
<212> TYPE: DNA
<213> ORGANISM: Artificial Sequence
<220> FEATURE:
<223> OTHER INFORMATION: Primer

<400> SEQUENCE: 34
cacttctaga tcaatctgta tcttcatcgc tag                                     33

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ggagatttgg acggtcttgg                                                    20
```

```
<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
ggatcccatc acattttgac g                                             21

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
catccatgga ggtttgggc                                                19

<210> SEQ ID NO 38
<211> LENGTH: 21
<212> TYPE: DNA
<213> ORGANISM: Artificial Sequence
<220> FEATURE:
<223> OTHER INFORMATION: Primer

<400> SEQUENCE: 38
ccttaaaaga agcgtttcca c                                             21

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
catttgggta acgggagggg ggtgttcc                                      28

<210> SEQ ID NO 40
<211> LENGTH: 28
<212> TYPE: DNA
<213> ORGANISM: Artificial Sequence
<220> FEATURE:
<223> OTHER INFORMATION: Primer

<400> SEQUENCE: 40
ggaacacccc cctcccgtta cccaaatg                                      28

<210> SEQ ID NO 41
<211> LENGTH: 35938
<212> TYPE: DNA
<213> ORGANISM: Adenovirus

<400> SEQUENCE: 41
catcatcaat aatataccct attttggatt gaagccaata tgataatgag ggggtggagt    60
ttgtgacgtg gcgcggggcg tgggaacggg gcgggtgacg tagtagtgtg gcggaagtgt   120
gatgttgcaa gtgtggcgga acacatgtaa gcgacggatg tggcaaaagt gacgtttttg   180
gtgtgcgccg gtgtacacag gaagtgacaa ttttcgcgcg gttttaggcg gatgttgtag   240
taaatttggg cgtaaccgag taagatttgg ccatttccgc gggaaaactg aataagagga   300
agtgaaatct gaataatttt gtgttactca tagcgcgtaa tatttgtcta gggccgcggg   360
```

```
gactttgacc gtttacgtgg agactcgccc aggtgttttt ctcaggtgtt ttccgcgttc      420
cgggtcaaag ttggcgtttt attattatag tcagctgacg tgtagtgtat ttatacccgg      480
tgagttcctc aagaggccac tcttgagtgc cagcgagtag agttttctcc tccgagccgc      540
tccgacaccg ggactgaaaa tgagacatat tatctgccac ggaggtgtta ttaccgaaga      600
aatggccgcc agtcttttgg accagctgat cgaagaggta ctggctgata atcttccacc      660
tcctagccat tttgaaccac ctacccttca cgaactgtat gatttagacg tgacggcccc      720
cgaagatccc aacgaggagg cggtttcgca gattttccc gactctgtaa tgttggcggt       780
gcaggaaggg attgacttac tcactttcc gccggcgccc ggttctccgg agccgcctca       840
cctttcccgg cagcccgagc agccggagca gagagccttg ggtccggttt ctatgccaaa     900
ccttgtaccg gaggtgatcg atcttacctg ccacgaggct ggctttccac ccagtgacga     960
cgaggatgaa gagggtgagg agtttgtgtt agattatgtg gagcaccccg ggcacggttg    1020
caggtcttgt cattatcacc ggaggaatac gggggaccca gatattatgt gttcgctttg    1080
ctatatgagg acctgtggca tgtttgtcta cagtaagtga aaattatggg cagtgggtga    1140
tagagtggtg ggtttggtgt ggtaattttt tttttaattt ttacagtttt gtggtttaaa    1200
gaattttgta ttgtgatttt tttaaaaggt cctgtgtctg aacctgagcc tgagcccgag    1260
ccagaaccgg agcctgcaag acctaccgc cgtcctaaaa tggcgcctgc tatcctgaga     1320
cgcccgacat cacctgtgtc tagagaatgc aatagtagta cggatagctg tgactccggt    1380
ccttctaaca cacctcctga gatacacccg gtggtcccgc tgtgcccat taaaccagtt     1440 gccgtgagag ttggtgggcg tcgccaggct gtggaatgta tcgaggactt gcttaacgag    1500
cctgggcaac ctttggactt gagctgtaaa cgcccaggc cataaggtgt aaacctgtga     1560
ttgcgtgtgt ggttaacgcc tttgtttgct gaatgagttg atgtaagttt aataaagggt    1620
gagataatgt ttaacttgca tggcgtgtta aatggggcgg ggcttaaagg gtatataatg    1680
cgccgtgggc taatcttggt tacatctgac ctcatggagg cttgggagtg tttggaagat    1740
ttttctgctg tgcgtaactt gctggaacag agctctaaca gtacctcttg gttttggagg    1800
tttctgtggg gctcatccca ggcaaagtta gtctgcagaa ttaaggagga ttacaagtgg    1860
gaatttgaag agcttttgaa atcctgtggt gagctgtttg attctttgaa tctgggtcac    1920
caggcgcttt tccaagagaa ggtcatcaag actttggatt tttccacacc ggggcgcgct    1980
gcggctgctg ttgcttttt gagttttata aaggataaat ggagcgaaga aacccatctg    2040 agcgggggt acctgctgga ttttctggcc atgcatctgt ggagagcggt tgtgagacac    2100
aagaatcgcc tgctactgtt gtcttccgtc cgccggcga taataccgac ggaggagcag    2160
cagcagcagc aggaggaagc caggcggcgg cggcaggagc agagcccatg gaacccgaga    2220
gccggcctgg accctcggga atgaatgttg tacaggtggc tgaactgtat ccagaactga    2280
gacgcatttt gacaattaca gaggatgggc aggggctaaa gggggtaaag agggagcggg    2340
gggcttgtga ggctacagag gaggctagga atctagcttt tagcttaatg accagacacc    2400
gtcctgagtg tattactttt caacagatca aggataattg cgctaatgag cttgatctgc    2460
tggcgcagaa gtattccata gagcagctga ccacttactg gctgcagcca ggggatgatt    2520
ttgaggaggc tattagggta tatgcaaagg tggcacttag gccagattgc aagtacaaga    2580 tcagcaaaact tgtaaatatc aggaattgtt gctacatttc tgggaacggg gccgaggtgg    2640
agatagatac ggaggatagg gtggcccttta gatgtagcat gataaatatg tggccggggg    2700
```

-continued

```
tgcttggcat ggacggggtg gttattatga atgtaaggtt tactggcccc aattttagcg    2760
gtacggtttt cctggccaat accaacctta tcctacacgg tgtaagcttc tatgggttta    2820
acaatacctg tgtggaagcc tggaccgatg taagggttcg gggctgtgcc ttttactgct    2880
gctggaaggg ggtggtgtgt cgccccaaaa gcagggcttc aattaagaaa tgcctctttg    2940
aaaggtgtac cttgggtatc ctgtctgagg gtaactccag ggtgcgccac aatgtggcct    3000
ccgactgtgg ttgcttcatg ctagtgaaaa gcgtggctgt gattaagcat aacatggtat    3060
gtggcaactg cgaggacagg gcctctcaga tgctgacctg ctcggacggc aactgtcacc    3120
tgctgaagac cattcacgta gccagccact ctcgcaaggc ctggccagtg tttgagcata    3180
acatactgac ccgctgttcc ttgcatttgg gtaacaggag gggggtgttc ctaccttacc    3240
aatgcaattt gagtcacact aagatattgc ttgagcccga gagcatgtcc aaggtgaacc    3300
tgaacggggt gtttgacatg accatgaaga tctggaaggt gctgaggtac gatgagaccc    3360
gcaccaggtg cagaccctgc gagtgtggcg gtaaacatat taggaaccag cctgtgatgc    3420
tggatgtgac cgaggagctg aggcccgatc acttggtgct ggcctgcacc cgcgctgagt    3480
ttggctctag cgatgaagat acagattgag gtactgaaat gtgtgggcgt ggcttaaggg    3540
tgggaaagaa tatataaggt gggggtctta tgtagttttg tatctgtttt gcagcagccg    3600
ccgccgccat gagcaccaac tcgtttgatg gaagcattgt gagctcatat ttgacaacgc    3660
gcatgccccc atgggccggg gtgcgtcaga atgtgatggg ctccagcatt gatggtcgcc    3720
ccgtcctgcc cgcaaactct actaccttga cctacgagac cgtgtctgga acgccgttgg    3780
agactgcagc ctccgccgcc gcttcagccg ctgcagccac cgcccgcggg attgtgactg    3840
actttgcttt cctgagcccg cttgcaagca gtgcagcttc ccgttcatcc gcccgcgatg    3900
acaagttgac ggctcttttg gcacaattgg attctttgac ccgggaactt aatgtcgttt    3960
ctcagcagct gttggatctg cgccagcagg tttctgccct gaaggcttcc tcccctccca    4020
atgcggttta aaacataaat aaaaaaccag actctgtttg gatttggatc aagcaagtgt    4080
cttgctgtct ttatttaggg gttttgcgcg cgcggtaggc ccgggaccag cggtctcggt    4140
cgttgagggt cctgtgtatt ttttccagga cgtggtaaag gtgactctgg atgttcagat    4200
acatgggcat aagcccgtct ctggggtgga ggtagcacca ctgcagagct tcatgctgcg    4260
gggtggtgtt gtagatgatc cagtcgtagc aggagcgctg ggcgtggtgc ctaaaaatgt    4320 cttttcagtag caagctgatt gccaggggca ggcccttggt gtaagtgttt acaaagcggt    4380
taagctggga tgggtgcata cgtggggata tgagatgcat cttggactgt attttttaggt    4440 tggctatgtt cccagccata tccctccggg gattcatgtt gtgcagaacc accagcacag    4500
tgtatccggt gcacttggga aatttgtcat gtagcttaga aggaaatgcg tggaagaact    4560
tggagacgcc cttgtgacct ccaagatttt ccatgcattc gtccataatg atggcaatgg    4620
gcccacgggc ggcggcctgg gcgaagatat ttctgggatc actaacgtca tagttgtgtt    4680
ccaggatgag atcgtcatag gccatttttta caaagcgcgg gcggagggtg ccagactgcg    4740
gtataatggt tccatccggc ccaggggcgt agttaccctc acagatttgc atttcccacg    4800
ctttgagttc agatgggggg atcatgtcta cctgcgggc gatgaagaaa acggtttccg    4860
gggtagggga gatcagctgg gaagaaagca ggttcctgag cagctgcgac ttaccgcagc    4920
cggtgggccc gtaaatcaca cctattaccg ggtgcaactg gtagttaaga gagctgcagc    4980
tgccgtcatc cctgagcagg ggggccactt cgttaagcat gtccctgact cgcatgttttt    5040 ccctgaccaa atccgccaga aggcgctcgc cgcccagcga tagcagttct tgcaaggaag    5100
```

```
caaagttttt caacggtttg agaccgtccg ccgtaggcat gcttttgagc gtttgaccaa    5160
gcagttccag gcggtcccac agctcggtca cctgctctac ggcatctcga tccagcatat    5220
ctcctcgttt cgcgggttgg ggcggctttc gctgtacggc agtagtcggt gctcgtccag    5280
acgggccagg gtcatgtctt tccacgggcg cagggtcctc gtcagcgtag tctgggtcac    5340
ggtgaagggg tgcgctccgg gctgcgcgct ggccagggtg cgcttgaggc tggtcctgct    5400
ggtgctgaag cgctgccggt cttcgccctg cgcgtcggcc aggtagcatt tgaccatggt    5460
gtcatagtcc agcccctccg cggcgtggcc cttggcgcgc agcttgccct tggaggaggc    5520
gccgcacgag gggcagtgca gacttttgag ggcgtagagc ttgggcgcga gaaataccga    5580
ttccggggag taggcatccg cgccgcaggc cccgcagacg gtctcgcatt ccacgagcca    5640
ggtgagctct ggccgttcgg ggtcaaaaac caggtttccc ccatgctttt tgatgcgttt    5700
cttacctctg gtttccatga gccggtgtcc acgctcggtg acgaaaaggc tgtccgtgtc    5760
cccgtataca gacttgagag gcctgtcctc gagcggtgtt ccgcggtcct cctcgtatag    5820
aaactcggac cactctgaga caaaggctcg cgtccaggcc agcacgaagg aggctaagtg    5880
ggaggggtag cggtcgttgt ccactagggg gtccactcgc tccagggtgt gaagacacat    5940
gtcgccctct tcggcatcaa ggaaggtgat tggtttgtag gtgtaggcca cgtgaccggg    6000
tgttcctgaa gggggctat aaaaggggt ggggcgcgt tcgtcctcac tctcttccgc    6060
atcgctgtct gcgagggcca gctgttgggg tgagtactcc ctctgaaaag cgggcatgac    6120
ttctgcgcta agattgtcag tttccaaaaa cgaggaggat ttgatattca cctggcccgc    6180
ggtgatgcct ttgagggtgg ccgcatccat ctggtcagaa aagacaatct ttttgttgtc    6240
aagcttggtg gcaaacgacc cgtagagggc gttggacagc aacttggcga tggagcgcag    6300
ggtttggttt ttgtcgcgat cggcgcgctc cttggccgcg atgtttagct gcacgtattc    6360
gcgcgcaacg caccgccatt cgggaaagac ggtggtgcgc tcgtcgggca ccaggtgcac    6420
gcgccaaccg cggttgtgca gggtgacaag gtcaacgctg gtggctacct ctccgcgtag    6480
gcgctcgttg gtccagcaga ggcggccgcc cttgcgcgag cagaatggcg gtaggggtc    6540 tagctgcgtc tcgtccgggg ggtctgcgtc cacggtaaag accccgggca gcaggcgcgc    6600
gtcgaagtag tctatcttgc atccttgcaa gtctagcgcc tgctgccatg cgcgggcggc    6660
aagcgcgcgc tcgtatgggt tgagtggggg accccatggc atgggtggg tgagcgcgga    6720 ggcgtacatg ccgcaaatgt cgtaaacgta gagggctct ctgagtattc caagatatgt    6780
agggtagcat cttccaccgc ggatgctggc gcgcacgtaa tcgtatagtt cgtgcgaggg    6840
agcgaggagg tcgggaccga ggttgctacg ggcgggctgc tctgctcgga agactatctg    6900
cctgaagatg gcatgtgagt tggatgatat ggttggacgc tggaagacgt tgaagctggc    6960
gtctgtgaga cctaccgcgt cacgcacgaa ggaggcgtag gagtcgcgca gcttgttgac    7020
cagctcggcg gtgacctgca cgtctagggc gcagtagtcc agggtttcct tgatgatgtc    7080
atacttatcc tgtccctttt ttttccacag ctcgcggttg aggacaaact cttcgcggtc    7140
tttccagtac tcttggatcg gaaacccgtc ggcctccgaa cggtaagagc ctagcatgta    7200
gaactggttg acgcctggt aggcgcagca tcccttttct acgggtagcg cgtatgcctg    7260
cgcggccttc cggagcgagg tgtgggtgag cgcaaaggtg tccctgacca tgactttgag    7320
gtactggtat ttgaagtcag tgtcgtcgca tccgccctgc tcccagagca aaaagtccgt    7380 gcgcttttg gaacgcggat ttggcagggc gaaggtgaca tcgttgaaga gtatctttcc    7440
```

```
cgcgcgaggc ataaagttgc gtgtgatgcg aagggtccc ggcacctcgg aacggttgtt      7500
aattacctgg gcggcgagca cgatctcgtc aaagccgttg atgttgtggc ccacaatgta      7560
aagttccaag aagcgcggga tgcccttgat ggaaggcaat tttttaagtt cctcgtaggt      7620
gagctcttca ggggagctga gcccgtgctc tgaaagggcc cagtctgcaa gatgagggtt      7680
ggaagcgacg aatgagctcc acaggtcacg ggccattagc atttgcaggt ggtcgcgaaa      7740
ggtcctaaac tggcgaccta tggccatttt ttctggggtg atgcagtaga aggtaagcgg      7800
gtcttgttcc cagcggtccc atccaaggtt cgcggctagg tctcgcgcgg cagtcactag      7860
aggctcatct ccgccgaact tcatgaccag catgaagggc acgagctgct tcccaaaggc      7920
ccccatccaa gtataggtct ctacatcgta ggtgacaaag agacgctcgg tgcgaggatg      7980
cgagccgatc gggaagaact ggatctcccg ccaccaattg gaggagtggc tattgatgtg      8040
gtgaaagtag aagtccctgc gacgggccga acactcgtgc tggcttttgt aaaaacgtgc      8100
gcagtactgg cagcggtgca cgggctgtac atcctgcacg aggttgacct gacgaccgcg      8160
cacaaggaag cagagtggga atttgagccc ctcgcctggc gggtttggct ggtggtcttc      8220
tacttcggct gcttgtcctt gaccgtctgg ctgctcgagg ggagttacgg tggatcggac      8280
caccacgccg cgcgagccca agtccagat gtccgcgcgc ggcggtcgga gcttgatgac      8340
aacatcgcgc agatgggagc tgtccatggt ctggagctcc cgcggcgtca ggtcaggcgg      8400
gagctcctgc aggtttacct cgcatagacg ggtcagggcg cgggctagat ccaggtgata      8460
cctaatttcc aggggctggt tggtggcggc gtcgatggct tgcaagaggc cgcatccccg      8520
cggcgcgact acggtaccgc gcggcgggcg gtgggccgcg ggggtgtcct tggatgatgc      8580
atctaaaagc ggtgacgcgg gcgagccccc ggaggtaggg ggggctccgg acccgccggg      8640 agaggggggca ggggcacgtc ggccgccgcg cgggcagga gctggtgctg cgcgcgtagg      8700
ttgctggcga acgcgacgac gcggcggttg atctcctgaa tctggcgcct ctgcgtgaag      8760
acgacgggcc cggtgagctt gagcctgaaa gagagttcga cagaatcaat ttcggtgtcg      8820
ttgacggcgg cctggcgcaa aatctcctgc acgtctcctg agttgtcttg ataggcgatc      8880
tcggccatga actgctcgat ctcttcctcc tggagatctc cgcgtccggc tcgctccacg      8940
gtggcggcga ggtcgttgga aatgcgggcc atgagctgcg agaaggcgtt gaggcctccc      9000
tcgttccaga cgcggctgta gaccacgccc ccttcggcat cgcgggcgcg catgaccacc      9060
tgcgcgagat tgagctccac gtgccgggcg aagacggcgt agtttcgcag gcgctgaaag      9120
aggtagttga gggtggtggc ggtgtgttct gccacgaaga agtacataac ccagcgtcgc      9180
aacgtggatt cgttgatatc ccccaaggcc tcaaggcgct ccatggcctc gtagaagtcc      9240
acggcgaagt tgaaaaactg ggagttgcgc gccgacacgg ttaactcctc ctccagaaga      9300
cggatgagct cggcgacagt gtcgcgcacc tcgcgctcaa aggctacagg ggcctcttct      9360
tcttcttcaa tctcctcttc cataagggcc tccccttctt cttcttctgg cggcggtggg      9420 ggaggggggga cacggcggcg acgacggcgc accgggaggc ggtcgacaaa gcgctcgatc      9480
atctccccgc ggcgacggcg catggtctcg gtgacggcgc ggccgttctc gcggggcgc      9540 agttggaaga cgccgcccgt catgtcccgg ttatgggttg gcgggggggct gccatgcggc      9600 agggatacgg cgctaacgat gcatctcaac aattgttgtg taggtactcc gccgccgagg      9660
gacctgagcg agtccgcatc gaccggatcg gaaaacctct cgagaaaggc gtctaaccag      9720
tcacagtcgc aaggtaggct gagcaccgtg gcggcggca gcgggcggcg gtcgggttg       9780 tttctggcgg aggtgctgct gatgatgtaa ttaaagtagg cggtcttgag acggcggatg      9840
```

```
gtcgacagaa gcaccatgtc cttgggtccg gcctgctgaa tgcgcaggcg gtcggccatg    9900
ccccaggctt cgttttgaca tcggcgcagg tctttgtagt agtcttgcat gagcctttct    9960
accggcactt cttcttctcc ttcctcttgt cctgcatctc ttgcatctat cgctgcggcg   10020
gcggcggagt ttggccgtag gtggcgccct cttcctccca tgcgtgtgac cccgaagccc   10080
ctcatcggct gaagcagggc taggtcggcg acaacgcgct cggctaatat ggcctgctgc   10140
acctgcgtga gggtagactg gaagtcatcc atgtccacaa agcggtggta tgcgcccgtg   10200
ttgatggtgt aagtgcagtt ggccataacg gaccagttaa cggtctggtg acccggctgc   10260
gagagctcgg tgtacctgag acgcgagtaa gccctcgagt caaatacgta gtcgttgcaa   10320
gtccgcacca ggtactggta tcccaccaaa aagtgcggcg gcggctggcg gtagaggggc   10380
cagcgtaggg tggccggggc tccggggcg agatcttcca acataaggcg atgatatccg    10440
tagatgtacc tggacatcca ggtgatgccg gcggcggtgg tggaggcgcg cggaaagtcg   10500
cggacgcggt tccagatgtt gcgcagcggc aaaaagtgct ccatggtcgg gacgctctgg   10560
ccggtcaggc gcgcgcaatc gttgacgctc tagaccgtgc aaaaggagag cctgtaagcg   10620
ggcactcttc cgtggtctgg tggataaatt cgcaagggta tcatggcgga cgaccggggt   10680
tcgagccccg tatccggccg tccgccgtga tccatgcggt taccgcccgc gtgtcgaacc   10740
caggtgtgcg acgtcagaca acgggggagt gctccttttg gcttcttcc aggcgcggcg     10800 gctgctgcgc tagcttttttt ggccactggc cgcgcgcagc gtaagcggtt aggctggaaa   10860
gcgaaagcat taagtggctc gctccctgta gccgagggt tattttccaa gggttgagtc     10920
gcgggacccc cggttcgagt ctcggaccgg ccggactgcg gcgaacgggg gtttgcctcc   10980
ccgtcatgca agaccccgct tgcaaattcc tccggaaaca gggacgagcc ccttttttgc   11040 tttttcccaga tgcatccggt gctgcggcag atgcgccccc ctcctcagca gcggcaagag   11100
caagagcagc ggcagacatg cagggcaccc tcccctcctc ctaccgcgtc aggagggggcg   11160 acatccgcgg ttgacgcggc agcagatggt gattacgaac cccgcggcg ccgggcccgg     11220 cactacctgg acttggagga gggcgagggc ctggcgcggc taggagcgcc ctctcctgag   11280
cggtacccaa gggtgcagct gaagcgtgat acgcgtgagg cgtacgtgcc gcggcagaac   11340
ctgtttcgcg accgcgaggg agaggagccc gaggagatgc gggatcgaaa gttccacgca   11400
gggcgcgagc tgcggcatgg cctgaatcgc gagcggttgc tgcgcgagga ggactttgag   11460
cccgacgcgc gaaccgggat tagtcccgcg cgcgcacacg tggcggccgc cgacctggta   11520
accgcatacg agcagacggt gaaccaggag attaactttc aaaaaagctt taacaaccac   11580
gtgcgtacgc ttgtggcgcg cgaggaggtg gctataggac tgatgcatct gtgggacttt   11640
gtaagcgcgc tggagcaaaa cccaaatagc aagccgctca tggcgcagct gttccttata   11700
gtgcagcaca gcagggacaa cgaggcattc agggatgcgc tgctaaacat agtagagccc   11760
gagggccgct ggctgctcga tttgataaac atcctgcaga gcatagtggt gcaggagcgc   11820
agcttgagcc tggctgacaa ggtggccgcc atcaactatt ccatgcttag cctgggcaag   11880
ttttacgccc gcaagatata ccatacccct tacgttccca tagacaagga ggtaaagatc   11940 gagggggttct acatgcgcat ggcgctgaag gtgcttacct tgagcgacga cctgggcgtt   12000
tatcgcaacg agcgcatcca caaggccgtg agcgtgagcc ggcggcgcga gctcagcgac   12060
cgcgagctga tgcacagcct gcaaagggcc ctggctggca cgggcagcgg cgatagagag   12120
gccgagtcct actttgacgc gggcgctgac ctgcgctggg ccccaagccg acgcgccctg   12180
```

-continued

```
gaggcagctg gggccggacc tgggctggcg gtggcacccg cgcgcgctgg caacgtcggc   12240
ggcgtggagg aatatgacga ggacgatgag tacgagccag aggacggcga gtactaagcg   12300
gtgatgtttc tgatcagatg atgcaagacg caacggaccc ggcggtgcgg gcggcgctgc   12360
agagccagcc gtccggcctt aactccacgg acgactggcg ccaggtcatg gaccgcatca   12420
tgtcgctgac tgcgcgcaat cctgacgcgt tccggcagca gccgcaggcc aaccggctct   12480
ccgcaattct ggaagcggtg gtcccggcgc gcgcaaaccc cacgcacgag aaggtgctgg   12540
cgatcgtaaa cgcgctggcc gaaaacaggg ccatccggcc cgacgaggcc ggcctggtct   12600
acgacgcgct gcttcagcgc gtggctcgtt acaacagcgg caacgtgcag accaacctgg   12660
accggctggt gggggatgtg cgcgaggccg tggcgcagcg tgagcgcgcg cagcagcagg   12720
gcaacctggg ctccatggtt gcactaaacg ccttcctgag tacacagccc gccaacgtgc   12780
cgcggggaca ggaggactac accaactttg tgagcgcact gcggctaatg gtgactgaga   12840
caccgcaaag tgaggtgtac cagtctgggc cagactattt tttccagacc agtagacaag   12900
gcctgcagac cgtaaacctg agccaggctt tcaaaaactt gcaggggctg tggggggtgc   12960
gggctcccac aggcgaccgc gcgaccgtgt ctagcttgct gacgcccaac tcgcgcctgt   13020
tgctgctgct aatagcgccc ttcacggaca gtggcagcgt gtcccgggac atatacctag   13080
gtcacttgct gacactgtac cgcgaggcca taggtcaggc gcatgtggac gagcatactt   13140
tccaggagat tacaagtgtc agccgcgcgc tggggcagga ggacacgggc agcctggagg   13200
caaccctaaa ctacctgctg accaaccggc ggcagaagat cccctcgttg cacagtttaa   13260
acagcgagga ggagcgcatt ttgcgctacg tgcagcagag cgtgagcctt aacctgatgc   13320
gcgacggggt aacgcccagc gtggcgctgg acatgaccgc gcgcaacatg gaaccgggca   13380
tgtatgcctc aaaccggccg tttatcaacc gcctaatgga ctacttgcat cgcgcggccg   13440
ccgtgaaccc cgagtatttc accaatgcca tcttgaaccc gcactggcta ccgcccctg   13500
gtttctacac cggggggattc gaggtgcccg agggtaacga tggattcctc tgggacgaca   13560
tagacgacag cgtgttttcc ccgcaaccgc agaccctgct agagttgcaa cagcgcgagc   13620
aggcagaggc ggcgctgcga aaggaaagct tccgcaggcc aagcagcttg tccgatctag   13680
gcgctgcggc cccgcggtca gatgctagta gcccatttcc aagcttgata gggtctctta   13740
ccagcactcg caccacccgc ccgcgcctgc tgggcgagga ggagtaccta acaactcgc   13800
tgctgcagcc gcagcgcgaa aaaaacctgc ctccggcatt tcccaacaac gggatagaga   13860
gcctagtgga caagatgagt agatggaaga cgtacgcgca ggagcacagg gacgtgccag   13920
gcccgcgccc gcccacccgt cgtcaaaggc acgaccgtca gcggggtctg gtgtgggagg   13980
acgatgactc ggcagacgac agcagcgtcc tggatttggg agggagtggc aacccgtttg   14040
cgcaccttcg ccccaggctg gggagaatgt tttaaaaaaa aaaaagcatg atgcaaaata   14100
aaaaactcac caaggccatg gcaccgagcg ttggttttct tgtattcccc ttagtatgcg   14160
gcgcgcggcg atgtatgagg aaggtcctcc tccctcctac gagagtgtgg tgagcgcggc   14220
gccagtggcg gcggcgctgg gttctccctt cgatgctccc ctggaccgc cgtttgtgcc   14280
tccgcggtac ctgcggccta ccgggggag aaacagcatc cgttactctg agttggcacc   14340
cctattcgac accacccgtg tgtacctggt ggacaacaag tcaacggatg tggcatccct   14400
gaactaccag aacgaccaca gcaactttct gaccacggtc attcaaaaca atgactacag   14460
cccgggggag gcaagcacac agaccatcaa tcttgacgac cggtcgcact ggggcggcga   14520
cctgaaaacc atcctgcata ccaacatgcc aaatgtgaac gagttcatgt ttaccaataa   14580
```

```
gtttaaggcg cgggtgatgg tgtcgcgctt gcctactaag gacaatcagg tggagctgaa    14640
atacgagtgg gtggagttca cgctgcccga gggcaactac tccgagacca tgaccataga    14700
ccttatgaac aacgcgatcg tggagcacta cttgaaagtg ggcagacaga acggggttct    14760
ggaaagcgac atcggggtaa agtttgacac ccgcaacttc agactggggt ttgaccccgt    14820
cactggtctt gtcatgcctg ggtatatac aaacgaagcc ttccatccag acatcatttt    14880
gctgccagga tgcggggtgg acttcaccca cagccgcctg agcaacttgt tgggcatccg    14940
caagcggcaa cccttccagg agggctttag gatcacctac gatgatctgg agggtggtaa    15000
cattcccgca ctgttggatg tggacgccta ccaggcgagc ttgaaagatg acaccgaaca    15060 gggcggggt ggcgcaggcg gcagcaacag cagtggcagc ggcgcggaag agaactccaa    15120
cgcggcagcc gcggcaatgc agccggtgga ggacatgaac gatcatgcca ttcgcggcga    15180
cacctttgcc acacgggctg aggagaagcg cgctgaggcc gaagcagcgg ccgaagctgc    15240
cgcccccgct gcgcaacccg aggtcgagaa gcctcagaag aaaccggtga tcaaaccccct   15300 gacagaggac agcaagaaac gcagttacaa cctaataagc aatgacagca ccttcaccca    15360
gtaccgcagc tggtaccttg catacaacta cggcgaccct cagaccggaa tccgctcatg    15420
gaccctgctt tgcactcctg acgtaacctg cggctcggag caggtctact ggtcgttgcc    15480
agacatgatg caagacccg tgaccttccg ctccacgcgc cagatcagca actttccggt    15540
ggtgggcgcc gagctgttgc ccgtgcactc caagagcttc tacaacgacc aggccgtcta    15600
ctcccaactc atccgccagt ttacctctct gacccacgtg ttcaatcgct ttcccgagaa    15660 ccagatttg gcgcgcccgc cagccccac catcaccacc gtcagtgaaa acgttcctgc    15720
tctcacagat cacgggacgc taccgctgcg caacagcatc ggaggagtcc agcgagtgac    15780
cattactgac gccagacgcc gcacctgccc ctacgtttac aaggccctgg gcatagtctc    15840
gccgcgcgtc ctatcgagcc gcactttttg agcaagcatg tccatcctta tatcgcccag    15900
caataacaca ggctggggcc tgcgcttccc aagcaagatg tttggcgggg ccaagaagcg    15960
ctccgaccaa cacccagtgc gcgtgcgcgg gcactaccgc gcgccctggg gcgcgcacaa    16020
acgcggccgc actgggcgca ccaccgtcga tgacgccatc gacgcggtgg tggaggaggc    16080
gcgcaactac acgccacgc cgccaccagt gtccacagtg gacgcggcca ttcagaccgt    16140
ggtgcgcgga gcccggcgct atgctaaaat gaagagacgg cggaggcgcg tagcacgtcg    16200
ccaccgccgc cgacccggca ctgccgccca acgcgcggcg gcggccctgc ttaaccgcgc    16260
acgtcgcacc ggccgacggg cggccatgcg ggccgctcga aggctggccg cgggtattgt    16320
cactgtgccc cccaggtcca ggcgacgagc ggccgccgca gcagccgcgg ccattagtgc    16380
tatgactcag ggtcgcaggg gcaacgtgta ttgggtgcgc gactcggtta gcggcctgcg    16440
cgtgcccgtg cgcacccgcc ccccgcgcaa ctagattgca agaaaaaact acttagactc    16500
gtactgttgt atgtatccag cggcggcggc gcgcaacgaa gctatgtcca agcgcaaaat    16560
caaagaagag atgctccagg tcatcgcgcc ggagatctat ggccccccga agaaggaaga    16620
gcaggattac aagccccgaa agctaaagcg ggtcaaaaag aaaaagaaag atgatgatga    16680
tgaacttgac gacgaggtgg aactgctgca cgctaccgcg cccaggcgac gggtacagtg    16740
gaaaggtcga cgcgtaaaac gtgttttgcg accccggcacc accgtagtct ttacgcccgg    16800
tgagcgctcc acccgcacct acaagcgcgt gtatgatgag gtgtacgcg acgaggacct    16860 gcttgagcag gccaacgagc gcctcgggga gtttgcctac ggaaagcggc ataaggacat    16920
```

```
gctggcgttg ccgctggacg agggcaaccc aacacctagc ctaaagcccg taacactgca    16980
gcaggtgctg cccgcgcttg caccgtccga agaaaagcgc ggcctaaagc gcgagtctgg    17040
tgacttggca cccaccgtgc agctgatggt acccaagcgc cagcgactgg aagatgtctt    17100
ggaaaaaatg accgtggaac ctgggctgga gcccgaggtc cgcgtgcggc caatcaagca    17160
ggtggcgccg ggactgggcg tgcagaccgt ggacgttcag atacccacta ccagtagcac    17220
cagtattgcc accgccacag agggcatgga gacacaaacg tccccggttg cctcagcggt    17280
ggcggatgcc gcggtgcagg cggtcgctgc ggccgcgtcc aagacctcta cggaggtgca    17340
aacggacccg tggatgtttc gcgtttcagc ccccggcgc ccgcgcggtt cgaggaagta     17400
cggcgccgcc agcgcgctac tgcccgaata tgccctacat ccttccattg cgcctacccc    17460
cggctatcgt ggctacacct accgcccag aagacgagca actacccgac gccgaaccac     17520
cactggaacc cgccgccgcc gtcgccgtcg ccagcccgtg ctggccccga tttccgtgcg    17580
cagggtggct cgcgaaggag gcaggaccct ggtgctgcca acagcgcgct accaccccag    17640
catcgtttaa aagccggtct ttgtggttct tgcagatatg ccctcacct gccgcctccg     17700 tttcccggtg ccgggattcc gaggaagaat gcaccgtagg aggggcatgg ccggccacgg    17760
cctgacgggc ggcatgcgtc gtgcgcacca ccggcggcgg cgcgcgtcgc accgtcgcat    17820
gcgcggcggt atcctgcccc tccttattcc actgatcgcc gcggcgattg cgccgtgcc     17880 cggaattgca tccgtggcct tgcaggcgca gagacactga ttaaaaacaa gttgcatgtg    17940
gaaaaatcaa aataaaaagt ctggactctc acgctcgctt ggtcctgtaa ctattttgta    18000
gaatggaaga catcaacttt gcgtctctgg ccccgcgaca cggctcgcgc ccgttcatgg    18060
gaaactggca agatatcggc accagcaata tgagcggtgg cgccttcagc tggggctcgc    18120
tgtggagcgg cattaaaaat ttcggttcca ccgttaagaa ctatggcagc aaggcctgga    18180
acagcagcac aggccagatg ctgagggata agttgaaaga gcaaaatttc caacaaaagg    18240
tggtagatgg cctggcctct ggcattagcg gggtggtgga cctggccaac caggcagtgc    18300
aaaataagat taacagtaag cttgatcccc gccctcccgt agaggagcct ccaccggccg    18360
tggagacagt gtctccagag gggcgtggcg aaaagcgtcc gcgccccgac agggaagaaa    18420
ctctggtgac gcaaatagac gagcctccct cgtacgagga ggcactaaag caaggcctgc    18480
ccaccacccg tccatcgcg cccatggcta ccggagtgct gggccagcac acacccgtaa     18540
cgctggacct gcctccccc gccgacaccc agcagaaacc tgtgctgcca ggcccgaccg     18600
ccgttgttgt aacccgtcct agccgcgcgt ccctgcgccg cgccgccagc ggtccgcgat    18660
cgttgcggcc cgtagccagt ggcaactggc aaagcacact gaacagcatc gtgggtctgg    18720
gggtgcaatc cctgaagcgc cgacgatgct tctgaatagc taacgtgtcg tatgtgtgtc    18780
atgtatgcgt ccatgtcgcc gccagaggag ctgctgagcc gccgcgcgcc cgcttttcaa    18840
gatggctacc ccttcgatga tgccgcagtg gtcttacatg cacatctcgg gccaggacgc    18900
ctcggagtac ctgagccccg ggctggtgca gtttgcccgc gccaccgaga cgtacttcag    18960
cctgaataac aagtttagaa accccacggt ggcgcctacg cacgacgtga ccacagaccg    19020
gtcccagcgt ttgacgctgc ggttcatccc tgtggaccgt gaggatactg cgtactcgta    19080
caaggcgcgg ttcacccctag ctgtgggtga taaccgtgtg ctggacatgg cttccacgta   19140
ctttgacatc cgcggcgtgc tggacagggg ccctacttt aagccctact ctggcactgc     19200
ctacaacgcc ctggctccca agggtgcccc aaatccttgc gaatgggatg aagctgctac    19260
tgctcttgaa ataaacctag aagaagagga cgatgacaac gaagacgaag tagacgagca    19320
```

```
agctgagcag caaaaaactc acgtatttgg gcaggcgcct tattctggta taaatattac  19380
aaaggagggt attcaaatag gtgtcgaagg tcaaacacct aaatatgccg ataaaacatt  19440
tcaacctgaa cctcaaatag gagaatctca gtggtacgaa actgaaatta atcatgcagc  19500
tgggagagtc cttaaaaaga ctaccccaat gaaaccatgt tacggttcat atgcaaaacc  19560
cacaaatgaa aatggagggc aaggcattct tgtaaagcaa caaatggaaa gctagaaag   19620
tcaagtggaa atgcaatttt tctcaactac tgaggcgacc gcaggcaatg gtgataactt  19680
gactcctaaa gtggtattgt acagtgaaga tgtagatata gaaacccag acactcatat   19740
ttcttacatg cccactatta aggaaggtaa ctcacgagaa ctaatgggcc aacaatctat  19800
gcccaacagg cctaattaca ttgcttttag ggacaatttt attggtctaa tgtattacaa  19860
cagcacgggt aatatgggtg ttctggcggg ccaagcatcg cagttgaatg ctgttgtaga  19920
tttgcaagac agaaacacag agctttcata ccagcttttg cttgattcca ttggtgatag  19980
aaccaggtac ttttctatgt ggaatcaggc tgttgacagc tatgatccag atgttagaat  20040
tattgaaaat catggaactg aagatgaact tccaaattac tgctttccac tgggaggtgt  20100
gattaataca gagactctta ccaaggtaaa acctaaaaca ggtcaggaaa atggatggga  20160
aaagatgct acagaatttt cagataaaaa tgaataaga gttggaaata attttgccat    20220
ggaaatcaat ctaatgcca acctgtggag aaatttcctg tactccaaca tagcgctgta   20280
tttgcccgac aagctaaagt acagtccttc caacgtaaaa atttctgata cccaaacac   20340
ctacgactac atgaacaagc gagtggtggc tcccgggtta gtggactgct acattaacct  20400
tggagcacgc tggtcccttg actatatgga caacgtcaac ccatttaacc accaccgcaa  20460
tgctggcctg cgctaccgct caatgttgct gggcaatggt cgctatgtgc ccttccacat  20520
ccaggtgcct cagaagttct tgccattaa aaacctcctt ctcctgccgg gctcatacac    20580
ctacgagtgg aacttcagga aggatgttaa catggttctg cagagctccc taggaaatga  20640
cctaagggtt gacggagcca gcattaagtt tgatagcatt tgcctttacg ccaccttctt  20700
ccccatggcc cacaacaccg cctccacgct tgaggccatg cttagaaacg acaccaacga  20760
ccagtccttt aacgactatc tctccgccgc caacatgctc taccctatac cgccaacgc   20820
taccaacgtg cccatatcca tcccctcccg caactgggcg ctttccgcg gctgggcctt   20880
cacgcgcctt aagactaagg aaaccccatc actgggctcg ggctacgacc ttattacac   20940
ctactctggc tctataccct acctagatgg aaccttttac ctcaaccaca cctttaagaa  21000
ggtggccatt acctttgact cttctgtcag ctggcctggc aatgaccgcc tgcttacccc  21060
caacgagttt gaaattaagc gctcagttga cggggagggt tacaacgttg cccagtgtaa  21120
catgaccaaa gactggttcc tggtacaaat gctagctaac tacaacattg ctaccaggg   21180
cttctatatc ccagagagct acaaggaccg catgtactcc ttctttagaa acttccagcc  21240
catgagccgt caggtggtgg atgatactaa atacaaggac taccaacagg tgggcatcct  21300
acaccaacac aacaactctg gatttgttgg ctaccttgcc cccaccatgc gcgaaggaca  21360
ggcctaccct gctaacttcc cctatccgct tataggcaag accgcagttg acagcattac  21420
ccagaaaaag tttctttgcg atcgcaccct ttggcgcatc ccattctcca gtaacttat   21480
gtccatgggc gcactcacag acctgggcca aaaccttctc tacgccaact ccgcccacgc  21540
gctagacatg acttttgagg tggatccat ggacgagccc accttctttc atgttttgtt   21600
tgaagtcttt gacgtggtcc gtgtgcaccg gccgcaccgc ggcgtcatcg aaaccgtgta  21660
```

```
cctgcgcacg cccttctcgg ccggcaacgc cacaacataa agaagcaagc aacatcaaca    21720
acagctgccg ccatgggctc cagtgagcag gaactgaaag ccattgtcaa agatcttggt    21780
tgtgggccat attttttggg cacctatgac aagcgctttc caggctttgt ttctccacac    21840
aagctcgcct gcgccatagt caatacggcc ggtcgcgaga ctgggggcgt acactggatg    21900
gcctttgcct ggaacccgca ctcaaaaaca tgctacctct ttgagccctt tggctttttct   21960 gaccagcgac tcaagcaggt ttaccagttt gagtacgagt cactcctgcg ccgtagcgcc    22020
attgcttctt cccccgaccg ctgtataacg ctggaaaagt ccacccaaag cgtacagggg    22080
cccaactcgg ccgcctgtgg actattctgc tgcatgtttc tccacgcctt tgccaactgg    22140
ccccaaactc ccatggatca aaccccacc atgaaccta ttaccggggt acccaactcc       22200
atgctcaaca gtccccaggt acagcccacc ctgcgtcgca accaggaaca gctctacagc    22260
ttcctggagc gccactcgcc ctacttccgc agccacagtg cgcagattag gagcgccact    22320 tcttttgtc acttgaaaaa catgtaaaaa taatgtacta gagacacttt caataaaggc     22380
aaatgctttt atttgtacac tctcgggtga ttatttaccc ccacccttgc cgtctgcgcc    22440
gtttaaaaat caaggggtt ctgccgcgca tcgctatgcg ccactggcag ggacacgttg     22500
cgatactggt gtttagtgct ccacttaaac tcaggcacaa ccatccgcgg cagctcggtg    22560
aagttttcac tccacaggct gcgcaccatc accaacgcgt ttagcaggtc gggcgccgat    22620
atcttgaagt cgcagttggg gcctccgccc tgcgcgcgcg agttgcgata cacagggttg    22680
cagcactgga acactatcag cgccgggtgg tgcacgctgg ccagcacgct cttgtcggag    22740
atcagatccg cgtccaggtc ctccgcgttg ctcaggcga acggagtcaa ctttggtagc     22800
tgccttccca aaagggcgc gtgcccaggc tttgagttgc actcgcaccg tagtggcatc     22860
aaaaggtgac cgtgcccggt ctgggcgtta ggatacagcg cctgcataaa gccttgatc     22920 tgcttaaaag ccacctgagc cttttgcgcct tcagagaaga acatgccgca agacttgccg    22980
gaaaactgat tggccggaca ggccgcgtcg tgcacgcagc accttgcgtc ggtgttggag   23040
atctgcacca catttcggcc ccaccggttc ttcacgatct tggccttgct agactgctcc    23100
ttcagcgcgc gctgcccgtt ttcgctcgtc acatccattt caatcacgtg ctccttattt   23160
atcataatgc ttccgtgtag acacttaagc tcgccttcga tctcagcgca gcggtgcagc   23220
cacaacgcgc agcccgtggg ctcgtgatgc ttgtaggtca cctctgcaaa cgactgcagg   23280
tacgcctgca ggaatcgccc catcatcgtc acaaaggtct tgttgctggt gaaggtcagc   23340
tgcaacccgc ggtgctcctc gttcagccag gtcttgcata cggccgccag agcttccact   23400
tggtcaggca gtagtttgaa gttcgccttt agatcgttat ccacgtggta cttgtccatc   23460
agcgcgcgcg cagcctccat gcccttctcc cacgcagaca cgatcggcac actcagcggg   23520
ttcatcaccg taatttcact ttccgcttcg ctgggctctt cctcttcctc ttgcgtccgc   23580
ataccacgcg ccactgggtc gtcttcattc agccgccgca ctgtgcgctt acctcctttg   23640
ccatgcttga ttagcaccgg tgggttgctg aaacccacca tttgtagcgc cacatcttct   23700
ctttcttcct cgctgtccac gattacctct ggtgatggcg ggcgctcggg cttgggagaa   23760
gggcgcttct ttttcttctt gggcgcaatg gccaaatccg ccgccgaggt cgatggccgc   23820
gggctgggtg tgcgcggcac cagcgcgtct tgtgatgagt cttcctcgtc ctcggactcg   23880
atacgccgcc tcatccgctt tttgggggc gccggggag gcggcggcga cggggacggg    23940
gacgacacgt cctccatggt tggggacgt cgcgccgcac cgcgtccgcg ctcggggtg     24000 gtttcgcgct gctcctcttc ccgactggcc atttccttct cctataggca gaaaaagatc   24060
```

```
atggagtcag tcgagaagaa ggacagccta accgccccct ctgagttcgc caccaccgcc    24120
tccaccgatg ccgccaacgc gcctaccacc ttccccgtcg aggcaccccc gcttgaggag    24180
gaggaagtga ttatcgagca ggacccaggt tttgtaagcg aagacgacga ggaccgctca    24240
gtaccaacag aggataaaaa gcaagaccag gacaacgcag aggcaaacga ggaacaagtc    24300
gggcgggggg acgaaaggca tggcgactac ctagatgtgg gagacgacgt gctgttgaag    24360
catctgcagc gccagtgcgc cattatctgc gacgcgttgc aagagcgcag cgatgtgccc    24420
ctcgccatag cggatgtcag ccttgcctac gaacgccacc tattctcacc gcgcgtaccc    24480
cccaaacgcc aagaaaacgg cacatgcgag cccaacccgc gcctcaactt ctaccccgta    24540
tttgccgtgc cagaggtgct tgccacctat cacatctttt tccaaaactg caagatagcc    24600
ctatcctgcc gtgccaaccg cagccgagcg acaagcagc tggccttgcg gcagggcgct    24660
gtcatacctg atatcgcctc gctcaacgaa gtgccaaaaa tctttgaggg tcttggacgc    24720
gacgagaagc gcgcggcaaa cgctctgcaa caggaaaaca gcgaaaatga agtcactct    24780 ggagtgttgg tggaactcga gggtgacaac gcgcgcctag ccgtactaaa acgcagcatc    24840
gaggtcaccc actttgccta cccggcactt aacctacccc ccaaggtcat gagcacagtc    24900
atgagtgagc tgatcgtgcg ccgtgcgcag cccctggaga gggatgcaaa tttgcaagaa    24960
caaacagagg agggcctacc cgcagttggc gacgagcagc tagcgcgctg gcttcaaacg    25020
cgcgagcctg ccgacttgga ggagcgacgc aaactaatga tggccgcagt gctcgttacc    25080
gtggagcttg agtgcatgca gcggttcttt gctgacccgg agatgcagcg caagctagag    25140
gaaacattgc actacacctt tcgacagggc tacgtacgcc aggcctgcaa gatctccaac    25200
gtggagctct gcaacctggt ctcctacctt ggaattttgc acgaaaaccg ccttgggcaa    25260
aacgtgcttc attccacgct caagggcgag gcgcgccgcg actacgtccg cgactgcgtt    25320
tacttatttc tatgctacac ctggcagacg gccatgggcg tttggcagca gtgcttggag    25380
gagtgcaacc tcaaggagct gcagaaactg ctaaagcaaa acttgaagga cctatggacg    25440
gccttcaacg agcgctccgt ggccgcgcac ctggcgaca tcattttccc cgaacgcctg    25500
cttaaaaccc tgcaacaggg tctgccagac ttcaccagtc aaagcatgtt gcagaacttt    25560 aggaactta tcctagagcg ctcaggaatc ttgcccgcca cctgctgtgc acttcctagc    25620
gactttgtgc ccattaagta ccgcgaatgc cctccgccgc tttggggcca ctgctacctt    25680
ctgcagctag ccaactacct tgcctaccac tctgacataa tggaagacgt gagcggtgac    25740
ggtctactgg agtgtcactg tcgctgcaac ctatgcaccc gcaccgctc cctggtttgc    25800 aattcgcagc tgcttaacga aagtcaaatt atcggtacct ttgagctgca gggtccctcg    25860
cctgacgaaa agtccgcggc tccgggggttg aaactcactc cggggctgtg acgtcggct    25920 taccttcgca aatttgtacc tgaggactac cacgcccacg agattaggtt ctacgaagac    25980
caatcccgcc cgccaaatgc ggagcttacc gcctgcgtca ttacccaggg ccacattctt    26040
ggccaattgc aagccatcaa caaagcccgc caagagtttc tgctacgaaa gggacggggg    26100
gtttacttgg accccagtc cggcgaggag ctcaacccaa tccccccgcc gccgcagccc    26160
tatcagcagc agccgcgggc ccttgcttcc aggatggca cccaaaaaga agctgcagct    26220
gccgccgcca cccacggacg aggaggaata ctgggacagt caggcagagg aggttttgga    26280
cgaggaggag gaggacatga tggaagactg ggagagccta gacgaggaag cttccgaggt    26340
cgaagaggtg tcagacgaaa caccgtcacc ctcggtcgca ttcccctcgc cggcgcccca    26400
```

```
gaaatcggca accggttcca gcatggctac aacctccgct cctcaggcgc cgccggcact   26460
gcccgttcgc cgacccaacc gtagatggga caccactgga accagggccg gtaagtccaa   26520
gcagccgccg ccgttagccc aagagcaaca acagcgccaa ggctaccgct catggcgcgg   26580
gcacaagaac gccatagttg cttgcttgca agactgtggg ggcaacatct ccttcgcccg   26640
ccgcttcctt ctctaccatc acggcgtggc cttcccccgt aacatcctgc attactaccg   26700
tcatctctac agcccatact gcaccggcgg cagcggcagc ggcagcaaca gcagcggcca   26760
cacagaagca aaggcgaccg gatagcaaga ctctgacaaa gcccaagaaa tccacagcgg   26820
cggcagcagc aggaggagga gcgctgcgtc tggcgcccaa cgaacccgta tcgacccgcg   26880
agcttagaaa caggattttt cccactctgt atgctatatt tcaacagagc aggggccaag   26940
aacaagagct gaaataaaa acaggtctc tgcgatccct cacccgcagc tgcctgtatc   27000
acaaaagcga agatcagctt cggcgcacgc tggaagacgc ggaggctctc ttcagtaaat   27060
actgcgcgct gactcttaag gactagtttc gcgccctttc tcaaatttaa gcgcgaaaac   27120
tacgtcatct ccagcggcca cacccggcgc cagcacctgt cgtcagcgcc attatgagca   27180
aggaaattcc cacgccctac atgtggagtt accagccaca aatgggactt gcggctggag   27240
ctgcccaaga ctactcaacc cgaataaact acatgagcgc gggaccccac atgatatccc   27300
gggtcaacgg aatccgcgcc caccgaaacc gaattctctt ggaacaggcg gctattacca   27360
ccacacctcg taataacctt aatccccgta gttggcccgc tgcctggtg taccaggaaa   27420 gtcccgctcc caccactgtg gtacttccca gagacgccca ggccgaagtt cagatgacta   27480 actcagggggc gcagcttgcg ggcggctttc gtcacagggt gcggtcgccc gggcaggta   27540 taactcacct gacaatcaga gggcgaggta ttcagctcaa cgacgagtcg gtgagctcct   27600
cgcttggtct ccgtccggac gggacatttc agatcggcgg cgccggccgt ccttcattca   27660
cgcctcgtca ggcaatccta actctgcaga cctcgtcctc tgagccgcgc tctggaggca   27720
ttggaactct gcaattttatt gaggagtttg tgccatcggt ctactttaac cccttctcgg   27780
gacctcccgg ccactatccg gatcaattta ttcctaactt tgacgcggta aaggactcgg   27840
cggacggcta cgactgaatg ttaagtggag aggcagagca actgcgcctg aaacacctgg   27900
tccactgtcg ccgccacaag tgctttgccc gcgactccgg tgagttttgc tactttgaat   27960
tgcccgagga tcatatcgag ggccggcgc acggcgtccg gcttaccgcc cagggagagc   28020
ttgcccgtag cctgattcgg gagtttaccc agcgcccct gctagttgag cgggacaggg   28080
gaccctgtgt tctcactgtg atttgcaact gtcctaacct tggattacat caagatcttt   28140
gttgccatct ctgtgctgag tataataaat acagaaatta aaatatactg gggctcctat   28200
cgccatcctg taaacgccac cgtcttcacc cgcccaagca aaccaaggcg aaccttacct   28260 ggtacttta acatctctcc ctctgtgatt tacaacagtt tcaacccaga cggagtgagt   28320
ctacgagaga acctctccga gctcagctac tccatcagaa aaaacaccac cctccttacc   28380
tgccgggaac gtacgagtgc gtcaccggcc gctgcaccac acctaccgcc tgaccgtaaa   28440
ccagactttt tccggacaga cctcaataac tctgtttacc agaacaggag gtgagcttag   28500 aaaacccta gggtattagg ccaaaggcgc agctactgtg gggtttatga acaattcaag   28560
caactctacg ggctattcta attcaggttt tctctagaatc ggggttgggg ttattctctg   28620
tcttgtgatt ctcttattc ttatactaac gcttctctgc ctaaggctcg ccgcctgctg   28680
tgtgcacatt tgcattttatt gtcagctttt taaacgctgg ggtcgccacc caagatgatt   28740
aggtacataa tcctaggttt actcacccct gcgtcagccc acggtaccac ccaaaaggtg   28800
```

```
gattttaagg agccagcctg taatgttaca ttcgcagctg aagctaatga gtgcaccact   28860
cttataaaat gcaccacaga acatgaaaag ctgcttattc gccacaaaaa caaaattggc   28920
aagtatgctg tttatgctat ttggcagcca ggtgacacta cagagtataa tgttacagtt   28980
ttccagggta aaagtcataa aacttttatg tatacttttc cattttatga aatgtgcgac   29040
attaccatgt acatgagcaa acagtataag ttgtggcccc cacaaaattg tgtggaaaac   29100
actggcactt tctgctgcac tgctatgcta attacagtgc tcgctttggt ctgtacccta   29160
ctctatatta aatacaaaag cagacgcagc tttattgagg aaaagaaaat gccttaattt   29220
actaagttac aaagctaatg tcaccactaa ctgctttact cgctgcttgc aaaacaaatt   29280
caaaaagtta gcattataat tagaatagga tttaaacccc ccggtcattt cctgctcaat   29340
accattcccc tgaacaattg actctatgtg ggatatgctc cagcgctaca accttgaagt   29400
caggcttcct ggatgtcagc atctgacttt ggccagcacc tgtcccgcgg atttgttcca   29460
gtccaactac agcgacccac cctaacagag atgaccaaca caaccaacgc ggccgccgct   29520
accggactta catctaccac aaatacaccc caagtttctg cctttgtcaa taactgggat   29580
aacttgggca tgtggtggtt ctccatagcg cttatgtttg tatgccttat tattatgtgg   29640
ctcatctgct gcctaaagcg caaacgcgcc cgaccaccca tctatagtcc catcattgtg   29700
ctacacccaa acaatgatgg aatccataga ttggacggac tgaaacacat gttcttttct   29760
cttacagtat gattaaatga gacatgattc ctcgagtttt tatattactg acccttgttg   29820
cgcttttttg tgcgtgctcc acattggctg cggtttctca catcgaagta gactgcattc   29880
cagccttcac agtctatttg ctttacggat tgtcacccct cacgctcatc tgcagcctca   29940
tcactgtggt catcgccttt atccagtgca ttgactgggt ctgtgtgcgc tttgcatatc   30000
tcagacacca tccccagtac agggacagga ctatagctga gcttcttaga attctttaat   30060
tatgaaattt actgtgactt ttctgctgat tatttgcacc ctatctgcgt tttgttcccc   30120
gacctccaag cctcaaagac atatatcatg cagattcact cgtatatgga atattccaag   30180
ttgctacaat gaaaaaagcg atcttttccga agcctggtta tatgcaatca tctctgttat   30240
ggtgttctgc agtaccatct tagccctagc tatatatccc taccttgaca ttggctggaa   30300
acgaatagat gccatgaacc acccaacttt ccccgcgccc gctatgcttc cactgcaaca   30360
agttgttgcc ggcggctttg tcccagccaa tcagcctcgc cccacttctc ccacccccac   30420
tgaaatcagc tactttaatc taacaggagg agatgactga caccctagat ctagaaatgg   30480
acggaattat tacagagcag cgcctgctag aaagacgcag ggcagcggcc gagcaacagc   30540
gcatgaatca agagctccaa gacatggtta acttgcacca gtgcaaaagg ggtatctttt   30600
gtctggtaaa gcaggccaaa gtcacctacg acagtaatac caccggacac cgccttagct   30660
acaagttgcc aaccaagcgt cagaaattgg tggtcatggt gggagaaaag cccattacca   30720
taactcagca ctcggtagaa accgaaggct gcattcactc accttgtcaa ggacctgagg   30780
atctctgcac ccttattaag accctgtgcg gtctcaaaga tcttattccc tttaactaat   30840
aaaaaaaaat aataaagcat cacttactta aaatcagtta gcaaatttct gtccagttta   30900
ttcagcagca cctccttgcc ctcctcccag ctctggtatt gcagcttcct cctggctgca   30960
aactttctcc acaatctaaa tggaatgtca gtttcctcct gttcctgtcc atccgcaccc   31020
actatcttca tgttgttgca gatgaagcgc gcaagaccgt ctgaagatac cttcaacccc   31080
gtgtatccat atgacacgga aaccggtcct ccaactgtgc ctttTcttac tcctcccttt   31140
```

```
gtatccccca atgggtttca agagagtccc cctggggtac tctctttgcg cctatccgaa    31200
cctctagtta cctccaatgg catgcttgcg ctcaaaatgg gcaacggcct ctctctggac    31260
gaggccggca accttacctc ccaaaatgta accactgtga gcccacctct caaaaaaacc    31320
aagtcaaaca taaacctgga aatatctgca cccctcacag ttacctcaga agccctaact    31380
gtggctgccg ccgcacctct aatggtcgcg ggcaacacac tcaccatgca atcacaggcc    31440
ccgctaaccg tgcacgactc caaacttagc attgccaccc aaggacccct cacagtgtca    31500
gaaggaaagc tagccctgca acatcaggc cccctcacca ccaccgatag cagtacccttt   31560
actatcactg cctcaccccc tctaactact gccactggta gcttgggcat tgacttgaaa    31620
gagcccattt atacacaaaa tggaaaacta ggactaaagt acggggctcc tttgcatgta    31680
acagacgacc taaacacttt gaccgtagca actggtccag gtgtgactat taataatact    31740
tccttgcaaa ctaaagttac tggagccttg ggttttgatt cacaaggcaa tatgcaactt    31800
aatgtagcag gaggactaag gattgattct caaaacagac gccttatact tgatgttagt    31860
tatccgtttg atgctcaaaa ccaactaaat ctaagactag acagggccc tcttttata    31920
aactcagccc acaacttgga tattaactac aacaaaggcc tttacttgtt tacagcttca    31980
aacaattcca aaaagcttga ggttaaccta agcactgcca aggggttgat gtttgacgct    32040
acagccatag ccattaatgc aggagatggg cttgaatttg gttcacctaa tgcaccaaac    32100
acaaatcccc tcaaaacaaa aattggccat ggcctagaat ttgattcaaa caaggctatg    32160
gttcctaaac taggaactgg ccttagtttt gacagcacag gtgccattac agtaggaaac    32220
aaaaataatg ataagctaac tttgtggacc acaccagctc catctcctaa ctgtagacta    32280
aatgcagaga aagatgctaa actcactttg gtcttaacaa aatgtggcag tcaaatactt    32340
gctacagttt cagttttggc tgttaaaggc agtttggctc caatatctgg aacagttcaa    32400
agtgctcatc ttattataag atttgacgaa aatggagtgc tactaaacaa ttccttcctg    32460
gacccagaat attggaactt tagaaatgga gatcttactg aaggcacagc ctatacaaac    32520
gctgttggat ttatgcctaa cctatcagct tatccaaaat ctcacggtaa aactgccaaa    32580
agtaacattg tcagtcaagt ttacttaaac ggagacaaaa ctaaacctgt aacactaacc    32640
attacactaa acggtacaca ggaaacagga gacacaactc caagtgcata ctctatgtca    32700
tttttcatggg actggtctgg ccacaactac attaatgaaa tatttgccac atcctcttac    32760
acttttcat acattgccca agaataaaga atcgtttgtg ttatgtttca acgtgtttat    32820
ttttcaattg cagaaaattt caagtcattt ttcattcagt agtatagccc caccaccaca    32880
tagcttatac agatcaccgt accttaatca aactcacaga accctagtat tcaacctgcc    32940
acctccctcc caacacacag agtacacagt cctttctccc cggctggcct taaaaagcat    33000
catatcatgg gtaacagaca tattcttagg tgttatattc cacacggttt cctgtcgagc    33060
caaacgctca tcagtgatat taataaactc cccgggcagc tcacttaagt tcatgtcgct    33120
gtccagctgc tgagccacag gctgctgtcc aacttgcggt tgcttaacgg gcggcgaagg    33180
agaagtccac gcctacatgg gggtagagtc ataatcgtgc atcaggatag ggcggtggtg    33240
ctgcagcagc gcgcgaataa actgctgccg ccgccgctcc gtcctgcagg aatacaacat    33300
ggcagtggtc tcctcagcga tgattcgcac cgcccgcagc ataaggcgcc ttgtcctccg    33360
ggcacagcag cgcaccctga tctcacttaa atcagcacag taactgcagc acagcaccac    33420
aatattgttc aaaatcccac agtgcaaggc gctgtatcca aagctcatgg cggggaccac    33480
agaacccacg tggccatcat accacaagcg caggtagatt aagtggcgac ccctcataaa    33540
```

```
cacgctggac ataaacatta cctcttttgg catgttgtaa ttcaccacct cccggtacca   33600
tataaacctc tgattaaaca tggcgccatc caccaccatc ctaaaccagc tggccaaaac   33660
ctgcccgccg gctatacact gcagggaacc gggactggaa caatgacagt ggagagccca   33720
ggactcgtaa ccatggatca tcatgctcgt catgatatca atgttggcac aacacaggca   33780
cacgtgcata cacttcctca ggattacaag ctcctcccgc gttagaacca tatcccaggg   33840
aacaacccat tcctgaatca gcgtaaatcc cacactgcag ggaagacctc gcacgtaact   33900
cacgttgtgc attgtcaaag tgttacattc gggcagcagc ggatgatcct ccagtatggt   33960
agcgcgggtt tctgtctcaa aaggaggtag acgatcccta ctgtacggag tgcgccgaga   34020
caaccgagat cgtgttggtc gtagtgtcat gccaaatgga acgccggacg tagtcatatt   34080
tcctgaagca aaaccaggtg cgggcgtgac aaacagatct gcgtctccgg tctcgccgct   34140
tagatcgctc tgtgtagtag ttgtagtata tccactctct caaagcatcc aggcgccccc   34200
tggcttcggg ttctatgtaa actccttcat gcgccgctgc cctgataaca tccaccaccg   34260
cagaataagc cacacccagc caacctacac attcgttctg cgagtcacac acggggaggag   34320 cgggaagagc tggaagaacc atgttttttt ttttattcca aaagattatc caaaacctca   34380
aaatgaagat ctattaagtg aacgcgctcc cctccggtgg cgtggtcaaa ctctacagcc   34440
aaagaacaga taatggcatt tgtaagatgt tgcacaatgg cttccaaaag gcaaacggcc   34500
ctcacgtcca agtggacgta aaggctaaac ccttcagggt gaatctcctc tataaacatt   34560
ccagcacctt caaccatgcc caaataattc tcatctcgcc accttctcaa tatatctcta   34620
agcaaatccc gaatattaag tccggccatt gtaaaaatct gctccagagc gccctccacc   34680
ttcagcctca agcagcgaat catgattgca aaaattcagg ttcctcacag acctgtataa   34740
gattcaaaag cggaacatta acaaaaatac cgcgatcccg taggtcccctt cgcagggcca   34800 gctgaacata atcgtgcagg tctgcacgga ccagcgcggc cacttccccg ccaggaacca   34860
tgacaaaaga acccacactg attatgacac gcatactcgg agctatgcta accagcgtag   34920
ccccgatgta agcttgttgc atgggcggcg atataaaatg caaggtgctg ctcaaaaaat   34980
caggcaaagc ctcgcgcaaa aaagaaagca catcgtagtc atgctcatgc agataaaggc   35040
aggtaagctc cggaaccacc acagaaaaag acaccatttt tctctcaaac atgtctgcgg   35100
gtttctgcat aaacacaaaa taaataacaa aaaaacatt taaacattag aagcctgtct   35160
tacaacagga aaacaaccc ttataagcat aagacggact acggccatgc cggcgtgacc   35220
gtaaaaaaac tggtcaccgt gattaaaaag caccaccgac agctcctcgg tcatgtccgg   35280
agtcataatg taagactcgg taaacacatc aggttgattc acatcggtca gtgctaaaaa   35340
gcgaccgaaa tagcccgggg gaatacatac ccgcaggcgt agagacaaca ttacagcccc   35400
cataggaggt ataacaaaat taataggaga gaaaaacaca taaacacctg aaaaaccctc   35460
ctgcctaggc aaaatagcac cctcccgctc cagaacaaca tacagcgctt ccacagcggc   35520
agccataaca gtcagcccta ccagtaaaaa agaaaaccta ttaaaaaaac accactcgac   35580
acggcaccag ctcaatcagt cacagtgtaa aaaagggcca agtgcagagc gagtatatat   35640
aggactaaaa aatgacgtaa cggttaaagt ccacaaaaaa cacccagaaa accgcacgcg   35700
aacctacgcc cagaaacgaa agccaaaaaa cccacaactt cctcaaatcg tcacttccgt   35760
tttcccacgt tacgtaactt cccatttta gaaaactaca attcccaaca catacaagtt   35820
actccgccct aaaacctacg tcacccgccc cgttcccacg ccccgcgcca cgtcacaaac   35880
```
tccaccccct cattatcata ttggcttcaa tccaaaataa ggtatattat tgatgatg    35938

<210> SEQ ID NO 42
<211> LENGTH: 160
<212> TYPE: PRT
<213> ORGANISM: Adenovirus

<400> SEQUENCE: 42

Met Glu Arg Arg Asn Pro Ser Glu Arg Gly Val Pro Ala Gly Phe Ser
1               5                   10                  15

Gly His Ala Phe Val Glu Ser Gly Gly Glu Thr Gln Glu Ser Pro Thr
            20                  25                  30

Thr Val Val Phe Arg Pro Pro Gly Asn Asn Thr Asp Gly Gly Ala Ala
        35                  40                  45

Ala Ala Thr Ala Ala Ala Gly Gly Ser Gln Ala Ala Ala Ala Ala Gly
    50                  55                  60

Ala Glu Pro Met Glu Pro Glu Ser Arg Pro Gly Pro Ser Gly Met Asn
65                  70                  75                  80

Val Val Gln Pro Glu Ser Met Ser Lys Val Asn Leu Asn Gly Val Phe
                85                  90                  95

Asp Met Thr Met Lys Ile Trp Lys Val Leu Arg Tyr Asp Glu Thr Arg
            100                 105                 110

Thr Arg Cys Arg Pro Cys Glu Cys Gly Gly Lys His Ile Arg Asn Gln
        115                 120                 125

Pro Val Met Leu Asp Val Thr Glu Glu Leu Arg Pro Asp His Leu Val
    130                 135                 140

Leu Ala Cys Thr Arg Ala Glu Phe Gly Ser Ser Asp Glu Asp Thr Asp
145                 150                 155                 160

<210> SEQ ID NO 43
<211> LENGTH: 155
<212> TYPE: PRT
<213> ORGANISM: Adenovirus

<400> SEQUENCE: 43

Met Glu Arg Arg Asn Pro Ser Glu Arg Gly Val Pro Ala Gly Phe Ser
1               5                   10                  15

Gly His Ala Ser Val Glu Ser Gly Gly Glu Thr Gln Glu Ser Pro Ala
            20                  25                  30

Thr Val Val Phe Arg Pro Pro Gly Asn Asn Thr Asp Gly Gly Ala Thr
        35                  40                  45

Ala Gly Gly Ser Gln Ala Ala Ala Ala Gly Ala Glu Pro Met Glu
    50                  55                  60

Pro Glu Ser Arg Pro Gly Pro Ser Gly Met Asn Val Val Gln Pro Glu
65                  70                  75                  80

Ser Met Ser Lys Val Asn Leu Asn Gly Val Phe Asp Met Thr Met Lys
                85                  90                  95

Ile Trp Lys Val Leu Arg Tyr Asp Glu Thr Arg Thr Arg Cys Arg Pro
            100                 105                 110

Cys Glu Cys Gly Gly Lys His Ile Arg Asn Gln Pro Val Met Leu Asp
        115                 120                 125

Val Thr Glu Glu Leu Arg Pro Asp His Leu Val Leu Ala Cys Thr Arg
    130                 135                 140

Ala Glu Phe Gly Ser Ser Asp Glu Asp Thr Asp
145                 150                 155

<210> SEQ ID NO 44
<211> LENGTH: 155
<212> TYPE: PRT
<213> ORGANISM: Adenovirus

<400> SEQUENCE: 44

Met Glu Arg Arg Asn Pro Ser Glu Arg Gly Val Pro Ala Gly Phe Ser
1               5                   10                  15

Gly His Ala Ser Val Glu Ser Gly Gly Glu Thr Gln Glu Ser Pro Ala
            20                  25                  30

Thr Val Val Phe Arg Pro Pro Gly Asn Asn Thr Asp Gly Gly Ala Thr
        35                  40                  45

Ala Gly Gly Ser Gln Ala Ala Ala Ala Gly Ala Glu Pro Met Glu
    50                  55                  60

Pro Glu Ser Arg Pro Gly Pro Ser Gly Met Asn Val Val Gln Pro Glu
65                  70                  75                  80

Ser Met Ser Lys Val Asn Leu Asn Gly Val Phe Asp Met Thr Met Lys
                85                  90                  95

Ile Trp Lys Val Leu Arg Tyr Asp Glu Thr Arg Thr Arg Cys Arg Pro
            100                 105                 110

Cys Glu Cys Gly Gly Lys His Ile Arg Asn Gln Pro Val Met Leu Asp
        115                 120                 125

Val Thr Glu Glu Leu Arg Pro Asp His Leu Val Leu Ala Cys Thr Arg
    130                 135                 140

Ala Glu Phe Gly Ser Ser Asp Glu Asp Thr Asp
145                 150                 155

<210> SEQ ID NO 45
<211> LENGTH: 127
<212> TYPE: PRT
<213> ORGANISM: Adenovirus

<400> SEQUENCE: 45

Met Glu Ser Arg Asn Pro Phe Gln Gln Gly Leu Pro Ala Gly Phe Leu
1               5                   10                  15

Ser Ser Ser Phe Val Glu Asn Met Glu Val Pro Ala Pro Glu Cys Asn
            20                  25                  30

Leu Arg Leu Leu Ala Gly Thr Ala Ala Arg His Ser Glu Asp Pro Glu
        35                  40                  45

Ser Pro Ala Ala Gly Gly Ser Arg Arg Glu Ser Glu Ser Arg Pro Gly
    50                  55                  60

Pro Ser Gly Gly Gly Val Ala Asp Leu Phe Pro Glu Leu His Arg Thr
65                  70                  75                  80

Arg Cys Arg Ala Cys Glu Cys Gly Gly Lys His Ala Arg Phe Gln Pro
                85                  90                  95

Val Cys Val Asp Val Thr Glu Asp Leu Arg Pro Asp His Leu Val Leu
            100                 105                 110

Ser Cys Thr Gly Thr Glu Phe Gly Ser Ser Gly Glu Glu Ser Asp
        115                 120                 125

<210> SEQ ID NO 46
<211> LENGTH: 144
<212> TYPE: PRT
<213> ORGANISM: Adenovirus

<400> SEQUENCE: 46

Met Asp Pro Ala Asp Ser Phe Gln Gln Gly Ile Arg Phe Gly Phe His
1               5                   10                  15

```
Ser His Ser Ile Val Glu Asn Met Glu Gly Ser Gln Asp Glu Asp Asn
            20                  25                  30

Leu Arg Leu Leu Ala Ser Ala Ala Phe Gly Cys Ser Gly Asn Pro Glu
        35                  40                  45

Ala Ser Thr Gly His Ala Ser Gly Ser Gly Gly Gly Thr Ala Arg Gly
    50                  55                  60

Gln Pro Glu Ser Arg Pro Gly Pro Ser Ser Gly Gly Gly Gly Val Ala
65                  70                  75                  80

Asp Leu Ser Pro Glu Leu Gln Arg Ile Leu Arg Tyr Asp Asp Thr Arg
                85                  90                  95

Ser Arg Val Arg Ala Cys Glu Cys Gly Gly Lys His Ala Arg Phe Gln
            100                 105                 110

Pro Val Cys Val Asp Val Thr Glu Asp Leu Arg Pro Asp His Leu Val
        115                 120                 125

Ile Ala Arg Thr Gly Ala Glu Phe Gly Ser Ser Gly Glu Glu Thr Asp
        130                 135                 140
```

ONCOLYTIC ADENOVIRUSES WITH INCREASED PROPORTION OF THE 156R SPLICING ISOFORM OF THE E1B PROTEIN

CROSS-REFERENCES TO RELATED APPLICATIONS

This application is a continuation of U.S. application Ser. No. 14/648,661, filed May 29, 2015, which is a U.S. 371 of the International Application No. PCT/GB2013/053177, filed Nov. 29, 2013, which claims the benefit of United Kingdom Application No. 1221590.1, filed Nov. 30, 2012, the full benefit of which are incorporated by reference in their entirety for all purposes.

REFERENCE TO A "SEQUENCE LISTING" SUBMITTED AS ASCII TEXT FILES VIA EFS WEB

The Sequence Listing written in file SequenceListing-098319-1094116.txt created on Jul. 6, 2018, 70,037 bytes, machine format IBM-PC, MS-Windows operating system, in accordance with 37 C.F.R. §§ 1.821- to 1.825, is hereby incorporated by reference in its entirety for all purposes.

TECHNICAL FIELD

This invention relates to oncolytic adenoviruses and their use in treating neoplastic disease. More particularly, the invention relates to mutations of the E1B gene that modulate the levels of splicing isoforms of this gene, thereby improving the therapeutic index of the oncolytic adenovirus.

BACKGROUND TO THE INVENTION

Oncolytic Viruses

Oncolytic virotherapy is an emerging treatment platform for cancer therapy. Oncolytic viruses are viruses that selectively replicate in cancer cells that possess specific oncogenic phenotypes, thereby killing cancer cells whilst sparing normal cells. Initial research focused on naturally-occurring non-pathogenic viruses, however, these studies were of limited success. Although tumour growth was observed to slow down and normal tissue was not damaged, there was no alteration in the course of the disease.

Recent studies have therefore focused on engineering recombinant viruses that selectively target cancer cells. One example of this class of engineered viruses is adenoviruses that are mutated in the E1B region of the viral genome.

Adenoviral E1B and p53

One function of the mammalian tumour suppressor protein p53 is to mediate cell-cycle arrest and/or apoptosis in response to DNA damage or foreign DNA synthesis. Consequently, some viruses, such as adenovirus, encode proteins that inactivate p53 in infected cells to allow efficient viral replication. One of these proteins, the 55 kiloDalton protein from the E1B region of adenovirus (E1B-55K or E1B-496R), binds to p53 so causing a substantial loss of p53. This consequently prevents p53-mediated apoptosis of the infected cell. E1B-496R is therefore essential for adenoviral replication in cells containing functional p53.

Human tumour cells are frequently homozygous or heterozygous for mutated (e.g. substitution, deletion, frameshift mutated) p53 alleles, and lack p53 function necessary for normal control of the cell cycle (Hollstein et. al (1991) *Science* 253:49; Levine et al. (1991) Nature; 351(6326):453-6). Many neoplastic cells are therefore p53$^{(-)}$ either because they lack sufficient levels of p53 and/or because they express mutant forms of p53 which are incapable of substantial p53 function.

E1B Mutated Adenoviruses

Oncolytic adenoviruses have been engineered that take advantage of the difference in p53 functionality between neoplastic and normal cells. By mutating the E1B-496R protein to remove binding interactions with p53 or by making various deletions within the E1B locus (see, for example, U.S. Pat. No. 5,677,178), the resulting adenoviruses can replicate and ultimately lyse cancer cells that substantially lack p53 function, but not in cells that possess normal p53 function.

One example is ONYX-015 (originally named d11520 and also referred to as H101), a mutant adenovirus that does not express the E1B-496R protein (Heise et al. (1997) *Nat. Med.* 3 (6): 639-645). The virus contains a stop codon immediately following the translation start codon and also has a large deletion of the E1B-496R coding sequence. As a result this virus lacks the ability to bind and inactivate p53, and thus can only replicate efficiently in cells defective in p53 function, such as neoplastic cells and tumours. Unfortunately, E1B-496R carries out other functions in addition to binding and inactivating p53 (Eager et al. (2001) *Cancer Gene Ther.* 18 (5): 305-317). Consequently, the ONYX-015 virus is defective in cytoplasmic accumulation of the viral late mRNAs, host cell shut-off and translation of late mRNAs. Thus, the mutation in ONYX-015 compromises the ability of the mutant virus to reproduce itself in tumour cells. An additional problem is that large deletions destabilise the viral genome.

Additional examples are ONYX-051 and ONYX-053, mutant adenoviruses that contain point mutations (R240A and H260A, respectively) in the E1B-496R protein that prevent its binding to p53. These mutations enable the virus to replicate selectively in cells that are deficient in p53 function, without compromising the ability of the virus to replicate in these cells (Shen et al. (2001) *J. Virol.* 75 (9): 4297-4307 and U.S. Pat. No. 7,785,887).

However, there remains a great need for improved mutant viruses whose oncolytic ability has been enhanced and which are useful in the therapy of cancer.

DISCLOSURE OF INVENTION

It has now been found by the present inventor that by modulating the level and type of splice isoforms of the E1B gene product, expressed from the E1B gene, the oncolytic activity of such viruses can be enhanced. Accordingly, a first aspect of the present invention provides a recombinant adenovirus in which the proportion of the E1B-156R isoform is increased relative to wild-type levels, wherein the adenovirus has an oncolytic effect in a cancer cell. The recombinant adenovirus may carry a mutation such that the proportion of the E1B-156R isoform is increased relative to wild-type levels, so that the adenovirus has an oncolytic effect in a cancer cell. The mutation may be in the sequence of the E1B gene of the adenovirus. A virus according to the invention is therefore replication-inhibited in non-neoplastic cells but is capable of expressing a replication phenotype in neoplastic cells, including neoplastic cells that substantially lack functional p53.

In the specific examples of adenoviruses described herein, over-expression of E1B-156R is thought to be an imbalance caused by a mutated 93R splice site in the E1B gene of the adenovirus. 156R is able to complement some of the 496R function, but not the ones essential to oncoselectivity. In contrast to prior art viruses of similar type, viruses according to the present invention include a functional E3B region for better in vivo efficacy. For example, Onyx-015 lacks E3B. Indeed, Onyx-015 virus and its selectivity is by far outperformed by viruses according to the invention, in all respects. Furthermore, the inventor has tested viruses prepared in accordance with the invention in normal cells and the results show that the viruses have an outstanding safety profile, especially in comparison to the known virus Onyx-015.

Herein, the term "replication-inhibited virus" or "replication-defective" refers to a virus that preferentially inhibits cell proliferation or induces apoptosis in a predetermined cell population that is transformed into a cancerous or neoplastic state. Such a virus is substantially unable to inhibit cell proliferation, induce apoptosis, or express a replication phenotype in cells comprising normal p53 function levels that are characteristic of non-replicating, non-transformed cells. Such transformed cells may substantially lack p53 function, which supports expression of a virus replication phenotype. However, selectivity of viruses according to the invention for neoplastic tissue might well be more general than just for p53 status; the transformed state as such might be the basis for selection. For example, it has been suggested that oncolytic selectivity observed with the ONYX-015 virus may be due to the capacity of some cancer cell lines to support late viral RNA export from the nucleus, a function which is lost in ONYX-015 in normal cells due to the E1B-496R deletion. A similar mechanism may operate in the recombinant adenoviruses of the present invention, which have reduced levels of E1B-496R protein. It is not as yet clear exactly how an increase in the levels of E1B-156R in the recombinant adenoviruses of the present invention results in oncolytic selectivity.

Typically, a replication-inhibited virus according to the invention exhibits a substantial decrease in plaquing efficiency on cells comprising normal p53 function (for a suitable assay, see Wang, Y., G. Hallden, et al. (2003). "E3 gene manipulations affect oncolytic adenovirus activity in immunocompetent tumor models." Nature biotechnology 21(11): 1328-1335). Another example of a suitable assay that may be used is a cytotoxicity assay to measure loss of viable cells, using for example a tetrazolium dye such as MTT, XTT, MTS or a WST (see Berridge et al., Biotechnology Annual Review, 11: 127-152 (2005).

As used herein, the term "replication phenotype" refers to one or more of the following phenotypic characteristics of cells infected with a virus such as a replication-inhibited adenovirus: (1) substantial expression of late gene products, such as capsid proteins (e.g., adenoviral penton base polypeptide) or RNA transcripts initiated from viral late gene promoter(s); (2) replication of viral genomes or formation of replicative intermediates; (3) assembly of viral capsids or packaged virion particles; (4) appearance of cytopathic effect (CPE) in the infected cell; (5) completion of a viral lytic cycle; and (6) other phenotypic alterations which are typically contingent upon abrogation of p53 function in non-neoplastic cells infected with a wild-type replication-competent DNA virus encoding functional oncoprotein(s). A replication phenotype according to the present invention comprises at least one of the phenotypic characteristics listed above, preferably more than one of the phenotypic characteristics, such as 2, 3, 4, 5, 6 or more characteristics.

Techniques for the measurement of these phenotypes will be known to those of skill in the art. For example, methods to assess appearance of CPE are described in the examples herein, and evaluated using 50% tissue culture infective dose ($TCID_{50}$) and number of plaque-forming units (pfu)/cell (cell count on the day of infection).

The term "neoplastic cells" refers to cells which exhibit relatively autonomous growth, so that they exhibit an aberrant growth phenotype characterised by a significant loss of control of cell proliferation. Neoplastic cells comprise cells which may be actively replicating or in a temporary non-replicative resting state (G1 or G0); similarly, neoplastic cells may comprise cells that have a well-differentiated phenotype, a poorly differentiated phenotype, or a mixture of both types of cells. Thus, not all neoplastic cells are necessarily replicating cells at a given time point. The set of cells defined herein as neoplastic cells consists of cells in benign neoplasms and cells in malignant (or frank) neoplasms. Frankly neoplastic cells are frequently referred to as cancerous, typically carcinoma if originating from cells of endodermal or ectodermal histological origin, or sarcoma if originating from cells types derived from mesoderm. The terms neoplastic cell and cancer cell are used interchangeably herein.

Herein, the term "p53 function" refers to the property of having an essentially normal level of a polypeptide encoded by the p53 gene (i.e. relative to non-neoplastic cells of the same histological type), wherein the p53 polypeptide is capable of binding to wild-type adenovirus E1B-496R polypeptide. For example, p53 function may be lost by production of an inactive (i.e. mutant) form of p53 or by substantial decrease or total loss of expression of p53 polypeptide. p53 function may also be substantially absent in neoplastic cells that comprise p53 alleles that encode wild-type polypeptide; for example, a genetic alteration outside of the p53 locus, such as mutations that result in aberrant subcellular processing or localisation of p53 (e.g. a mutation resulting in localisation of p53 predominantly in the cytoplasm rather than the nucleus) can result in loss of p53 function. Many neoplastic cells are therefore $p53^{(-)}$ either because they lack sufficient levels of p53 and/or because they express mutant forms of p53 which are incapable of substantial p53 function. In the context to the present invention, the key function of p53 is the ability to mediate cell-cycle arrest and/or mediate apoptosis in response to DNA damage or foreign DNA synthesis. Neoplastic cells lack functional p53, if the said reduction in p53 function prevents normal control of the cell cycle and apoptosis. This may consist a decrease of 2-fold, 5-fold, 10-fold, 20-fold, 50-fold, 100-fold or more of correctly processed, localised and expressed p53 that can bind to E1B-496R, compared to the corresponding non-neoplastic cells of the same type. These cells are therefore termed "$p53^{(-)}$".

It is believed that replication-deficient adenovirus species which lack the capacity to complex p53 but substantially retain other essential viral replicative functions will exhibit a replication phenotype in cells which are deficient in p53 function (e.g., cells which are homozygous for substantially deleted p53 alleles, or cells which comprise mutant p53 proteins which are essentially non-functional) but will not substantially exhibit a replicative phenotype in non-replicating, non-neoplastic cells. Such replication inhibited adenovirus species are referred to herein for convenience as E1B-$p53^{(-)}$ replication-deficient adenoviruses.

An "oncolytic virus" is a virus that preferentially infects and lyses cancer cells. Oncolytic effect is seen when comparing efficacy in cancer cells versus normal cells. A virus is considered oncolytic if the ratio of lysed cancer cells to non-cancerous cells is 2:1, 4:1, 10:1, 20:1, 50:1, 100:1 or more. Preferably, a virus is identified as oncolytic by assessing the oncolytic index (see below). Herein, the oncolytic effect comprises a) viral infection of cells; b) selective replication of the viral genome in (p53 function-deficient) cancer cells leading to preferential virus-mediated cell lysis in cancer cells (which may be p53 deficient), and the release of viral particles for further infection events. The oncolytic effect can be measured using various assays. In these assays a control virus should be used, often the wild type/naturally occurring version. As such any of the following examples of assays can be used: MTS (cytotoxicity), $TCID_{50}$ (replication competency), LDH assays (lactate dehydrogenase (LDH) is a stable enzyme, present in all cell types, and is rapidly released into the cell culture medium upon damage of the plasma membrane), FACS (cell sorting), western blot, and QPCR (late gene expression or genome copy number). Other examples will be clear to those of skill in the art.

An advantage of a virus according to the present invention is that such a virus has minimal genetic aberrations. Preferably, a virus according to the invention will be mutated in its genetic sequence, such as in the form of point mutations (including insertions, deletions, additions, and substitutions); point mutations are better for the health of the virus. Larger changes put an evolutionary strain on the virus. Additionally, genomic size and integrity can be important.

A virus according to the present invention has a cancer selection index or oncolytic index (the two terms are interchangeable) that is much improved in comparison to existing oncolytic viruses that are available, such as the H101 virus. This refers to the replication capacity in normal cells in comparison to cancer cells, which may be expressed according to the following equation:

$$(OVc/OVn)/(WTc/WTn)=\text{Cancer selection index}$$

wherein OV=Oncolytic virus replication capacity; WT is Control virus replication capacity; c is cancer cells; n is normal cells.

A virus according to the invention may have a cancer selection index of between 2 and 10,000, depending on the type of cell, preferably between 5 and 5000, 10 and 1000, or 50 and 500. In the case of a representative example of a virus according to the invention, Ixovex, this virus exhibits a cancer selection index versus control of 3.5 in HeLa cells; 14 in A549 cells; 2000 in H1299 cells and 450 in H460 cells. In the same cell types, the values for the Onyx-015 virus versus Ixo-ctrl are HeLa=0.1x; A549=0.1x; H1299=0.05x; and H460=0.004x.

As such, it is possible to apply a virus according to the invention to the majority of tumour types. One theory is that the oncolytic viruses of the invention are selective for p53 negative status and quickly-replicating cells.

In addition, a virus according to the invention will be met by the host immune defence and ultimately cleared, this before the complete tumour eradication. This does not only present itself as a way of removing the virus, so negating any possible liver toxicity as a result of a viral overload, but also provides the chance to induce an anticancer immune response in the host since the immune system will be alerted to the viral presence in the tumour.

Adenoviruses

A virus according to the invention is a recombinant adenovirus. At the time of writing, there are more than 65 described serotypes in humans (HAdV-1 to 65) distributed across seven species (Human adenovirus A to G) and as many from other mammals and birds (see Strauss, "Adenovirus infections in humans," in *The Adenoviruses* (1984) ed. Ginsberg, pp. 451-596 Plenum Press, New York. For a general description of adenovirus biology see *Virology*, Second Edition, eds. Fields and Knipe. Vol. 2, pp 1651-1740, Raven Press, New York). The term "adenovirus" as used herein, encompasses any one of these adenovirus species. Preferably, an adenovirus according to the invention is a human adenovirus of subfamily group C, namely one of serotypes 1, 2, 5, 6, or 57. More preferably, the term adenovirus applies to two human serotypes, Ad2 and Ad5.

In one preferred embodiment of the invention, the adenovirus is adenovirus serotype Ad5. The adenovirus may be adenovirus serotype Ad5 strain pTG3602. Strain pTG3602 has approximately 15 point mutations scattered throughout the 35,000 nucleotide adenovirus genome, however none of these mutations fall within the E1B gene. Herein, adenovirus type 5 provides a common reference point for the nucleotide numbering convention of viral polynucleotides and amino acid numbering of viral-encoded polypeptides the E1B viral gene region. Those skilled in the art will readily identify the corresponding positions in other adenoviral serotypes. Herein, the term "recombinant" indicates that a polynucleotide construct (e.g. and adenovirus genome) has been generated, in part, by intentional modification by man.

E1B Gene

A virus according to the invention preferably carries a mutation in the sequence of the E1B gene. All serotypes encode a gene that is referred to across serotypes as early region 1B (E1B), encoding gene products of the early phase of DNA replication. Herein, the "E1B gene" refers to the full length transcription unit of the E1B gene in any adenovirus, preferably human adenovirus. A representative example of an E1B gene is that from adenovirus type 5 (Ad5) which has the polynucleotide sequence according to SEQ ID NO: 1. Other examples will be known to the skilled reader and details can be found in commonly used databases, such as, for example Entrez Gene (www.ncbi.nlm.nih.gov/gene). In human adenovirus type 5, the E1B coding region starts at genomic nucleotide number 1714 and ends at the E1B polyA site at genomic nucleotide number 4043. Similar regions are present in all adenoviruses so far tested, for example, including species as diverse as sheep, snake and even bat adenovirus.

The E1B transcription unit of the human adenovirus encodes at least five different splicing isoforms (see FIG. 2) (Takayesu et al. (1994) *J. Gen. Virol.* 75:789-798). Again, giving the example of Ad5, the major 2.28 kb E1B precursor mRNA encodes two overlapping reading frames, one for the 176 residue E1B-19K protein (E1B-176R) and the other for E1B-55K protein (496 residues; E1B-496R). The E1B-156R, E1B-93R, E1B-84R isoforms (named after the number of amino acids in the expressed product) are generated by alternative splicing of the precursor mRNA for E1B-496R, between a common splice donor (SD1) and one of three splice acceptor sites (SA1-3). The resulting mRNAs encode the 79 amino acids of the E1B-496R N-terminus, and whilst E1B-93R and E1B-84R have unique C-termini, E1B-156R is completed by the 77 C-terminal residues of E1B-496R. Alternative splicing is explained in n, 0., P. Convertini, et al. (2012). "Function of alternative splicing." Gene. It will be apparent to the skilled person that the E1B isoforms in other adenovirus serotypes may have slightly different lengths to those discussed above for Ad5 (e.g. the equivalent of E1B-156R in Ad2 is 155 amino acids long and is therefore often referred to as 155R). Herein, the isoform names E1B-156R, E1B-93R, E1B-84R, E1B-176R and E1B-496R refer to the equivalent isoform of the same approximate size in all adenoviruses, regardless of the actual number of amino acids in the equivalent isoform.

It has been confirmed that the E1B-156R isoform exists in a wide cross-section of adenovirus variants, by using PCR to amplify the specific cDNAs for E1B-156R using start and stop primers specific for each respective E1B-55k gene (FIG. 14). Our experiments show similar splicing patterns in representative viruses from each of the different genera (A-Ad12, B1-Ad3, B2-Ad11, C-Ad5, D-Ad37, E-Ad4 and F-Ad40). Indeed, Ad1wt and Ad57wt have identical E1B-156R protein sequences; Ad2wt and Ad1wt also have identical sequences; and Ad5wt differs only slightly from them all. This makes only three different E1B-156R protein sequences in the entire subfamily C differing at a total of five single amino acid positions and in the length of an internal poly-alanine stretch. Thus it is fully expected that the results demonstrated herein in serotypes Ad2 and Ad5 will be mirrored across other adenovirus variants.

A number of complementation experiments have been performed to show that an increase in E1B-156R is responsible (at least in part) for the increase in Oncolytic Index (OI) that has been observed, such that overexpression of the Ad5-156R gives a potent increase in the OI of adenoviruses generally. In FIGS. 11A, 11B and 11C and FIG. 12 herein, it is shown that adenovirus type 5 E1B-156R is a potent enhancer of the OI in the subfamily group C. Furthermore, the E1B-156R equivalent from Ad2wt was shown to have a positive effect on the OI of Ad5wt, meaning that the effect appears not to be limited to one particular adenovirus serotype.

Herein, the E1B-156R isoform of human Ad5 has the polynucleotide sequence according to SEQ ID NO: 2 and the polypeptide sequence according to SEQ ID NO: 3. Herein, the 496R isoform has the polynucleotide sequence according to SEQ ID NO: 4 and a polypeptide sequence according to SEQ ID NO: 5. Herein, the E1B-93R isoform has the polynucleotide sequence according to SEQ ID NO: 6. and the polypeptide sequence according to SEQ ID NO: 7. Herein, the E1B-84R isoform has the polynucleotide sequence according to SEQ ID NO: 8 and the polypeptide sequence according to SEQ ID NO: 9. It will be appreciated by the skilled reader that a degree of variation in sequence exists in naturally-occurring viral variants; accordingly, the invention embraces isoform sequences that differ from the specific sequences set out in the reference sequences referred to about, but are 80%, 85%, 90%, 95%, 98%, 99% or more homologous or identical to those sequences, as calculated by common sequence alignment programs, for example, BLAST (blast.ncbi.nlm.nig.gov/Blast.cgi) which can be nucleotide BLAST (blastn) or protein BLAST (blastp). Two sequences are said to be "homologous", as the term is used herein, if one of the sequences has a high enough degree of identity or similarity to the other sequence. "Identity" indicates that at any particular position in the aligned sequences, the nucleotide is identical between the sequences. "Similarity" indicates that, at any particular position in aligned polypeptide sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Accordingly, embodiments of the invention include variant recombinant adenoviruses where the E1B-156R isoform has a polynucleotide sequence that has at least 80% sequence identity to SEQ ID NO: 2 and a polypeptide sequence that has at least 80% sequence identity to SEQ ID NO: 3; where the E1B-496R isoform has a polynucleotide sequence that has at least 80% sequence identity to SEQ ID NO: 4 and a polypeptide sequence that has at least 80% sequence identity to SEQ ID NO: 5; where the E1B-93R isoform has a polynucleotide sequence that has at least 80% sequence identity to SEQ ID NO: 6 and a polypeptide sequence that has at least 80% sequence identity to SEQ ID NO: 7; and where the E1B-84R isoform has a polynucleotide sequence that has at least 80% sequence identity to SEQ ID NO: 8 and a polypeptide sequence that has at least 80% sequence identity to SEQ ID NO: 9. Representative examples of variant E1B-156R isoform sequences are given herein (FIG. 13). Included equivalent sequences to Ad5 E1B-156R are those with 80%, 85%, 90%, 95%, 98%, 99% or more identity with those sequences provided in FIG. 13 (as described above for Ad5). Modulation of isoform levels by engineering.

According to the invention, the level and/or type of splice isoforms of the E1B gene product, expressed from the E1B gene, is modified, and as a result the viruses are rendered oncolytic. The levels and/or types of E1B isoforms may be modulated by any means, for example using ribozymes designed to specifically cleave the E1B isoform mRNAs at selected positions and thereby preventing translation of the mRNAs into functional polypeptide. Alternative methods will be apparent to those of skill in the art, and include insertion of multiple copies of the E1B gene sequence, or forms that encode E1B-156R; activation of regulation of E1B gene expression, or forms that encode E1B-156R, for example by modulation of promoter or enhancer sequences; insertion of regulatory sequences, and so on.

Herein, we provide as particular examples of variant adenoviruses according to the invention, adenoviruses that include one or more mutations in the splicing regions of E1B gene that achieve this effect. As splice site recognition by the spliceosome is known to be affected by mRNA secondary structure, mutations in the E1B gene that affect the secondary structure of its mRNA may also modulate the levels and types of E1B isoforms. For example, the mutation may remove a splice site by changing the polynucleotide and polypeptide sequence of the E1B gene; or may remove a splice site by changing the polynucleotide sequence of the E1B gene and retaining the original polypeptide sequence.

In one embodiment, this effect may be achieved when the E1B gene is mutated in one or more of the splicing recognition regions comprising: a) the splice donor site 1 (SD1); the E1B-93R splice acceptor (SA1); c) E1B-156R splice acceptor (SA2); d) E1B-84R splice acceptor (SA3); and/or e) splice donor site 2 (SD2).

In the example case of Ad5, these splice sites are at the following positions and have the following sequences: SD1 has the sequence GTGGC at position 2251-2255 of the Ad5 genome (position 2256-2260 of the Ad5 genome accession number AC_000008.1 (SEQ ID NO: 41) and position 543-547 in the E1B gene (SEQ ID NO: 1)). The E1B-93R splice acceptor (SA1) has the sequence AACAG at position 3218-3222 of the Ad5 genome (position 3213-3217 of the Ad5 genome accession number AC_000008.1 (SEQ ID NO: 41) and position 1500-1504 in the E1B gene (SEQ ID NO: 1)). The E1B-156R splice acceptor (SA2) has the sequence TTGAG at position 3276-3280 of the Ad5 genome (position 3271-3275 of the Ad5 genome accession number AC_000008.1 (SEQ ID NO: 41) and position 1558-1562 in the E1B gene (SEQ ID NO: 1)). The E1B-84R splice acceptor (SA3) has the sequence TGCAG at position 3595-

3599 of the Ad5 genome (position 3590-3594 of the Ad5 genome accession number AC_000008.1 (SEQ ID NO: 41) and position 1877-1881 in the E1B gene (SEQ ID NO: 1)). The splice donor site 2 (SD2) has the sequence GTACT at position 3506-3510 of the Ad5 genome (position 3511-3515 of the Ad5 genome accession number AC_000008.1 (SEQ ID NO: 41) and position 1798-1802 in the E1B gene (SEQ ID NO: 1)). Equivalent sites at equivalent positions in other human serotypes will be easily apparent to those of skill in the art, imbued with the teaching of the present invention.

Accordingly, one aspect of the present invention is a recombinant adenovirus in which where the E1B gene splicing recognition regions are mutated at one or more of the following positions in the Ad5 genome: a) nucleotide 3216 of the adenovirus Ad5 genome (accession number AC_000008.1) (SEQ ID NO: 41) (position 1503 in the E1B gene (SEQ ID NO: 1); b) nucleotide 3218 of the adenovirus Ad5 genome (accession number AC_000008.1) (SEQ ID NO: 41) (position 1505 in the E1B gene (SEQ ID NO: 1); and/or c) nucleotide 3221 of the adenovirus Ad5 genome (accession number AC_000008.1) (SEQ ID NO: 41) (position 1508 in the E1B gene (SEQ ID NO: 1). The E1B gene may contain one or more of the following mutations: a) A3216G in the adenovirus Ad5 genome (position 1503 in the E1B gene (SEQ ID NO: 1));

b) G3218A in the adenovirus Ad5 genome (position 1505 in the E1B gene (SEQ ID NO: 1)); and/or c) G3221A in the adenovirus Ad5 genome (position 1508 in the E1B gene (SEQ ID NO: 1)). Herein, the positions of all point mutations are numbered according to Ad5 genome accession number AC_000008.1 (SEQ ID NO: 41).

The table below identifies the sequences and positions of the splicing recognition regions of the E1B gene in the Ad5 genome. "Ad 5 genome position" and "E1B gene position" correspond to the five residues immediately upstream of splice donor sites (SD1 and SD2), and immediately downstream of splice acceptor sites (SA1, SA2 and SA3).

Mutation of the viral sequence within the splicing recognition regions of the E1B gene can involve either a) removing a splice site by changing the polynucleotide and polypeptide sequence of the E1B gene; or b) removing a splice site by changing the polynucleotide sequence of the E1B gene and retaining the original polypeptide sequence. As the skilled person will appreciate, there is redundancy in the genetic code, i.e. some amino acids are encoded by multiple codons. The splice site sequences can be removed from the transcribed E1B mRNA by mutating the corresponding adenoviral DNA to use (an) alternative codon(s) for the amino acids the polynucleotide sequence is encoding at these sites. Thus, the resulting translated protein will preferably not contain any amino acid changes. The codon table below shows the redundancy in the genetic code.

| Amino Acids | | | Codons |
|---|---|---|---|
| Alanine | Ala | A | GCA GCC GCG GCU |
| Arginine | Arg | R | AGA AGG CGA CGC CGG CGU |
| Aspartic acid | Asp | D | GAC GAU |
| Asparagine | Asn | N | AAC AAU |
| Cysteine | Cys | C | UGC UGU |
| Glutamic acid | Glu | E | GAA GAG |
| Glutamine | Gln | Q | CAA CAG |
| Glycine | Gly | G | GGA GGC GGG GGU |
| Histidine | His | H | CAC CAU |
| Isoleucine | Ile | I | AUA AUC AUU |
| Leucine | Leu | L | CUA CUC CUG CUU UUA UUG |
| Lysine | Lys | K | AAA AAG |
| Methionine | Met | M | AUG |

| E1B splice sites | Ad5 genome position | E1B gene position | Sequence | SEQ ID NO: |
|---|---|---|---|---|
| splice donor 1 (SD1) | 2251-2255 | 538-542 | cag/GTGGCTGAAC | SEQ ID NO: 10 |
| E1B-93R splice acceptor (SA1) | 3218-3222 | 1505-1509 | TCCTTGCATTTGGGTAACAG/gag | SEQ ID NO: 11 |
| E1B-156R splice acceptor (SA2) | 3276-3280 | 1563-1567 | ACACTAAGATATTGCTTGAG/ccc | SEQ ID NO: 12 |
| E1B-84R splice acceptor (SA3) | 3595-3599 | 1882-1886 | GTCTTATGTAGTTTTGTATCTGTTTTGCAG/cag | SEQ ID NO: 13 |
| splice donor 2 (SD2) | 3506-3510 | 1793-1797 | gag/GTACTGAAAT | SEQ ID NO. 14 |

The "forward slash" indicates the actual splice site.

-continued

| Amino Acids | | | Codons |
|---|---|---|---|
| Phenylalanine | Phe | F | UUC UUU |
| Proline | Pro | P | CCA CCC CCG CCU |
| Serine | Ser | S | AGC AGU UCA UCC UCG UCU |
| Threonine | Thr | T | ACA ACC ACG ACU |
| Tryptophan | Trp | W | UGG |
| Tyrosine | Tyr | Y | UAC UAU |
| Valine | Val | V | GUA GUC GUG GUU |
| Stop | | | TAA TGA TAG |

In a preferred embodiment, increased levels of the E1B-156R isoform are achieved as a result of a mutated 93R splice site in the E1B gene.

In a preferred embodiment, the E1B gene splicing recognition regions are mutated at one or more of the following positions: a) nucleotide 3216 (e.g. cagGAGG–>cggGAGG) of the adenovirus Ad5 genome (accession number AC_000008.1) (SEQ ID NO: 41); b) nucleotide 3218 of the adenovirus Ad5 genome (accession number AC_000008.1) (SEQ ID NO: 41); and/or c) nucleotide 3221 of the adenovirus Ad5 genome (accession number AC_000008.1) (SEQ ID NO: 41). Equivalent mutations in other adenovirus serotypes will be clear to the skilled reader.

In a more preferred embodiment, the E1B gene contains one or more of the following mutations: a) A3216G (cag-GAGG–>cggGAGG); b) G3218A; and/or c) G3221A, corresponding to positions 1503, 1505 and 1508 in the E1B gene (SEQ ID NO: 1) respectively. Equivalent mutations in other adenovirus serotypes will be clear to the skilled reader.

Levels of Isoforms

Any mutation that is introduced into the sequence of an adenovirus genome should have the effect that the proportion of at least one of the E1B splicing isoforms, E1B-156R, E1B-496R, E1B-93R, and E1B-84R, (and potentially two, three, or all four isoforms) varies with respect to levels that are present in the wild-type under similar conditions. Preferably, the proportion of the E1B-496R isoform is decreased relative to wild-type levels, or even totally shut down. Alternatively, the proportion of the E1B-156R isoform is increased relative to the E1B-496R isoform, the proportion of the E1B-156R isoform is increased relative to the E1B-93R isoform and/or the proportion of the E1B-156R isoform is increased relative to the E1B-84R isoform. These changes in levels of particular isoforms have the effect of enhancing oncolysis, which can also be expressed as enhancing the oncolytic index.

The level of the E1B-156R isoform may be increased relative to the E1B-156R in the equivalent wild type adenovirus sequence. Herein, "increased" means that the proportion of the E1B-156R isoform is increased at least 2-fold, 4-fold, 10-fold, 20-fold, 50-fold, 100-fold, 1,000-fold or 10,000-fold relative to wild type levels.

Herein, "decreased" means that the proportion of the E1B-496R isoform is decreased at least 2-fold, 4-fold, 10-fold, 20-fold, 50-fold, 100-fold, 1,000-fold or 10,000-fold relative to wild type levels.

Herein, "wild type levels" refers to the levels of E1B-156R, E1B-496R, E1B-93R, and E1B-84R isoforms that are evident by expression of these proteins from the wild-type adenovirus, with no mutations in the E1B gene reference sequence (i.e. SEQ ID NO: 1). For example, the proportion of the mutant Ad5 E1B-156R isoform may be increased relative to levels in wild-type Ad5 adenovirus, such that mutant adenovirus has an oncolytic effect in a cancer cell. Mutant Ad2 E1B-156R isoform may be increased relative to levels in wild-type Ad2 adenovirus.

Preferred viruses according to the invention may have diminished or inhibited expression of E1B-93R, and preferably do not express E1B-93R. By "does not express" is meant herein that the detectable level of the E1B-93R sequence is less than 50%, 10%, 1% of the level of the E1B-93R sequence in the wild type adenovirus under equivalent conditions, preferably less than 0.1%, less than 0.01% or even less. This has the effect of raising the expression of E1B-156R.

Preferably, an optimal ratio of the E1B-156R, E1B-496R, E1B-93R, and E1B-84R isoform protein levels would lie along the lines of about 67:0:0:33 as compared to about 5:70:10:15 for wild-type viruses. As the skilled reader will appreciate, however, it is difficult or impossible to be exact about relative levels of this type since they are dependent on the point in the infection cycle assessed, i.e. early/intermediate/late. The ratios changes for the benefit of the shorter spliceforms at the cost of 496R (which is the unspliced, full-length RNA). In particular, favoured ratios of the E1B-156R isoform to the E1B-496R isoform are 2:1, 5:1, 10:1, 20:1, 50:1, 100:1, 1000:1 or 10,000:1 or more. A ratio of 100:1 or more is preferred.

Herein reference to "the proportion" of the E1B-156R, E1B-496R, E1B-93R, or E1B-84R isoforms refers to: a) the level of the isoform protein that is expressed; and/or b) the level of the isoform mRNA that is produced.

Techniques for measuring mRNA levels will be known to those of skill in the art for the quantitation of polynucleotides, such as, for example, nucleic acid amplification, for instance PCR, RT-PCR, TaqMan-based methodologies, RNase protection, Northern blotting and in situ hybridization techniques, and quantitative versions of these methods. Changes in mRNA expression levels may be of a temporal, spatial or quantitative nature. The number of copies of each E1B isoform mRNA can be calculated and compared to a reference, for example a house keeping gene such as beta-actin or GAPDH or a plasmid carrying the specific "amplicon of interest".

If polypeptide levels are to be monitored, any assay technique can be used that can determine levels of a specific polypeptide, including radioimmunoassays (RIA), competitive-binding assays, Western Blot analysis, FACS and enzyme-linked immunosorbent (ELISA) assays. Antibodies which specifically bind to particular splice isoforms may be used, for example. The antibodies may be used with or without modification, and may be labelled by joining them, either covalently or non-covalently, with an analytically-detectable reagent such as a radioisotope, a fluorescent molecule or an enzyme or other reporter molecule. A wide variety of reporter molecules known in the art may be used.

E1B Isoforms

Very little is known about the E1B-156R, E1B-93R, E1B-84R isoforms. Production of different E1B mRNAs is regulated during the infection process. While mainly the 2.28 kb form is produced early in infection, the proportion of shorter spliced mRNAs increases over time and the E1B-84R transcript becomes predominant in the late phase of infection. The isoform protein expression closely follows the transcription pattern of the mRNAs (Chow et. al (1979) *J. Mol. Biol.* 134:265-303; Montell et. al (1984) *Mol. Cell.*

Biol. 4:966-972; Spector et. al (1978) *J. Mol. Biol.* 126:395-414; Virtanen and Pettersson (1985) *J. Virol.* 54:383-391; Wilson and Darnell (1981) *J. Mol. Biol.* 148:231-251).

It has been shown that different spliceotypes can interact both hetero- and homogeneously with each other through the N-terminus, and the C-terminus must carry specific functions that cannot be complemented for by alternative E1B spliceotypes. When infecting with viruses lacking the expression of a specific spliceotype the viability loss can be complemented by co-transfecting with an expression plasmid for corresponding spliceotype. The co-transfection with an alternative spliceotype does not complement the loss.

Mutant Adenoviruses

The table below summarises the details of some representative adenovirus mutants in provided as examples of the teaching of the invention, along with some experimental control viruses.

| Virus | Mutations[a] | Description |
|---|---|---|
| Ixovex | A3216G | E1B-93R splice site mutant |
| | | Does not express E1B-93R isoform |
| | | Destabilises E1B-496R due to sequence change |
| | | Increases in E1B-156R levels |
| Ixo-ctrl | | Control (wild-type) virus |
| Ixo-156 | T3272G/ G3275A | E1B-156R splice acceptor site mutant |
| | | Does not express E1B-156R isoform |
| | | E1B-496R sequence is not changed |
| | | Expresses other E1B gene products |
| | | 93R levels increase |
| Ixo-93 | G3218A/ G3221A | E1B-93R splice acceptor site mutant |
| | | Does not express E1B-93R isoform |
| | | E1B-496R sequence is not changed |
| | | Increases in E1B-156R levels |
| Ixo-SD | G2255A/ T2258C | E1B splice donor 1 site mutant |
| | | Does not express E1B-93R, -156R and -84R isoforms |
| | | E1B-496R sequence is not changed |
| Ixo-Stop | G2274T | Inserts a stop codon downstream of the E1B splice donor 1 site |
| | | Does not express E1B-496R protein |
| | | Expresses E1B-93R, -156R and -84R isoforms |

[a]Numbered according to position in the Ad5 genome accession number AC_000008.1 (SEQ ID NO: 41)

The adenovirus herein termed the Ixovex virus has diminished or inhibited expression of E1B-93R, and preferably does not express E1B-93R. By "does not express" is meant herein that the detectable level of the E1B-93R sequence is less than 50%, 10%, 1% of the level of the E1B-93R sequence in the wild type adenovirus under equivalent conditions, preferably less than 0.1%, less than 0.01% or even less. This has the effect of raising the expression of E1B-156R.

Additionally, in this virus the full length E1B protein E1B-496R is destabilized. By "destabilised" is meant that the protein becomes substantially undetectable due to the mutation. This leaves only E1B-156R and E1B-84R still expressed from the 496 reading frame. The unstable nature of E1B-55k is discussed in Gabler et al. 1998 J. Virol.; and Gonzalez 2002, J. Virol.

The efficacy of Ixovex as compared to H101 suggests that to some extent, E1B-496R and E1B-156R have overlapping functions (Sieber et. al. (2007) *J. Virol.* 81 (1): 95-105). E1B-496R and E1B-156R have been found to bind many similar factors. E1B-156R can bind to E4orf6, the binding partner with which E1B-496R utilises most of its important functions. Interestingly, E1B-156R has also been found to bind p53, although with less affinity. E1B-156R can substitute for E1B55k in cell transformation experiments. Also, E1B-156R induces tumours in in vivo models, when over-expressed together with E1A. Specifically, the E1B-156R spliceomer was found herein to have a cell transforming potential separate from the E1B-496R protein.

It is an advantage of the present invention that in order to achieve the described oncogenic effect, viruses according to the present invention do not require the deletion of the whole of the E1B gene.

Methods of Generating Recombinant Viruses

The invention provides polynucleotides encoding the recombinant adenoviruses, optionally encoded within a vector suitable for virus production in a host cell.

The invention provides host cells comprising polynucleotides encoding the recombinant adenovirus.

The invention also includes a method of rendering an adenovirus oncolytic. Such a method involves engineering a mutant adenovirus in which the sequence of the E1B gene has been modified so as to increase the level of the E1B-156R isoform relative to the level in the equivalent wild-type adenovirus. The adenovirus type can be any of those described above, and is preferably a human adenovirus of subfamily group C, namely one of serotypes 1, 2, 5, 6, or 57, even more preferably, the term adenovirus applies to two human serotypes, Ad2 and Ad5. Similarly, the mutation may be any one of those described or exemplified herein. In certain embodiments, a hybrid virus may be engineered, for example, in which an E1B-156R from one adenovirus variant is expressed in another adenovirus variant. For example, an Ad2 E1B-156R may be expressed in an Ad5 adenovirus; it has been shown herein that adding Ad2 E1B-156R to Ad5 increases oncolytic activity by 10-fold.

Suitable techniques to engineer mutations in alternative adenoviruses will be known to those of skill in the art. A preferred method could be to use the widely used pShuttle system (Agilent Technologies) or use the method developed by Dr. Oberg (the inventor of IXOvex and board member of IXOgen)) using the pSuperShuttle system (see Ingemarsdotter, C. K., S. K. Baird, C. M. Connell, D. Oberg, G. Hallden, and I. A. McNeish. 2010. Low-dose paclitaxel synergizes with oncolytic adenoviruses via mitotic slippage and apoptosis in ovarian cancer. Oncogene 29:6051-6063). This allows the insertion or mutation of any sequence anywhere in the adenovirus, which pShuttle cannot do, being limited to the end regions of the adenoviral genome. Shortly, the flanking sequences (left and right arm) of the region of interest may be cloned into the pSuperShuttle plasmid on each side of an antibiotic selection gene (ASG). If a mutation of any sort (substitution, deletion or addition) is desired it can be incorporated in either arm. For the insertion of a gene of interest or a whole expression cassette into the virus the extensive multiple cloning sites on each side of the ASG may be used. When the complete pSupershuttle construct is sequenced and ready it is fused with the virus by homologous recombination. The inserted ASG allows for positive selection. The ASG is digested away leaving a small scar in the form of a unique restriction enzyme site, which can be used in future modifications of the virus. Other suitable variations on this technique will be known to those of skill in the art.

Construction of Adenovirus E1B-55K Mutants

Methods for the construction of adenoviral mutants are generally known in the art. See, Mittal (1993) *Virus Res.*, 28: 67-90 and Hermiston et al., *Methods in Molecular Medicine: Adenovirus Methods and Protocols* (1999) ed. Wold, Humana Press. Further, the adenovirus 5 genome is registered as NCBI Reference Sequence: AC_000008.1, and the virus is available from the American Type Culture Collection, Rockville, Md., U.S.A., under accession number: VR-1516.

Generally, adenovirus vector construction involves an initial deletion or modification of a desired region of the adenoviral genome, preferably the Ad5 genome, in a plasmid cassette using standard techniques.

Certain of the materials and methods used to construct adenovirus mutants are described by Hanke et. al. (1990) *Virology,* 177: 437-444 and Bett et. al., (1993) *J. Virol.* 67: 5911-5921, and in PCT/CA96/00375. Many of the materials used to construct adenovirus mutants are provided commercially. See also, Hermiston et al., *Methods in Molecular Medicine: Adenovirus Methods and Protocols* (1999) ed. Wold, Humana Press. Other details are provided herein.

Cell lines that were used to conduct the experiments described herein are readily available from recognised depositary institutions. For example, the following cell lines were used herein to assess cytotoxicity: H1299, FaDu, H460, A549, HeLa, Hek293, JH293 and NHBE.

A preferred procedure for constructing the adenoviral E1B gene mutants of the present invention is to make site-specific mutations in the adenoviral genome in a plasmid cassette using well established techniques of molecular biology, or modifications of these techniques, referred to herein. This can be realized using various materials and methods.

Methods of Treating Cancer

The invention provides recombinant adenoviruses that produce an oncolytic effect in a cancer cell. The cancer cell may be a neoplastic cell. The invention also provides novel methods of treating cancer, characterised by neoplastic cells. The neoplastic cells may preferably substantially lack p53 function ($p53^{(-)}$). Such a method may comprise:

a) administering a dose of the recombinant adenovirus according to the invention, that carries a mutation in the E1B gene, to a patient in need of treatment;

b) allowing sufficient time for the recombinant adenovirus to infect neoplastic cells of said cancer, wherein the mutant adenovirus has an oncolytic effect which is selective for the cancer cells relative to the non-neoplastic cells; and c) optionally administering further doses of the recombinant adenovirus.

The cancer cell or neoplastic cell may substantially lack p53 function.

The invention provides recombinant adenoviruses for use as a therapeutic agent in treating a patient with cancer. Preferably the cancer is characterised by neoplastic cells. Preferably, those neoplastic cells substantially lack p53 function.

The invention also provides compositions comprising recombinant adenoviruses of the invention.

The invention provides pharmaceutical compositions comprising a recombinant adenovirus of the invention.

The invention also provides processes for making a pharmaceutical composition involving combining a recombinant adenovirus of the invention with a pharmaceutically acceptable carrier.

The compositions may additionally comprise an agent for chemotherapy.

The present invention provides several novel methods and compositions for ablating neoplastic cells by infecting the neoplastic cells with a recombinant adenovirus which is substantially replication-deficient in non-neoplastic cells and which exhibits at least a partial replication phenotype in neoplastic cells. The difference in replication phenotype of the adenovirus constructs of the invention in neoplastic and non-neoplastic cells provides a biological basis for viral-based therapy of cancer.

A cell population (such as a mixed cell culture, human cancer patient or non-human mammalian subject) which comprises a subpopulation of neoplastic cells lacking p53 function and a subpopulation of non-neoplastic cells which express essentially normal p53 function can be contacted under infective conditions (i.e. conditions suitable for adenoviral infection of the cell population, typically physiological conditions) with a composition comprising an infectious dosage of a $E1B\text{-}p53^{(-)}$ replication inhibited adenovirus. Such a contacting step results in infection of the cell population with the $E1B\text{-}p53^{(-)}$ replication-deficient adenovirus. The infection produces preferential expression of a replication phenotype in a significant fraction of the cells comprising the subpopulation of neoplastic cells lacking p53 function, but does not produce a substantial expression of a replicative phenotype in the subpopulation of non-neoplastic cells having essentially normal p53 function. The expression of the replication phenotype in an infected $p53^{(-)}$ cell results in the death of the cell, such as by the cytopathic effect (CPE), cell lysis, apoptosis, or similar, resulting in a selective ablation of neoplastic $p53^{(-)}$ cells from the cell population.

It is desirable for the mutant virus to be replicable and to form infectious virions containing the mutant viral genome which may spread and infect other cells, thus amplifying the anti-neoplastic action of an initial dosage of mutant virus.

Herein, $E1B\text{-}p53^{(-)}$ replication inhibited adenovirus constructs suitable for selective killing of $p53^{(-)}$ neoplastic cells are those described above.

Candidate antineoplastic adenovirus mutants may be further evaluated by their capacity to reduce tumourigenesis or neoplastic cell burden in nu/nu mice harbouring a transplant of neoplastic cells lacking p53 function, as compared to untreated mice harbouring an equivalent transplant of the neoplastic cells.

Antineoplastic replication-deficient adenovirus mutants may be formulated for therapeutic, prophylactic and, potentially, diagnostic administration to a patient having a neoplastic disease. For therapeutic or prophylactic uses, a sterile composition containing a pharmacologically effective dosage of one or more species of antineoplastic replication inhibited adenovirus mutant is administered to a patient for treatment of a neoplastic condition. A pharmaceutically acceptable carrier or excipient is often employed in such sterile compositions. A variety of aqueous solutions can be used, e.g., water, buffered water, 0.4% saline, 0.3% glycine and the like. These solutions are sterile and generally free of particulate matter other than the desired adenoviral virions. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. Excipients which enhance infection of cells by adenovirus may be included.

Therapy of neoplastic disease may be afforded by administering to a patient or subject a composition comprising replication-defective adenoviruses of the invention. Various human and mammalian neoplasms comprising cells that lack p53 function may be treated with the replication inhibited adenoviral constructs. For example (but not limiting to), a human patient or non-human mammal having a bronchogenic carcinoma, nasopharyngeal carcinoma, laryngeal carcinoma, small cell and non-small cell lung carcinoma, lung adenocarcinoma, hepatocarcinoma, pancreatic carcinoma, bladder carcinoma, colon carcinoma, breast carcinoma, cervical carcinoma, ovarian carcinoma, or lymphocytic leukaemias may be treated by administering an effective antineoplastic dosage of an appropriate replication inhibited adenovirus.

Suspensions of infectious adenovirus particles may be applied to neoplastic tissue by various routes, including intravenous, intraperitoneal, intramuscular, subdermal, and topical. A adenovirus suspension, preferably an aqueous suspension, containing between about $10^3$ to $10^{15}$ or more virion particles per ml (such as between about $10^5$ to $10^{12}$ or more virion particles per ml, between about $10^7$ to $10^{10}$ or more virion particles per ml, or about $10^9$ virion particles per ml) may be inhaled as a mist (e.g. for pulmonary delivery to treat bronchogenic carcinoma, small-cell lung carcinoma, non-small cell lung carcinoma, lung adenocarcinoma, or laryngeal cancer). Alternatively, such a suspension may be swabbed directly on a tumour site for treating a tumour (e.g. bronchogenic carcinoma, nasopharyngeal carcinoma, laryngeal carcinoma, cervical carcinoma) or may be administered by infusion (e.g. into the peritoneal cavity for treating ovarian cancer, into the portal vein for treating hepatocarcinoma or liver metastases from other non-hepatic primary tumours) or other suitable route, including direct injection into a tumour mass (e.g. a breast tumour), enema (e.g. colon cancer), or catheter (e.g. bladder cancer).

Replication inhibited viruses may also be delivered to neoplastic cells by liposome or immunoliposome delivery; such delivery may be selectively targeted to neoplastic cells on the basis of a cell surface property present on the neoplastic cell population (e.g. the presence of a cell surface protein which binds an immunoglobulin in an immunoliposome). For example, a suspension of replication inhibited adenovirus virions can be encapsulated in micelles to form immunoliposomes by conventional methods (for example see U.S. Pat. No. 5,043,164, U.S. Pat. No. 4,957,735, U.S. Pat. No. 4,925,661; Connor and Huang (1985) *J. Cell Biol.* 101: 582; Lasic DD (1992) *Nature* 355: 279; *Novel Drug Delivery* (1989) eds. Prescott and Nimmo, Wiley, N.Y.; and Reddy et al. (1992) *J. Immunol.* 148: 1585). Immunoliposomes comprising an antibody that binds specifically to a cancer cell antigen (e.g., CALLA, CEA) present on the cancer cells of the individual may be used to target virions to those cells.

The compositions containing the present antineoplastic replication-deficient adenoviruses or cocktails thereof can be administered for prophylactic and/or therapeutic treatments of neoplastic disease. In therapeutic application, compositions are administered to a patient already affected by the particular neoplastic disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration.

In prophylactic applications, compositions containing the antineoplastic replication inhibited adenoviruses or cocktails thereof are administered to a patient not presently in a neoplastic disease state to enhance the patient's resistance to recurrence of a neoplasm or to prolong remission time. Such an amount is defined to be a "prophylactically effective dose." In this use, the precise amounts again depend upon the patient's state of health and general level of immunity.

Single or multiple administrations of the compositions can be carried out with dose levels and pattern being selected by the treating physician. In any event, the pharmaceutical formulations should provide a quantity of the antineoplastic replication inhibited adenoviruses of this invention sufficient to effectively treat the patient.

Antineoplastic replication inhibited adenoviral therapy of the present invention may be combined with other antineoplastic protocols, such as conventional chemotherapy.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The practice of the present invention will employ, unless otherwise indicated, conventional techniques of molecular biology, microbiology, recombinant DNA technology and immunology, which are within the skill of those working in the art.

Most general molecular biology, microbiology recombinant DNA technology and immunological techniques can be found in Sambrook et al., *Molecular Cloning, A Laboratory Manual* (2001) Cold Harbor-Laboratory Press, Cold Spring Harbor, N.Y. or Ausubel et al., *Current protocols in molecular biology* (1990) John Wiley and Sons, N.Y.

Unless defined otherwise, all technical and scientific terms used herein have the same meaning as commonly understood by one of ordinary skill in the art to which this invention belongs.

BRIEF DESCRIPTION OF DRAWINGS

FIG. 2. E1B splice map showing alternative E1B gene products. The full-length E1B transcript carries the E1B-176R and E1B-496R open reading frame (ORF). Through alternative splicing in the E1B-496 ORF another three proteins, E1B-93R, E1B-156R and E1B-84R, are expressed. The lesser proteins have the 79 amino terminal amino acids in common with E1B-496R but differ in the carboxy terminal, except for E1B-156R, which splices in frame with E1B-496R.

9282 CS (top panel) and the monoclonal □-actin antibody I-19-SC as loading control (lower panel).

Figure 6:
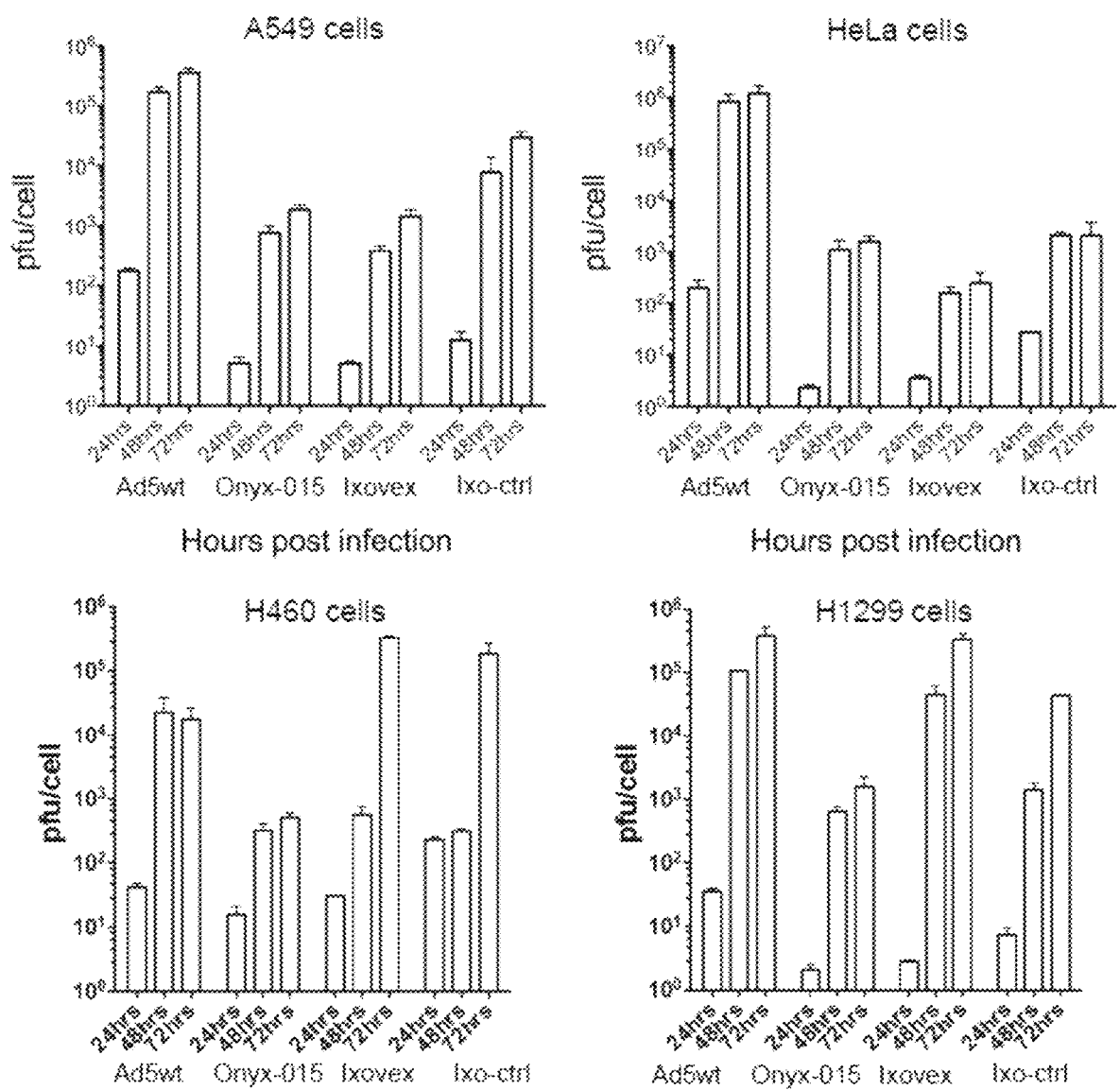

FIG. 6. Replication assay in cancer cell lines. Each cell line was infected with 5 pfu/cell of respective virus. Cells and media were harvested at 24, 48 and 72 hpi and analysed by a limited dilution assay. CPE was noted visually after 10 days and $TCID_{50}$ (pfu/cell) results were calculated, as described in materials and methods.

Figure 7:
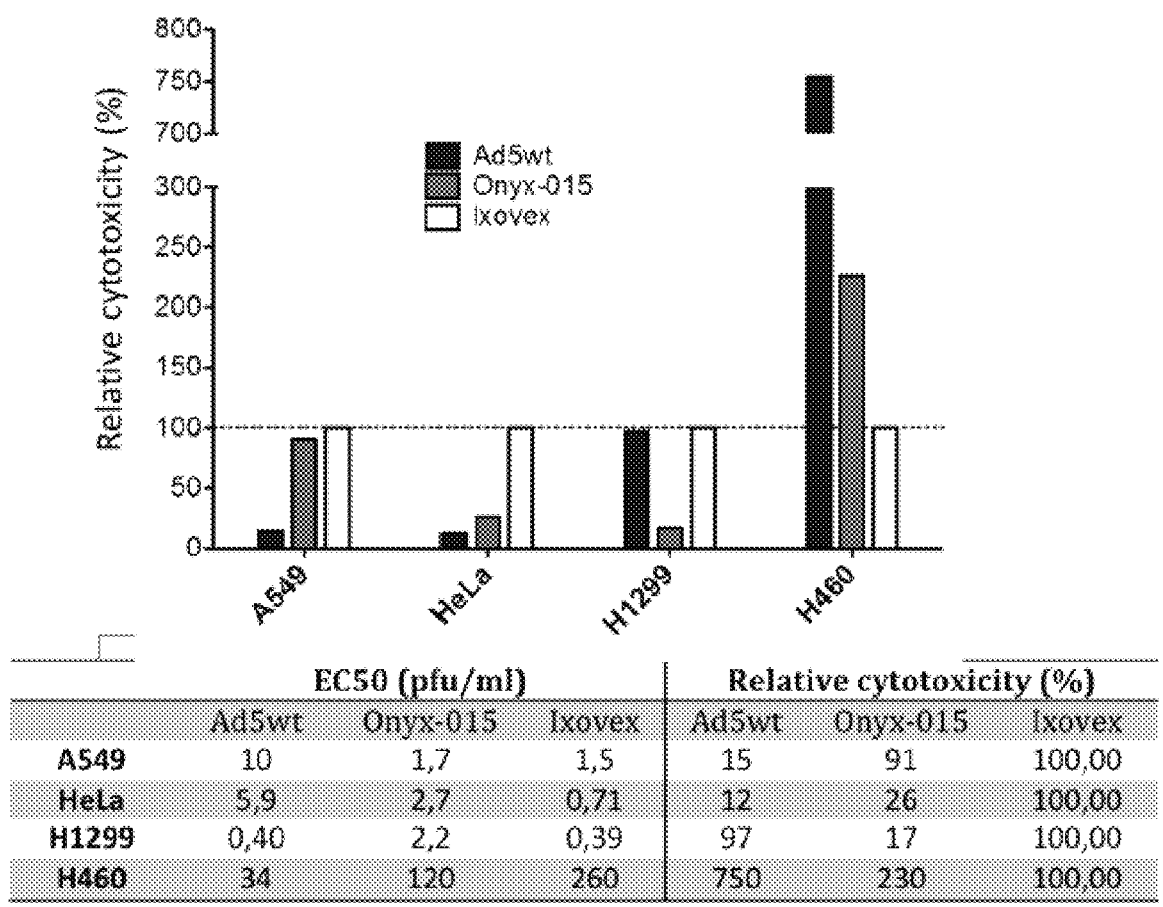

FIG. 7. The relative cytotoxicity of the Ixovex, Ad5wt and Onyx-015 viruses in cancer cells. The respective cell line was infected with the indicated viruses in a 5-fold dilution series. The cytotoxicity was measured 6 days post infection (dpi) using the MTS assay and $EC_{50}$ values were calculated.

Figure 8:
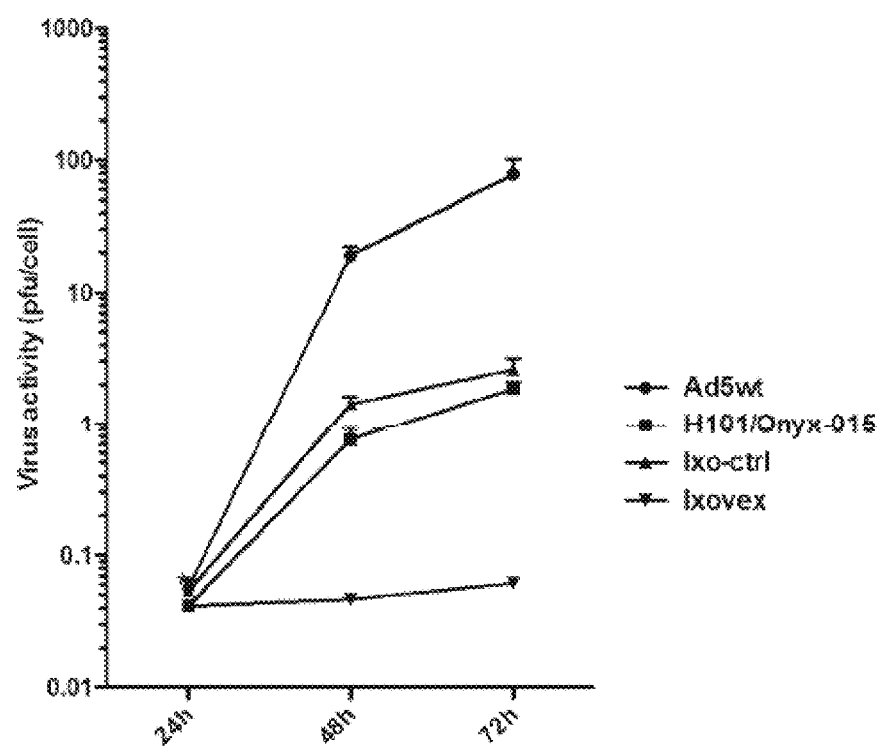

FIG. 8. Replication efficiency in Normal Human Bronchial Epithelial cells. Each cell line was infected with 5 pfu/cell of the respective virus. Cells and media were harvested at 24, 48 and 72 hpi and analysed by a limited dilution assay. CPE was noted visually after 10 days and $TCID_{50}$ (pfu/cell) results were calculated, as described herein.

FIG. 9. Ixovex shows more than 500-fold less cytotoxicity to normal cells compared with the unmodified virus (Ad5wt). Presented is the fold inhibition of cytotoxicity in relation to Ad5wt (bottom row) and the raw $EC_{50}$ values (top row). The cytotoxicity was measured at 6 dpi using the MTS assay.

Figure 10:
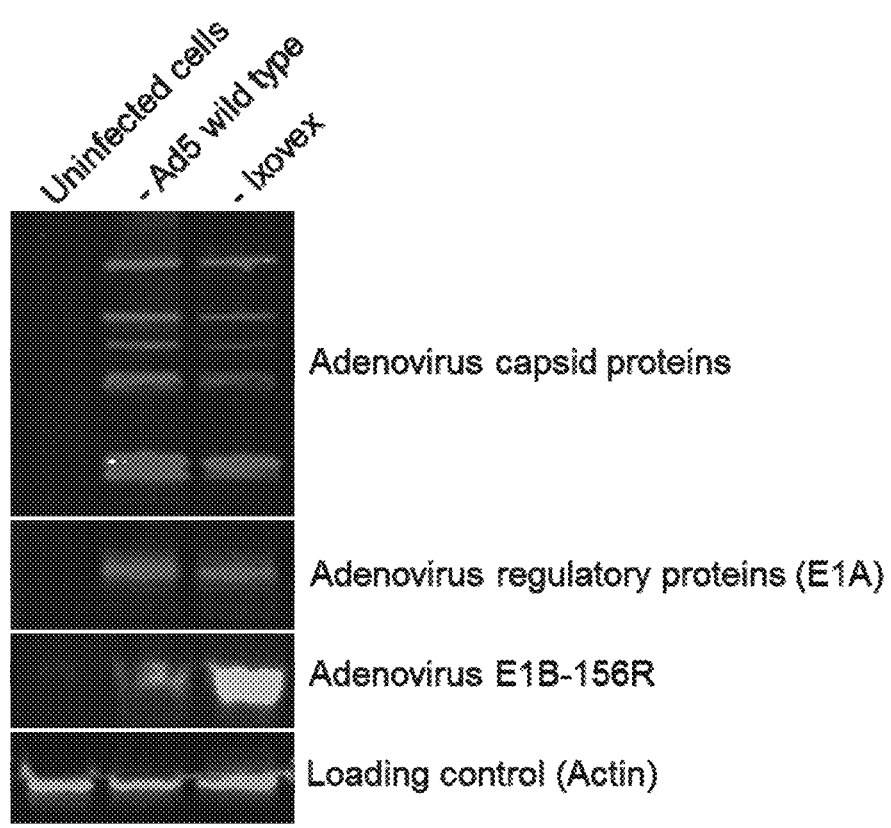

FIG. 10. The E1B-156R protein is overexpressed by Ixovex. Western blot was performed on total protein extracted at 48 hpi from H1299 cells infected with 10 pfu/cell of Ixovex or Ad5wt.

Figure 11A:
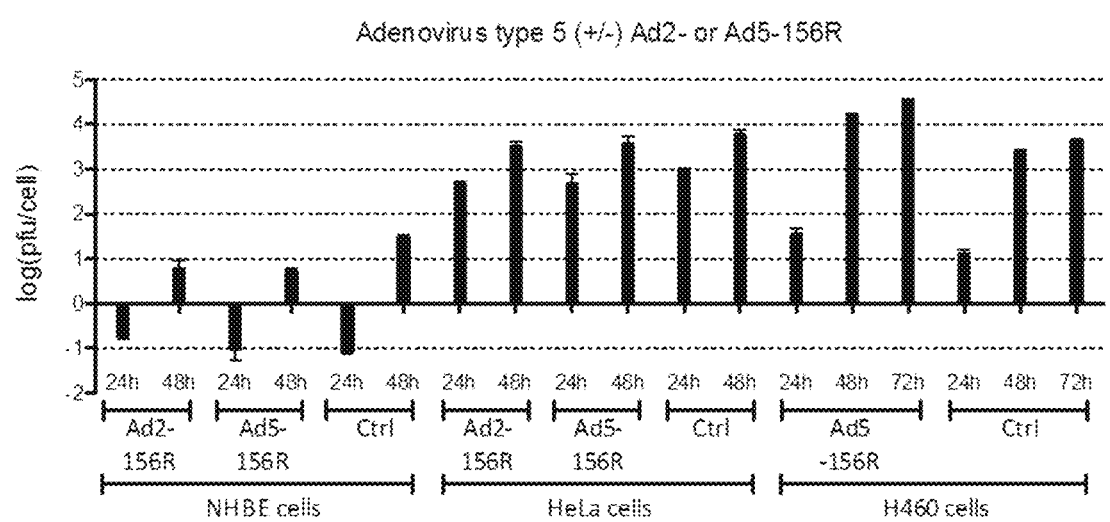
Figure 11B:
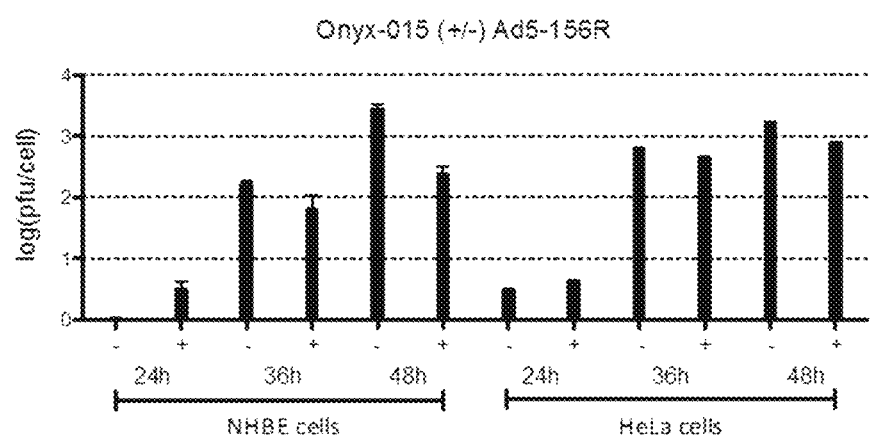
Figure 11C:
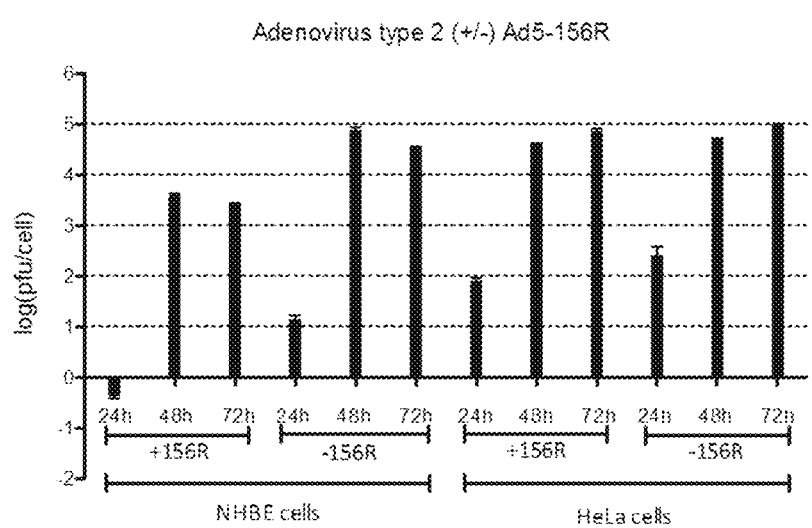

FIGS. 11A, 11B, and 11C. Ad5- and Ad2-156R proteins enhanced the Oncolytic Index (OI) in cancer cells as compared to normal cells. FIG. 11A) Ad5- and Ad2-156R expression plasmids were transfected into Ad5wt-infected HeLa and NHBE cells. In parallel, an additional cancer cells line (H460, large cell lung carcinoma) was included in Ad5-156R complementation. FIG. 11B) Ad5-156R was transfected into ONYX-015 infected cells. FIG. 11C) Ad5-156R was transfected into Ad2wt-infected cells. The cells were infected with 2.5 pfu/cell and complemented or cross-complemented with expression plasmids for the respective E1B-156R. Samples were analysed with a Burst (viral replication) assay, at the indicated hpi.

FIG. 12. Table showing the 48 hpi data points for FIGS. 11A-C (except for the H460 data points which were collect 72 hpi) and calculation of oncolytic indices, where OI=((a/b)/(c/d)). a=pfu/cellcancer cells+156R, b=pfu/cellnormal cells+156R, c=pfu/cellcancer cells−156R, d=pfu/cellnormal cells−156R.

FIG. 13. The protein sequence of E1B-156R for the serotypes of adenovirus subfamily C aligned with the sequences for serotypes of the subfamilies B, D and E. Shaded field: The similarities within group C. Gaps indicates where they differ. Underlined on Ad5: The amino acids that would single out Ad5-156R from the other E1B-156R proteins in subfamily C. (Serotype Ad1 (SEQ ID NO: 42); Ad2 (SEQ ID NO: 43); Ad6 (SEQ ID NO: 44); Ad5 (SEQ ID NO: 3); Ad4 (SEQ ID NO: 45); and Ad11 (SEQ ID NO: 46)).

Figure 14:
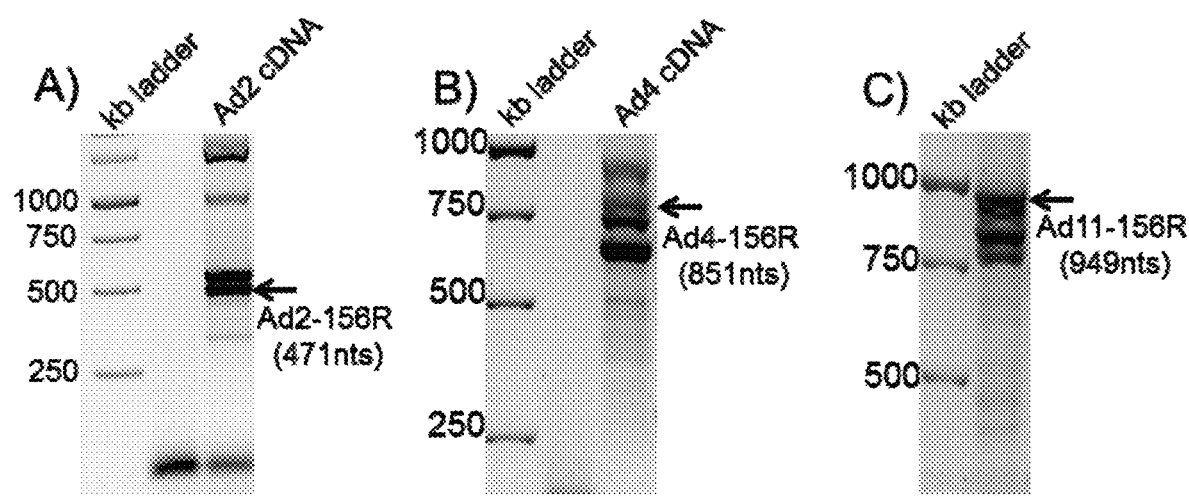

FIG. 14. DNA gels showing amplified cDNA bands corresponding to E1B-156R in Ad2, Ad4 and Ad11. All bands in the gels were cloned into the Topo-II PCR Blunt Vector (Invitrogen) and sequenced to confirm the indicated bands corresponded to the E1B-156R of each respective virus.

EXAMPLES

Materials and Methods
Virus Construction

Nucleotides 1-5055 of adenovirus serotype 5 (Ad5) were PCR amplified with Phusion PFU polymerase using Ad5start (SEQ ID NO:15—ccacctcgagttaattaacatcat-caataatataccttattttg) and Ad5wt5055as (SEQ ID NO: 16—gtgggtttaaacggatttggtcagggaaaacatg) oligonucleotides. Viral genomic DNA extracted from a CsCl purified Ad5 batch was used as a template. The PCR product was cloned into pShuttle (Stratagene) using restriction enzymes NotI and PmeI (NEB). To produce E1B 93R splice site mutations in pShuttle-5055, the oligonucleotides Mut93Rs (SEQ ID NO: 17—ccttgcatttgggtaatagaagaggagtgttcctaccttaccaatg) and Mut93Ras (SEQ ID NO: 18—cattggtaaggtaggaacactc-ctcttctattacccaaatgcaagg) were used in a PCR Mutagenesis XL reaction (Stratagene), according to manufacturers' instructions. Clones were screened and sent for sequencing. Five µg of the correct clone were linearised using PmeI (NEB), phenol/chloroform-treated and ethanol precipitated. Two hundred ng were mixed together with 100 ng of the pTG3602 plasmid. The mixture was electroporated into BJ5183 cells (Stratagene) and plated onto kanamycin (25 µg/ml) containing agar-plates. Clones were screened by size exclusion on a cracking gel. Briefly, the pellet of 1 ml bacterial culture was resuspended in 50 µl water and treated with 50 µl phenol/chloroform. The mixture was spun for 1 min at 13,000 rpm and the water phase collected. The water phase containing all DNA and RNA from the bacteria was treated for 5 min with DNA loading dye containing RNaseH and then run on a 0.7% agarose gel. DNA was prepared from the selected clones (Qiagen Maxi Prep kit) and sequenced to ensure the correct mutation had been introduced. Five µg of correct pT3602 mutant were digested with PacI to excise the viral genome, phenol/chloroform treated and ethanol precipitated. Two µg of the digested plasmid were transfected into 10e5 Hek293 cells in a 6-well plate using Transfectene (Biorad). Five days later the cells were harvested, subjected to three rounds of freeze/thawing and applied to a T175 bottle 80% subconfluent with A549 cells for bulking up of infected cell lysate.

A CF-10 (Thermo Scientific) was seeded with Hek293 cells and infected at 80% confluency with a third of the cell lysate. Three days later the CF-10 was harvested. The cell pellet was freeze/thawed three times, centrifuged to clear the lysate and applied to a 1.25/1.4 g/ml CsCl gradient and spun at 25,000 rpm in an ultracentrifuge. The virus band was collected with a 21G syringe and distributed into 1.35 g/ml CsCl columns. The columns were spun at 40,000 rpm overnight and the virus band was collected with a 21G syringe. The extracted virus was injected into a Slide-A-Lyzer (Thermo Scientific) cassette and dialysed overnight at 4° C. into 50 mM TRIS pH 7.8, 150 mM NaCl, 1 mM $MgCl_2$, 10% glycerol. The virus activity, assessed by the 50% tissue culture infective dose ($TCID_{50}$) (pfu/ml), was then determined by using JH293 cells as described in the Viral Replication section below. Viral DNA was purified from a small aliquot and the number of viral genomes per µl (particles/µl) was determined using a spectrophotometer. The ratios between the particles and activities of all viruses used herein were less than 20. Ixo-ctrl virus is a wild-type clone from the adenoviral serotype 5 strain pTG3602.

In parallel, pShuttle plasmids were made in which all splice sites were individually mutated without changing the amino acid sequence of the E1B-496R protein, using the PCR Mutagenesis XL Kit (Stratagene) according to manufacturers' recommendations.

| Oligonucleotides for PCR Mutagenesis | Oligonucleotide sequences | SEQ ID NO: |
|---|---|---|
| Ixo-CtrlS (wt) | CTTGCATTTGGGTAACAGgaggggggtgttcctacc | SEQ ID NO: 19 |
| Ixo-CtrlAS (wt) | ggtaggaacaccccctcCTGTTACCCAAATGCAAG | SEQ ID NO: 20 |
| Ixo-156Rs | ctaaGATATTGCTgGAacccgagagcatgtcc | SEQ ID NO: 21 |
| Ixo-156Ras | ggacatgctctcgggtTCcAGCAATATCttag | SEQ ID NO: 22 |
| Ixo-93Rs | CATTTGGGTAACAGaagagggggtgttcc | SEQ ID NO: 23 |
| Ixo-93Ras | ggaacacccctcttCTGTTACCCAAATG | SEQ ID NO: 24 |
| Ixo-SDs | gaatgaatgttgtacaaGTcGCTGAACTGTATC | SEQ ID NO: 25 |
| Ixo-SDas | GATACAGTTCAGCgACttgtacaacattcattc | SEQ ID NO: 26 |
| Ixo-StopS | gtggctgaactgtatccataactgagacgcattttg | SEQ ID NO: 27 |
| Ixo-StopAS | caaaatgcgtctcagttatggatacagttcagccac | SEQ ID NO: 28 |
| IxovexSense | CATTTGGGTAACGGGaggggggtgttcc | SEQ ID NO: 39 |
| IxovexAS | ggaacacccccctCCCGTTACCCAAATG | SEQ ID NO: 40 |

All these pShuttle plasmid were used in homologous recombination to generate a large set of viruses (see table 1).

TABLE 1

Adenovirus mutants provided by the invention.

| Virus | Mutations[a] | Description |
|---|---|---|
| Ixovex | A3216G | E1B-93R splice site mutant<br>Does not express E1B-93R isoform<br>Destabilises E1B-496R due to sequence change<br>Increases in E1B-156R levels |
| Ixo-ctrl | | Control (wild-type) virus |
| Ixo-156 | T3272G/<br>G3275A | E1B-156R splice acceptor site mutant<br>Does not express E1B-156R isoform<br>E1B-496R sequence is not changed<br>Expresses other E1B gene products<br>93R levels increase |
| Ixo-93 | G3218A/<br>G3221A | E1B-93R splice acceptor site mutant<br>Does not express E1B-93R isoform<br>E1B-496R sequence is not changed<br>Increases in E1B-156R levels |
| Ixo-SD | G2255A/<br>T2258C | E1B splice donor 1 site mutant<br>Does not express E1B-93R, -156R and -84R isoforms<br>E1B-496R sequence is not changed |
| Ixo-Stop | G2274T | Inserts a stop codon downstream of the E1B splice donor 1 site<br>Does not express E1B-496R protein<br>Expresses E1B-93R, -156R and -84R isoforms |

[a]Numbered according to position in the Ad5 genome accession number AC_000008.1 (SEQ ID NO: 41).

Tissue Culture

All cells were cultured at 37° C. and 5% $CO_2$ and were tested regularly for mycoplasma contamination. The cell lines used in this study are listed below.

| Cell name | Type | Culture medium | Source |
|---|---|---|---|
| H1299 | Non-small cell lung carcinoma | DMEM + 10% FCS | BCI* |
| FaDu | Pharyngeal squamous cell carcinoma | DMEM + 10% FCS | BCI |
| H460 | Large cell lung carcinoma | DMEM + 10% FCS | BCI |

-continued

| Cell name | Type | Culture medium | Source |
|---|---|---|---|
| A549 | Non-small cell lung carcinoma | DMEM + 10% FCS | Uppsala University |
| HeLa | Cervical Cancer | DMEM + 10% FCS | BCI |
| Hek293 | Human Embryonal Kidney cells | DMEM + 10% FCS | Uppsala University |
| JH293 | Human Embryonal Kidney cells | DMEM + 10% FCS | Uppsala University |
| NHBE | Normal Human Bronchial Epithelial | Bullet Kit (Lonza) | Lonza |

Cytotoxicity Assay

We used the 3-(4,5-dimethylthiazol-2-yl)-5(3-carboxymethoxyphenyl)-2-(4-sulfophenyl)-2H-tetrazolim (MTS) assay (CellTiter 96 Aqueous Non-Radioactive Cell Proliferation Assay; Promega, Wisconsin, USA) to assess the cytotoxicity of Ixovex and the control viruses. Aiming for cells to be confluent on day 6, 1,000-4,000 cells/well (depending on the rate of growth) were seeded in a 96 well plate in 90 µl of medium and 5% FCS. Viruses (in 10 µl of medium and 5% FCS) were added 18 hours later at nine 1:10 serial dilutions starting at 10,000 viral particles (vp)/cell, together with a positive (just cells with no virus) and a negative control (no cells just medium).

Six days following infection, survival was determined using MTS assay. MTS was mixed with phenazinemethosulphate (PMS) at 20:1 ratio and added to the cells. Following three hours of incubation, absorbance was measured at 490 nm using the Opsys MR 96-well µplate reader and Revelation Quicklink 4.04 software (Dynex Technologies, Virginia, USA). The values were established for each dilution and compared to negative control (100% cell death), and positive control (0% cell death). $EC_{50}$ values (half maximum effective concentration to kill 50% of cells—$EC_{50}$) were calculated by non-linear regression (sigmoidal dose-response curve) using GraphPad Prism (GraphPad Software, California, USA), utilising the following formula:

$$Y = \text{bottom} + (\text{top} - \text{bottom})/1 + 10^{[\log_{10} EC_{50} - X] \times \text{Hill slope}]}$$

Y is the response and starts at 'bottom' and goes to the 'top' in a sigmoidal fashion.

All experiments were performed in triplicate.

Viral Replication Assay

Cells were seeded in 6-well plate in medium with 10% FCS 24 hours prior to infection. 100 vp/cell were used to infect 80% confluent cells in a 2% FCS medium. Two hours after infection, the medium was replaced with a 10% FCS medium (primary infection). At hours post-infection (specified in respective figure), medium and cells were harvested (by scraping), frozen and thawed three times in liquid nitrogen and 37° C., respectively and stored at −80° C. until used. JH293 cells were seeded at 10,000 cells per well in a 96-well plate in 200 µl medium with 5% FCS. In the first row of the TCID50 the initial dilution of the different samples was between undiluted to 1:1000 dependent on hpi and virus, these dilutions from the primary infection were used to infect JH293 cells. The last row was left uninfected as a negative control. Between day 9 and 11, plates were inspected for cytopathogenic effect (CPE). The 50% tissue culture infective dose ($TCID_{50}$) and number of pfu/cell (cell count on the day of infection) were calculated using Reed-Muench accumulative method. See example below:

Example of a 96-well plate (+ indicate well with evidence of CPE):

| Dilution | | | | | | | | | | | | | % with CPE |
|---|---|---|---|---|---|---|---|---|---|---|---|---|---|
| $10^{-3}$ | + | + | + | + | + | + | + | + | + | + | + | + | 100% |
| $10^{-4}$ | + | + | + | + | + | + | + | + | + | + | + | + | 100% |
| $10^{-5}$ | + | + | + | + | + | + | + | + | + | + | + | + | 100% |
| $10^{-6}$ | | | + | + | | | + | | + | | | | 42% |
| $10^{-7}$ | | | | | | | | | | | | | 0% |
| $10^{-8}$ | | | | | | | | | | | | | 0% |
| $10^{-9}$ | | | | | | | | | | | | | 0% |

Negative controls

Calculate the proportionate distance: (% next above 50%−50%)/(% next above 50%−% next below 50%)=(100%−50%)/(100%−42%)=0.86

Calculate the 50% end point: $\log_{10}$ (dilution in which position is next above 50%)=$\log_{10}$ $10^{-5}$=−5

Combine the values to obtain $\log_{10}$ $TCID_{50}$=−5−0.86=−5.86

$TCID_{50}$ titre=$10^{-5.86}$ (or 1 in 7.24×$10^5$ dilution of the amount added to the top row). As 22 µl (0.022 ml) was added to the top row, $TCID_{50}$ /ml=7.24×$10^5$/0.022=3.29×$10^7$ Multiple by a constant: 3.29×$10^7$×0.69=2.27×$10^7$ pfu/ml For pfu/cell, multiply the above with the volume of virus added to each well of the 6-well plate (2 ml) and divide by the cell count on the day of infection (e.g. 2.4×$10^5$): (2.27×$10^7$×2)/2.4×$10^5$=189 pfu/cell.

Western Blot

A549 cells or H1299 were infected with 5 pfu/cell, total protein was extracted at 48 h post infection using RIPA buffer. Protein concentration was determined using Bradford reagent. Twenty µg total protein from each sample were loaded onto a 10% PAGE gel. The proteins were transferred to a PVDF (BioRad) membrane by wet blotting. The membrane was blocked using 3% BSA TBS solution for 1 h. Primary antibodies used were: Ad capsid proteins (AbCam-6982), E1B-55k (2A6, Sarnow, Sullivan Levine 1982, dilution 1:500), E1A (Santa cruz, M73), actin (Santa Cruz, 1-19) and p53 (Cell Signaling, #9282). All antibodies were diluted as recommended in 1,5% BSA TBS. Membranes were incubated with the primary antibodies for 15-24 hours at 4° C. where after they were washed with 1× TBS 3% Tween-20 three times for 10 min. HRP-coupled secondary antibodies against respective primary antibody were diluted 1:5000 in 1.5% BSA TBS and applied to the membrane for 1h. After removing the antibody dilution the membranes were washed with 1× TBS 3% Tween-20 three times for 10 min. Each membrane was exposed for 1 min with ECL Plus (GE, RPN2132). After having been wrapped in plastic foil the membranes were put in a Hypercassette together with Hyperfilm (GE) and the films were developed at selected time intervals. Alternatively, secondary antibodies labelled with IRDyes from LI-COR were used. Analysis was carried out using an Odyssey Imager.

RT-PCR

A549 cells were infected with 5 pfu/cell of respective virus, total RNA was extracted at 48 h post infection using Trizol (Invitrogen). The RNA was DNAse treated (NEB, DNase I), phenol/chloroform treated and ethanol precipitated. One µg total RNA was used to synthesise cDNA (Invitrogen, SuperScript® III) according to manufacturers' recommendations. cDNA was used as template in PCR (NEB Taq DNA Polymerase) reactions with a common sense oligonucleotide (55kSense, SEQ ID NO: 29—gcctgctactgt-tgtcttccg) and either of the following antisense nucleotides: 93Ras, SEQ ID NO: 30—caccccctcctgtacaac, 156Ras, SEQ ID NO: 31—gacatgctctcgggctgtacaac or 84Ras, SEQ ID NO: 32 caaacgagttggtgctcatg. The amplicon length of each was about 200 nucleotides. The PCR reaction was stopped after 20 cycles and an aliquot run on a 2% agarose gel.

Making the Adenoviral E1B-93R Splice Site Acceptor Mutant

The first 5000 nucleotides of the Ad5wt genome (NCBI Reference Sequence: AC_000008.1) were PCR amplified (primers Ad5wt5000start: SEQ ID NO: 15—ccacctcgagt-taattaaCATCATCAATAATATACCTTATTTTG;

Ad5wt5000as: SEQ ID NO: 16—gtgggtttaaacGGATTTG-GTCAGGGAAAACATG) and agarose gel purified. The purified product was digested with restriction enzymes NotI and PmeI (New England Biolabs) and cloned into the pShuttle plasmid (Stratagene), replacing the existing left arm for homologous recombination, producing pShuttle-LA, as by Agilent Technologies, AdEasy genomics.agilent.com/CollectionSubpage.aspx?PageType=Product&SubPageType=ProductData&PageID=592. This plasmid was recombined with the plasmid pTG3602, containing the complete Ad5wt genome, as recommended by Agilent Technologies in their AdEasy system using BJ5183 recombination competent cells. After recombination the BJ5183 bacteria were plated onto agar plates containing kanamycin. Single colonies were picked, grown and DNA was prepared from large cultures. Each DNA preparation was screened for the correct recombination event. The digestion of the genomes was performed with PacI (New England Biolabs). After the correct clones had been grown on agar plates, the genomes were digested out and transfected into HEK293 cells using Transfectin Transfection Reagent (Bio-Rad) according to the manufacturers' instructions. Four days after transfection virus lysates were harvested [Cells were collected by scraping together with the media and collected in a 15 ml falcon tube. The sample was freeze/thawed three times and used to infect a T175 bottle about 90% confluent with Hek293 cells. Three days later the cells and media was harvested and freeze/thawed three times] and then used to infect viral production factories called CF-10s (Nunc). These have the approximate surface area of forty T175 bottles, i.e. 7000 $cm^2$, and are used to grow large number of cells for the production of a large number of viruses. Briefly, the cells of four confluent T175 bottles were transferred in 1 L of 5% FCS DMEM media into a CF10. Twenty-five ml (¹/₄₀) of the cell-containing media was applied to a new T175 as a growth control. On the day the T175 was 90% confluent the CF10 was at the same stage. Half of the cell lysate was then injected into the CF10 and the media was moved around for an even distribution. Three days later the CF10 was shaken to dislodge the cells that had not started floating around yet due to viral infection. The CF10 was emptied, the cells spun down, washed in PBS and finally suspended in 50mM Tris-HCl, pH7.8. Purification was carried out by Caesium-chloride banding. Viruses were then purified and analysed for titre (particles) and activity (pfu). The vp:pfu unit ratio (vp:pfu units) for all viruses was between 10-20. Sequencing of one of the viral clones showed that it had a point mutation in the E1B-93R splice acceptor site.

Confirming the Existence of E1B-156R in Ad2, Ad4 and Ad11

A549 cells were infected with 5 pfu/cell of each virus. At 48 hpi, total RNA was extracted and 1 µg was converted to cDNA using Superscript-II (Invitrogen) with random hexamers. One µl of the total 50 ml was used as template in a PCR with serotype-specific primers (Ad2sense, SEQ ID NO: 33—ctcgaggaattcgccaccatggagcgaagaaacccatc, Ad2antisense, SEQ ID NO. 34—cacttctagatcaatctgtatct-tcatcgctag, Ad4sense, SEQ ID NO. 35—ggagatttggacggtct-tgg, Ad4antisense, SEQ ID NO. 36—ggatcccatcacattttgacg, Ad11sense, SEQ ID NO. 37—catccatggaggtttgggc, Ad11antisense, SEQ ID NO. 38—ccttaaaagaagcgtttccac). FIG. 14 shows a DNA gel showing the cDNA bands and highlights the bands corresponding to the E1B-156R cDNA. All bands on the gels were purified (NucleoSpin Gel and PCR Clean-up, Macherey-Nagel) and cloned into a Topo-II PCR Blunt Vector (Invitrogen). Clones were sent for sequencing. Ad2-156R and Ad5-156R were cloned into the p3× Flag-CMV-14 vector using EcoRI and XbaI.

Testing if the E1B-156R Protein Enhances Oncolytic Index

The cDNA for E1B-156R from Ad2 and Ad5 were PCR amplified using start and stop primers specific for each respective E1B-55k as discussed above. The primers included an EcoRI in the start primer and a XbaI site in the stop primer. The PCR fragments were digested with the two enzymes and ligated into p3× Flag-CMV-14 (Sigma-Aldrich). The constructs were sequenced for the correct insert.

Cancer cells (Hela and H460) and normal cells (NHBE) were transfected with 2 µg Ad2-156R or Ad5-156R expression plasmids (or a control plasmid) and co-infected with Ad5wt, ONYX-015 or Ad2wt. The transfection was performed using JetPRIME reagent (POLYPlus) according to manufacturers' instructions. Infection with the viruses was performed as discussed above. Briefly, each well in a 6-well plate was transfected with 2 µl JetPRIME reagent and 200 µl transfection buffer. Control wells were transfected with 2 µg inert plasmid, in the form of pUC19.

Viral replication was measured at various time points post-infection using the assays described above. The data are shown in FIGS. 11A, 11B and 11C. Oncolytic index was calculated as shown in FIG. 12.

Results

EJB-55k Protein is Lost

Figure 1:
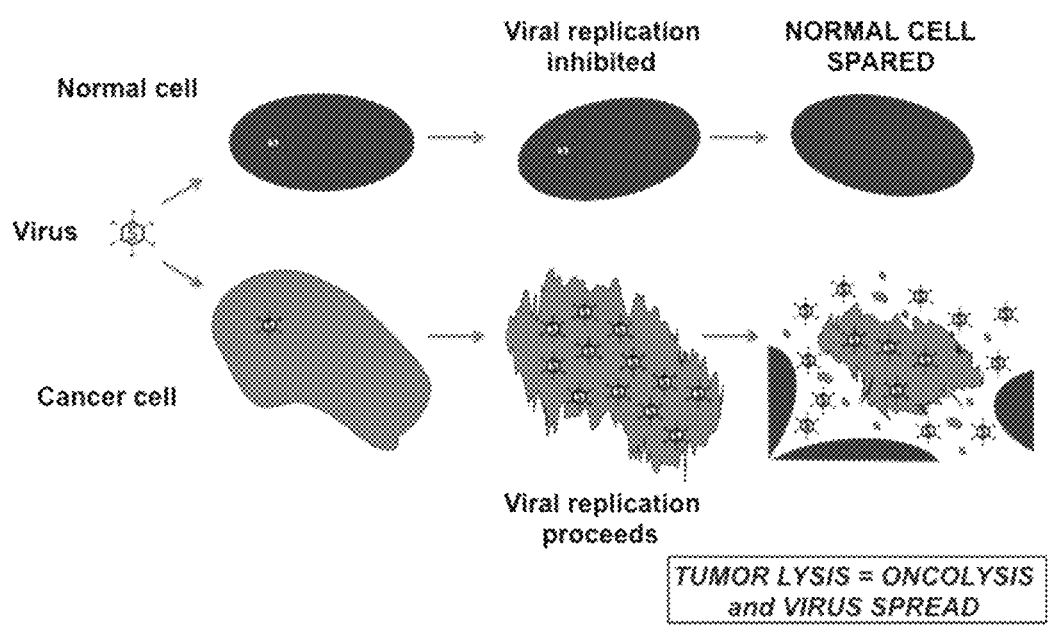
FIG. 1. Schematic description of an oncolytic virus.
Figure 3:
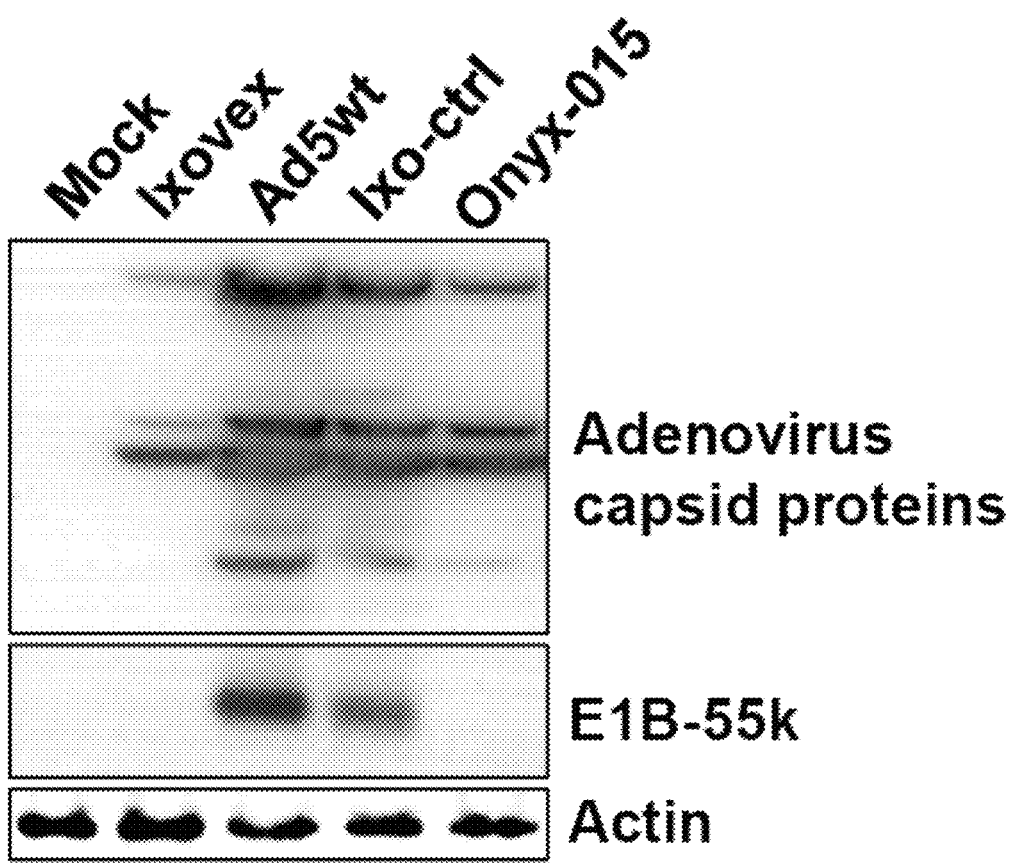
FIG. 3. An amino acid change in Ixovex in the E1B-55k protein inhibits its expression. A549 cells were infected with the respective virus at 5 pfu/cell and total cell lysate was collected 48 hours post infection (hpi). Shown is a western blot stained with polyclonal □-capsid protein Ab6982 antibody (top panel), monoclonal □-E1B-55k antibody 2A6 (middle panel) and monoclonal □-actin antibody I-19-SC as loading control (lowest panel).

Total protein lysates from Ad5wt, Onyx-015, Ixovex and Ixo-ctrl infected A549 cells showed that at 48 hpi all viruses expressed late protein (FIG. 3, top panel), i.e. had reached the late phase of adenoviral replication. Both Ixovex and Onyx-015 viruses expressed less late proteins than the Ad5wt and Ixo-ctrl, mirroring the reduced replication efficiency seen in FIG. 6 for A549 cells. The Ixovex single nucleotide point mutation (SNP, genomic location 3216), which changes the amino acid at position 400 in the E1B-55k protein from an arginine to a glycine, induced its destabilisation (FIG. 3, middle panel). The reduced amount of E1B-55k in Ixo-ctrl compared to Ad5wt mirrors the slightly lower replication efficiency of Ixo-ctrl in the A549 cells (FIG. 6, A549 panel).

Dynamics in the Usage of the E1B Splice Acceptors

Figure 4:
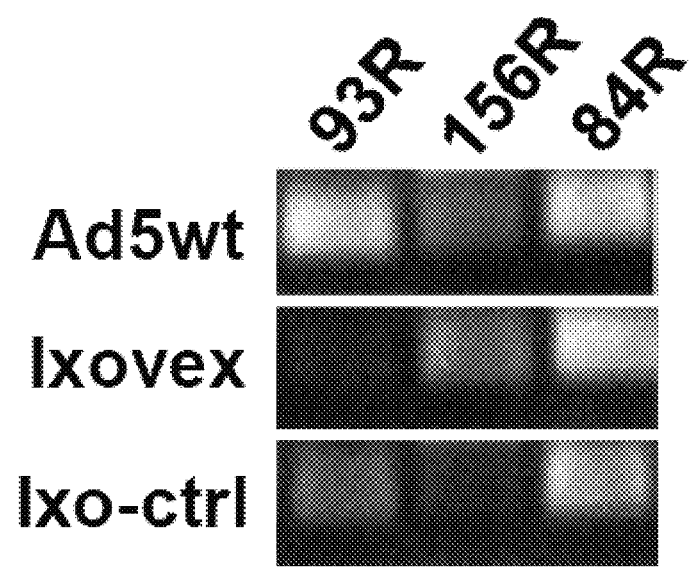
FIG. 4. The point mutation in the E1B55k open reading frame in Ixovex inhibits splicing to the 93R splice acceptor. A549 cells were infected with the respective virus at 5 pfu/cell and total RNA was collected at 48 hpi. cDNA was made using an oligo-dT primer. PCR was performed using a common sense primer upstream of the 55k splice donor and specific primers downstream of respective splice acceptor. The PCR reactions were run on a 2% agarose TBE gel stained with GelRed.

The SNP also inhibited use of the E1B-93R splice acceptor (FIG. 4, second panel) by changing the putative splice acceptor sequence from CAG:GA to CGG:GA. Interestingly, as a secondary effect to the inhibition of the 93R splice site, there is a compensatory switch to use of the E1B-156R splice acceptor (FIG. 4, middle panel). In the absence of the E1B-93R splice acceptor mutation, i.e. Ixo-ctrl, the relative use of the 93R splice site is restored (FIG. 4, lowest panel) as compared to the Ad5wt virus (FIG. 4, top panel). Onyx-015 could not be used in this experiment since this virus is deleted in the whole of the E1B-55k gene region.

Ixovex is Unable to Induce Degradation of p53

Figure 5:
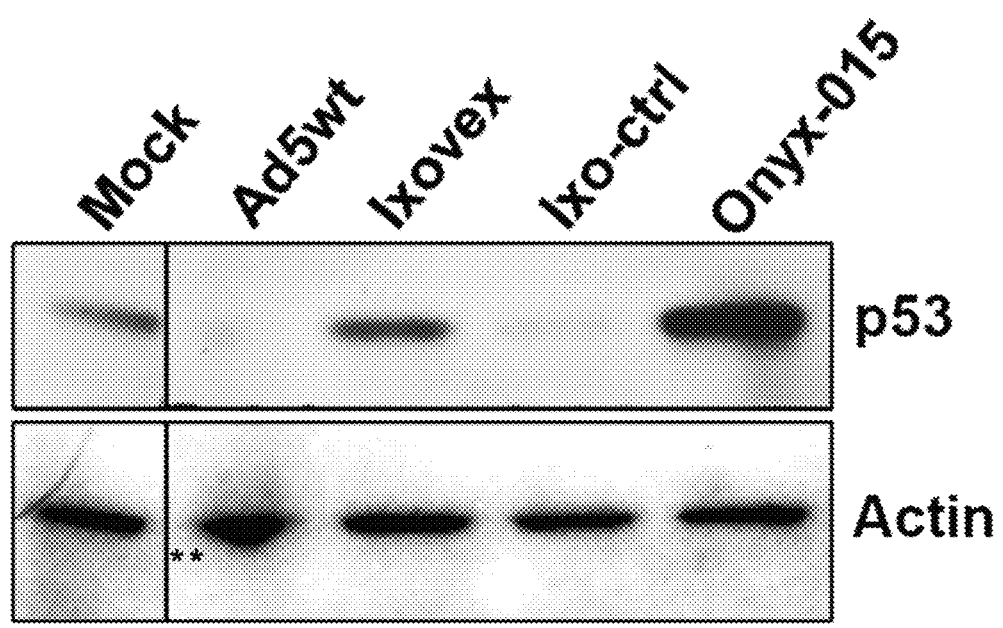
FIG. 5. Ixovex is inhibited in inducing degradation of p53. A549 cells were infected with the respective virus at 5 pfu/cell and cell lysate was collected 48 hpi. Shown is a western blot staining with a monoclonal □-p53 antibody

Western blot analysis showed that the SNP in Ixovex inhibited the virus from inducing the degradation of p53 (FIG. 5). In the absence of the E1B-93R splice acceptor mutation (i.e. Ixo-ctrl), the virus's capacity to inhibit p53 was restored. Interestingly, there was a much higher expression of p53 in the Onyx-015 infected cells.

Replication Efficiency in Cancer Cells

A replication assay was performed using Ad5wt, Onyx-015, Ixovex and Ixo-ctrl viruses in A549, HeLa, H460, H1299 and FaDu cells. The replication efficiency of all the viruses was below the detection limit in FaDu cells. In A549 and HeLa cells all viruses showed replication efficiency up to two orders of magnitude lower than the Ad5wt virus (FIG. 6, top panels). The replication attenuation was not seen, or was much less pronounced, in H460 and H1299 cells (FIG. 6, lower panels). In the two more permissive cancer cell lines, 100- to 1000-fold more Ixovex virus was produced, compared to Onyx-015.

Cytotoxicity in Cancer Cells

FIG. 7 shows the cytotoxicity of the Onyx-015 and Ixovex viruses relative to the Ad5wt virus in cancer cells. In comparison to Onyx-015, Ixovex was more efficient in all the cells tested (apart from H460 cells, in which Onyx-015 was 2,5-fold more toxic). The cytotoxicity of the Ixovex virus was similar to (or much higher than) the Ad5wt virus in the A549, HeLa and H1299 cancer cells lines.

Toxicity Profile in Normal Cells

The cytotoxicity of the Ad5wt, Onyx-015, Ixovex and Ixo-ctrl viruses was measured in NHBE cells (Normal Human Bronchial Epithelial cells). As seen in FIG. 9, the Ad5wt, Onyx-015, and Ixo-ctrl viruses are relatively toxic in normal cells as compared to cancer cells. The Ixovex virus however, showed an $EC_{50}$ value of 23 pfu/cell, which was higher than its $EC_{50}$ in the A549, HeLa and H1299 cancer cell lines. Ad5wt and Ixo-ctrl virus had $EC_{50}$ values of 0.042 and 0.031 pfu/cell, respectively, while Onyx-015 had 0.63 pfu/cell. Thus, Ad5wt was greater than 500-fold, Ixo-ctrl greater than 700-fold and Onyx-015 was greater than 35-fold more toxic to normal cells than Ixovex.

Replication Efficiency in NHBE Cells

At 48 hpi, virus activity was 30-fold higher in Ixo-ctrl and Onyx-015 and 500-fold higher in Ad5wt compared to Ixovex virus (FIG. 8). These differences were even more pronounced at 72 hpi, where virus activity was 50-fold higher in Ixo-ctrl and Onyx-015 and over 2000-fold higher in Ad5wt. In fact, these differences might even be more pronounced since Ixovex replication barely reached detection limit at all time points.

Ixovex Overexpressed the E1B-156R Protein

The protein levels of E1B-156R, adenovirus capsid proteins and E1A expressed by Ad5wt- and Ixovex-infected H1299 cells were analysed by western blot. FIG. 10 shows that Ixovex expressed similar amounts of all viral proteins except for the E1B-156R protein, the levels of which were increased by more than 20-fold, as compared to Ad5wt.

E1B-156R Protein Enhances Oncolytic Index

We hypothesised that adding the E1B-156R protein in trans would enhance the oncolytic index (OI) for Ad5wt if the E1B-156R protein was responsible for the oncolytic effect. Transfecting an Ad5-156R expression plasmid and co-infecting with Ad5wt increased the OI by 4-fold using Hela and NHBE cells (FIG. 11A and FIG. 12). An increase in oncolytic index was also observed when the same experiment was performed in an alternative cancer cell line, H460 (large cell lung carcinoma). Addition of Ad5-156R to Ad5wt-infected cells also had an enhancing effect on viral replication (FIG. 11A). Ad5-156R was transfected into cells co-infected with the ONYX-015 virus, which lacks the E1B-156R gene completely. The addition of Ad-156R increased the OI of the ONYX-015 more then 5-fold at the 48 hpi time point (FIG. 11B and FIG. 12). Similarly, addition of Ad5-156R to Ad2-infected cells increased OI 15-fold. Adenovirus serotypes from the same subfamily have a very small difference in protein sequence in comparison (FIG. 13). The closest adenovirus family member to Ad5 is Ad2. Addition of Ad2-156R to Ad5wt-infected cells increased OI almost 3-fold.

Discussion

It was early discovered that the RNA expressed from the adenovirus E1B gene region had a complex splicing pattern. The full-length 2.28 kb long RNA is polycistronic carrying two overlapping reading frames. The alternative usage of either an early weak or a strong down-stream translation start site produces E1B-19k and E1B-55k, respectively (Perricaudet, Akusjarvi et al. 1979; Bos, Polder et al. 1981). A common splice donor early in the 55k ORF is used to splice to three alternative splice acceptors, 93R SA, 156R SA and 84R SA (Anderson, Schmitt et al. 1984; Virtanen and Pettersson 1985; Anderson, Maude et al, 1987). The 93R AS splices out of frame with the 55k ORF adding a 15 amino acid C-terminus. The 156R AS splices in frame with E1B-55k removing the 340 middle amino acids. The 84R SA is a down-stream site adding 6 amino acids to the common N-terminus.

When making a large set of gene-modified viruses based on the wild type adenovirus serotype 5 strain pTG3602 one viral clone was mutated at a single nucleotide position (SNP) in the E1B-55k gene region. The mutation was made inside the splice acceptor sequence of E1B-93R, or more precisely, it changed the putative site from cag/ga to cGg/ga. Not only did the mutation change the splice site but it also changed E1B-55k amino acid 400 from an arginine to a glycine. This virus has been named Ixovex. We have characterised this virus when it comes to oncolytic potential, meaning, retaining replication capacity and cytotoxicity in cancer cells while being inhibited on both accounts in normal cells.

Our results show that the mutation leads to a lack of expressed E1B-55k protein in infected cells (FIG. 3). We believe this is because the amino acid change destabilises the E1B-55k protein. Others have introduced amino acid changes into E1B-55k and several of these made the protein level unstable. In addition, our mutation changes an important nucleotide in the E1B-55k splice acceptor site 93R, which negates splicing to that particular splice site (FIG. 4). To compensate, the splicing appears to be re-directed to the E1B-156R splice acceptor. With the lack of E1B-55k in the infection, Ixovex's ability to inhibit the expression of p53 is severely reduced (FIG. 5). The reduced level of induced p53 by Ixovex compared to Onyx-015 could have been because of the slightly lower replication efficiency of Ixovex in A549 cells, i.e. the cells are less affected, hence less p53 is expressed. Alternatively, and what we believe, the increased splicing to the 156R splice acceptor (FIG. 4) may also increase expression of the E1B-156R protein. The 156R splicing splices in-frame with the C-(carboxy)-terminal part of E1B-55k. This removes the middle 340 amino acids leaving the C-terminal 78 amino acids fused to the N-(amino)-terminal 79 amino acids. The Dobner lab has shown (Sieber and Dobner 2007) that the E1B-156R protein retains some ability to inhibit p53 through its C-terminus. It is also possible that E1B-156R retains other functions of the E1B-55k protein. The E1B-55k and E1B-156R protein interacts with many similar factors (Sieber and Dobner 2007; Schreiner, Wimmer et al. 2010; Schreiner, Wimmer et al. 2011; Wimmer, Blanchette et al. 2012). E1B-55k has been assigned several functions besides mediating the degradation of p53. It is also connected to regulating the selective nuclear export of late viral RNA (Dobner and Kzhvshkowska 2001; Flint and Gonzalez 2003) and inhibiting translation of cellular RNA while promoting viral RNA translation (Blackford and Grand 2009). The main functions of E1B-55k are mediated when the protein is in complex with another viral protein, the E4orf6. Interestingly, the E1B-156R protein has been shown to interact with the E4orf6 protein (Sieber and Dobner 2007). The E1B-156R might compensate for some of these functions, which fit with the increased expression of E1B-156R by Ixovex.

In normal cells, the toxicity of each virus largely mirrored respective replication capacity. The lack of toxicity and the almost complete shutdown of replication in normal cells indicate an astounding safety profile of Ixovex. That the Onyx-015 virus replicated better in normal cells than Ixovex is intriguing considering that the deletion the Onyx-015 virus carries removes all possibilities to express E1B-55k, -93R and -156R protein (Barker and Berk 1987). This indicates that it is the imbalance of expression in the E1B region that had the extensive impact on the attenuation of Ixovex in normal cells in comparison to the other viruses. Interestingly, the difference in replication in normal cells between Onyx-015 and Ixo-ctrl on one hand and Ixovex on the other was not seen in the cancer cells. This indicates that the Ixovex infection in normal cells has become non-permissive, i.e. there is probably a major blockage early in infection giving the cells time to clear the virus, whereas the transformed state of cancer cells compensates for the lack of some E1B-55k function(s).

The effect of the imbalanced E1B expression in cancer cells was different depending on cancer cell line. The cytotoxicity of Ixovex in the two highly replication-permissive cell lines H1299 and H460 was low while the cytotoxicity was high in the replication-attenuated cell lines, A549 and HeLa. The reason for this is probably because of the toxicity, the cells died before producing high numbers of virus.

The adenovirus family is divided into 7 genera, named A-G, with a total of more than 65 different serotypes. Serotype 5 (Ad5) belongs to genera C. We believe that the splicing pattern seen in Ad5 is conserved among all adenovirus serotypes and that the imbalance through splice site mutation causing a very advantageous oncoselectivity for Ad5 would be mirrored in most if not all of the other serotypes. Our preliminary experiments show similar splicing patterns in representative viruses from each of the different genera (A-Ad12, B 1-Ad3, B2-Ad11, C-Ad5, D-Ad37, E-Ad4 and F-Ad40).

The overall higher efficacy of the Ad5wt virus to all the other viruses is probably due to the wild type strain pTG3602 (Oberg, Yanover et al 2010), used as genome backbone for Ixovex and Ixo-ctrl. This backbone carries a few point mutations scattered throughout the genome. Our Ixo-ctrl virus is actually pTG3602 in essence. The SNP in Ixovex was reverted back to wild type state producing the Ixo-ctrl virus. In the numerous experiments where pTG3602 has been employed a constant lower efficacy has been seen, as compared to the Ad5wt.

An additional advantage of Ixovex in comparison to patented adenovirus vectors of similar approach is that the Onyx-015 (Heise, Sampson-Johannes et al. 1997), -051 and -053 (Shen, Kitzes et al 2001) all are missing the E3B gene region of the virus. This region was originally deleted to enhance the safety profile of Onyx-015. It was later found that the elimination of this region made the vector prematurely cleared from the tumour by the immune defence (Wang, Hallden et al. 2003).

Through the western blot analysis on infections in H1299 cells it was shown that Ixovex replicates and expresses viral proteins to the same level as Ad5wt. The only difference between the viruses was seen when using a specific antibody for the N-terminal region of E1B-55k (mouse-m2A6), a drastic increase in the E1B-156R spliceoform of the E1B-55k protein (FIG. 10). We decided to perform a number of complementation experiments to verify whether indeed an increase in E1B-156R could be responsible for the increase in Oncolytic Index (OI). In FIGS. 11A, 11B and 11C and FIG. 12, we show that adenovirus type 5 E1B-156R is a potent enhancer of the OI in the subfamily group C. The E1B-156R equivalent from Ad2wt was also shown to have a positive effect on the OI of Ad5wt. Interestingly, adding Ad5-156R to Ad5wt-infected H460 cells increased the replication of the virus, which was in line with the much higher replication level of Ixovex as compared to the ONYX-015 virus (lacking the E1B-156R gene) in H460 cells (see FIG. 6).

It is important to note that these experiments, where E1B-156R is supplemented to the virus-infected cells does not completely resemble infection with Ixovex or another engineered virus that expresses E1B-156R. For example, during viral infection with Ixovex Ad5-156R levels are increased when the virus replicates, i.e. the amount of expression template (viral DNA) increases. In contrast, in the complementation experiments the E1B-156R is provided at a constant template level, i.e. as the cells continue to divide during the early phase of the infection the plasmid harbouring the E1B-156R gene is diluted. Thus, when the virus starts replicating E1B-156R expression will not increase exponentially (as would be the case for a viral copy). However, these experiments clearly show that addition of E1B-156R has the effect of increasing oncolytic index and suggest that E1B-156R is responsible for this effect.

REFERENCES

Anderson, C. W., R. C. Schmitt, et al. (1984). "Early region 1B of adenovirus 2 encodes two coterminal proteins of 495 and 155 amino acid residues." *Journal of virology* 50(2): 387-396.

Anderson, R. E., M. B. Maude, et al. (1987). "Abnormal plasma levels of polyunsaturated fatty acid in autosomal dominant retinitis pigmentosa." *Experimental eye research* 44(1): 155-159.

Barker, D. D. and A. J. Berk (1987). "Adenovirus proteins from both E1B reading frames are required for transformation of rodent cells by viral infection and DNA transfection." *Virology* 156(1): 107-121.

Beatty, M. S. and D. T. Curiel (2012). "Adenovirus strategies for tissue-specific targeting." *Advances in cancer research* 115: 39-67.

Blackford, A. N. and R. J. Grand (2009). "Adenovirus E1B 55-kilodalton protein: multiple roles in viral infection and cell transformation." *Journal of virology* 83(9): 4000-4012.

Bos, J. L., L. J. Polder, et al. (1981). "The 2.2 kb E1b mRNA of human Ad12 and Ad5 codes for two tumor antigens starting at different AUG triplets." *Cell* 27(1 Pt 2): 121-131.

Bradshaw, A. C. and A. H. Baker (2012). "Gene therapy for cardiovascular disease: Perspectives and potential." *Vascular pharmacology*.

Bradshaw, A. C., L. Coughlan, et al. (2012). "Biodistribution and inflammatory profiles of novel penton and hexon double-mutant serotype 5 adenoviruses." *Journal of controlled release: official journal of the Controlled Release Society*.

Dobner, T. and J. Kzhyshkowska (2001). "Nuclear export of adenovirus RNA." *Current topics in microbiology and immunology* 259: 25-54.

Flint, S. J. and R. A. Gonzalez (2003). "Regulation of mRNA production by the adenoviral E1B 55-kDa and E4 Orf6 proteins." *Current topics in microbiology and immunology* 272: 287-330.

Heise, C., A. Sampson-Johannes, et al. (1997). "ONYX-015, an E1B gene-attenuated adenovirus, causes tumor-specific cytolysis and antitumoral efficacy that can be augmented by standard chemotherapeutic agents." *Nature medicine* 3(6): 639-645.

Nasz, I., E. Adam, et al. (2001). "Alternate adenovirus type-pairs for a possible circumvention of host immune response to recombinant adenovirus vectors." *Acta microbiologica et immunologica Hungarica* 48(2): 143-146.

Oberg, D., E. Yanover, et al. (2010). "Improved potency and selectivity of an oncolytic E1ACR2 and E1B19K deleted adenoviral mutant in prostate and pancreatic cancers." *Clinical cancer research: an official journal of the American Association for Cancer Research* 16(2): 541-553.

Perricaudet, M., G. Akusjarvi, et al. (1979). "Structure of two spliced mRNAs from the transforming region of human subgroup C adenoviruses." *Nature* 281(5733): 694-696.

Schreiner, S., P. Wimmer, et al. (2011). "Adenovirus type 5 early region 1B 55K oncoprotein-dependent degradation of cellular factor Daxx is required for efficient transformation of primary rodent cells." *Journal of virology* 85(17): 8752-8765.

Schreiner, S., P. Wimmer, et al. (2010). "Proteasome-dependent degradation of Daxx by the viral E1B-55K protein in human adenovirus-infected cells." *Journal of virology* 84(14): 7029-7038.

Shen, Y., G. Kitzes, et al. (2001). "Analyses of single-amino-acid substitution mutants of adenovirus type 5 E1B-55K protein." *Journal of virology* 75(9): 4297-4307.

Sieber, T. and T. Dobner (2007). "Adenovirus type 5 early region 1B 156R protein promotes cell transformation independently of repression of p53-stimulated transcription." *Journal of virology* 81(1): 95-105.

Virtanen, A. and U. Pettersson (1985). "Organization of early region 1B of human adenovirus type 2: identification of four differentially spliced mRNAs." *Journal of virology* 54(2): 383-391.

Wang, Y., G. Hallden, et al. (2003). "E3 gene manipulations affect oncolytic adenovirus activity in immunocompetent tumor models." *Nature biotechnology* 21(11): 1328-1335.

Wimmer, P., P. Blanchette, et al. (2012). "Cross-talk between phosphorylation and SUMOylation regulates transforming activities of an adenoviral oncoprotein." *Oncogene*.

The invention claimed is:

1. A method for treating cancer in a subject, comprising:
   a) administering a therapeutically effective dose of a recombinant adenovirus to the subject in combination with an additional antineoplastic protocol;
   b) allowing sufficient time for said recombinant adenovirus to infect neoplastic cells of said cancer; and
   c) optionally administering further doses of the recombinant adenovirus, wherein the recombinant adenovirus is characterised in that the proportion of the E1B 156R isoform is increased relative to wild-type levels, and wherein the adenovirus has an oncolytic effect in a cancer cell, and wherein the recombinant adenovirus carries a mutation in the sequence of the E1B gene of the adenovirus and the mutation in the E1B gene is A3216G wherein the numbering is relative to adenovirus Ad5 genome (accession number AC 000008.1) (SEQ ID NO: 41) (position 1503 in the E1B gene (SEQ ID NO: 1)) or a guanine point mutation at an equivalent position to 3216 in any other adenovirus serotype.

2. The method of claim 1, wherein the recombinant adenovirus is administered intravenously, intraperitoneally, intramuscularly, subdermally, topically or inhaled as a mist.

3. The method of claim 1, wherein the recombinant adenovirus is administered in a dose comprising about $10^3$ to $10^{15}$ or more virion particles per ml.

4. The method of claim 1, wherein the proportion of the E1B-156R isoform is increased at least 2 fold, 4-fold, 10-fold, 100-fold, 1,000-fold or 10,000-fold relative to wild-type levels.

5. The method of claim 1, wherein the wild-type E1B gene has the polynucleotide sequence according to SEQ ID NO: 1.

6. The method of claim 1, wherein the recombinant adenovirus is adenovirus serotype Ad5, or adenovirus serotype Ad5 strain pTG3602.

7. The method of claim 1, wherein the E1B-156R isoform has a polynucleotide sequence that has at least 80% sequence identity to SEQ ID NO: 2; and/or the E1B-156R isoform has a polypeptide sequence that has at least 80% sequence identity to SEQ ID NO: 3.

8. The method of claim 1, wherein the neoplastic cells substantially lack p53 function.

9. The method of claim 1, wherein the cancer is a bronchogenic carcinoma, nasopharyngeal carcinoma, laryngeal carcinoma, small cell and non-small cell lung carcinoma, lung adenocarcinoma, hepatocarcinoma, pancreatic carcinoma, bladder carcinoma, colon carcinoma, breast carcinoma, cervical carcinoma, ovarian carcinoma or lymphocytic leukaemia.

10. The method of claim 1, wherein the additional antineoplastic protocol is conventional chemotherapy.

* * * * *